United States Patent
Lu et al.

(10) Patent No.: US 10,646,433 B2
(45) Date of Patent: *May 12, 2020

(54) INTRAVENOUS ADMINISTRATION OF TRAMADOL

(71) Applicant: Revogenex Ireland Ltd, Dublin (IE)

(72) Inventors: Lucy Lu, New York, NY (US); Scott Reines, New York, NY (US); Jeffrey Ping, Suwanee, GA (US)

(73) Assignee: Revogenex Ireland Ltd., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/223,556

(22) Filed: Dec. 18, 2018

(65) Prior Publication Data

US 2019/0175493 A1    Jun. 13, 2019

Related U.S. Application Data

(63) Continuation of application No. 15/976,503, filed on May 10, 2018, which is a continuation of application No. 15/612,665, filed on Jun. 2, 2017, now Pat. No. 9,968,551, which is a continuation of application No. 15/163,111, filed on May 24, 2016, now Pat. No. 9,693,949.

(60) Provisional application No. 62/271,107, filed on Dec. 22, 2015.

(51) Int. Cl.
| A61K 9/00 | (2006.01) |
| A61K 31/135 | (2006.01) |
| A61P 25/00 | (2006.01) |
| A61P 25/04 | (2006.01) |
| A61K 31/138 | (2006.01) |

(52) U.S. Cl.
CPC .......... *A61K 9/0019* (2013.01); *A61K 9/0053* (2013.01); *A61K 31/135* (2013.01); *A61K 31/138* (2013.01); *A61P 25/00* (2018.01); *A61P 25/04* (2018.01)

(58) Field of Classification Search
CPC .. A61K 31/135; A61K 9/0019; A61K 9/0053; A61P 25/00; A61P 25/04; A61P 29/00
See application file for complete search history.

(56) References Cited

U.S. PATENT DOCUMENTS

| 5,919,826 | A | 7/1999 | Caruso et al. |
| 6,297,286 | B1 | 10/2001 | Huckle |
| 6,339,105 | B1 | 1/2002 | Kamin et al. |
| 6,376,550 | B1 | 4/2002 | Raber et al. |
| 6,593,373 | B2 | 7/2003 | Koegel et al. |
| 6,702,839 | B1 | 3/2004 | Dae et al. |
| 6,713,470 | B2 | 3/2004 | Jackson |
| 6,875,447 | B2 | 4/2005 | Bartholomäus et al. |
| 6,916,486 | B2 | 7/2005 | Klose et al. |
| 7,611,730 | B2 | 11/2009 | Bartholomäus et al. |
| 7,700,626 | B2 | 4/2010 | Buehler |
| 8,895,622 | B2 | 11/2014 | Kottayil |
| 9,693,949 | B1 * | 7/2017 | Lu .......... A61K 9/0019 |
| 9,968,551 | B2 * | 5/2018 | Lu .......... A61K 9/0019 |
| 9,980,900 | B2 * | 5/2018 | Lu .......... A61K 9/0019 |
| 10,022,321 | B2 * | 7/2018 | Lu .......... A61K 31/135 |
| 2005/0089558 | A1 | 4/2005 | Cutler et al. |
| 2005/0137235 | A1 | 6/2005 | Szelenyi et al. |
| 2006/0188583 | A1 | 8/2006 | Lim et al. |
| 2007/0122478 | A1 | 5/2007 | Deboeck et al. |
| 2007/0265190 | A1 | 11/2007 | Thuresson et al. |
| 2008/0085263 | A1 | 4/2008 | Thuresson et al. |
| 2008/0181876 | A1 | 7/2008 | Johnson et al. |
| 2008/0261991 | A1 | 10/2008 | Bar-Or et al. |
| 2009/0082466 | A1 | 3/2009 | Babul |

(Continued)

FOREIGN PATENT DOCUMENTS

| EP | 2199274 | 6/2010 |
| WO | WO2008/137012 | 11/2008 |
| WO | WO2008/150324 | 12/2008 |

OTHER PUBLICATIONS

Iurie Acalovschi, et al. "Tramadol Added to Lidocaine for Intravenous Regional Anesthesia" Anesthesia & Analgesia, 2001, vol. 92. pp. 209-214.

(Continued)

*Primary Examiner* — My-Chau T. Tran
(74) *Attorney, Agent, or Firm* — Davidson, Davidson & Kappel, LLC

(57) ABSTRACT

A method of treating pain, e.g., acute post-operative pain, by administering to a human patient(s) a therapeutically effective dose of tramadol intravenously in a dosing regimen which includes one or more loading doses administered at shortened intervals as compared to dosing at steady-state is disclosed. In certain embodiments, the dose of tramadol is from about 45 mg to about 80 mg and the second (and optionally) third doses are intravenously administered at intervals of from about 2 to about 3 hours, and thereafter the tramadol is intravenously administered at a dosing interval of about 4 to about 6 hours, until the patient no longer requires treatment with tramadol. In preferred embodiments, the intravenous dosing regimen provides a Cmax and AUC of tramadol is similar to the Cmax and AUC of an oral dose of 100 mg tramadol HCl given every 6 hours. In certain preferred embodiments, the dosing regimen comprises 50 mg IV tramadol at Hour 0, followed by 50 mg at Hour 2, 50 mg at hour 4, and 50 mg every 4 hours thereafter (e.g., until the patient no longer requires treatment with tramadol).

15 Claims, 12 Drawing Sheets

(56) References Cited

U.S. PATENT DOCUMENTS

| | | |
|---|---|---|
| 2009/0285862 A1 | 11/2009 | Goodchild et al. |
| 2011/0039875 A1 | 2/2011 | Singh |
| 2013/0189354 A1 | 7/2013 | Singh et al. |
| 2013/0296437 A1 | 11/2013 | Young et al. |
| 2015/0093438 A1 | 4/2015 | Young et al. |
| 2015/0313892 A1 | 11/2015 | Singh et al. |
| 2018/0360741 A1* | 12/2018 | Lu .................. A61K 9/0019 |
| 2019/0167570 A1* | 6/2019 | Lu .................. A61K 9/0019 |
| 2019/0167571 A1* | 6/2019 | Lu .................. A61K 9/0019 |
| 2019/0175492 A1* | 6/2019 | Lu .................. A61K 9/0019 |
| 2019/0175493 A1* | 6/2019 | Lu .................. A61K 9/0019 |
| 2019/0231680 A1* | 8/2019 | Lu .................. A61K 9/0019 |
| 2019/0231681 A1* | 8/2019 | Lu .................. A61K 9/0019 |

OTHER PUBLICATIONS

S Aghamir, et al. "Propacetamol Vs. Tramadol for Post-Operative Pain Management After Urologic Surgery" The Internet Journal of Pharmacology, 2005, vol. 4, No. 2. pp. 1-9.

Vanita Ahuja, et al. "Comparison of analgesic efficacy of flupirtine maleate and ibuprofen in gynaecological ambulatory surgeries: A randomized controlled trial" Indian Journal of Anaesthesia, Jul. 2015. pp. 411-415.

Taylan Akkaya, et al. "Saphenous nerve block is an effective regional technique for post-menisectomy pain" Knee Surg Sports Traumatol Arthrosc, 2008, vol. 16. pp. 855-858.

Alagol, et al. "The use of intraarticular tramadol for postoperative analgesia after arthroscopic knee surgery:a comparison of different intraarticular and intravenous doses" Knee Surg Sports Traumatol Arthrosc, 2004, vol. 12. pp. 184-188.

Albertoni Giraldes, et al. "Tramadol wound infiltration is not different from intravenous tramadol in children: a randomized controlled trial" Journal of Clinical Anesthesia, 2016, vol. 28. pp. 62-66.

Alhashemi, et al. "Dexmedetomidine in combination with morphine PCA provides superior analgesia for shockwave lithotripsy" Canadian Journal of Anesthesia, 2004, vol. 51, No. 4. pp. 342-347.

Andreou, et al. "Randomized study comparing piroxicam analgesia and tramadol analgesia during outpatient electromagnetic extracorporeal lithotripsy" Prof Urol, Apr. 2006, vol. 16, No. 2. pp. 155-159.

Arslan, et al. "Comparison of the analgesic effects of intravenous paracetamol and lornoxicam in postoperative pain following thyroidectomies" Agri, 2011, vol. 23, No. 4. pp. 160-166.

Arslan, et al. "Comparing the efficacy of preemptive intravenous paracetamol on the reducing effect of opioid usage in cholecystectomy" Official Journal of Isfahan University of Medical Science, Mar. 2013. pp. 172-177.

Arti, et al. The comparison effects of intra-articular injection of different opioids on postoperative pain relieve after arthroscopic anterior cruciate ligament reconstruction: A randomized clinical trial study Official Journal of Isfahan University of Medical Science, 2011, vol. 16, No. 9. pp. 1176-1182.

Aydogan, et al. "Effectiveness of Preemptive Analgesia Using a Frequency Rhythmic Electrical Modulation System in Patients Having Instrumented Fusion for Lumbar Stenosis" Asian Spine Journal, 2014, vol. 8, No. 2. pp. 190-196.

Badaoui, et al. "Observational study on outpatient sleeve gastrectomy" Annales Francaises d'Anesthesie et de Reanimation, 2014, vol. 33. pp. 497-502. Abstract in English only.

Bajwa, et al. "A comparative evaluation of epidural and general anaesthetic technique for renal surgeries: A randomised prospective study" Indian Journal of Anaesthesia, Jul.-Aug. 2014, vol. 58, Issue 4. pp. 410-415.

Bala et al. "Effect of Scalp Block on Postoperative Pain Relief in Craniotomy Patients" Anaesthesia and Intensive Care, Apr. 2006, vol. 34, No. 2. pp. 224-227.

Banerjee, et al. "PONV in Ambulatory surgery: A comparison between Ramosetron and Ondansetron: a prospective, double-blinded, and randomized controlled study" Saudi Journal of Anaesthesia, Jan.-Mar. 2014, vol. 8, No. 1. pp. 1-6.

Beigh, et al. "Effects of Peritonsillar Injection of Tramadol and Adrenaline before Tonsillectomy" Iranian Journal of Otorhinolaryngology, Jun. 2013, No. 3, vol. 25, Serial No. 72. pp. 135-140.

Biancomi, et al. "The Pharmacokinetics and Efficacy of Ropivacaine Continuous Wound Instillation After Spine Fusion Surgery" Anesthesia Analgesia, 2004, vol. 98. pp. 166-172.

Bilotta, et al. "Nefopam and Tramadol for the Prevention of Shivering During Neuraxial Anesthesia" Regional Anesthesia and Pain Medicine, Jul.-Aug. 2002, vol. 27, No. 4. pp. 380-384.

Bloch, et al. "Tramadol Infusion for Postthoracotomy Pain Relief: A Placebo-Controlled Comparison with Epidural Morphine" Anesthesia Analgesia, 2002, vol. 94. pp. 523-528.

Bolat, et al. "The effect of preoperative intravenous dexketoprofen trometamol on postoperative pain in minor outpatient urologic surgery" Turkish Journal of Urology, 2013, vol. 39, No. 3. pp. 175-180.

Borazan, et al. "Prevention of Propofol Injection Pain in Children: A Comparison of Pre-treatment with Tramadol and Propofol-Lidocaine Mixture" International Journal of Medical Science, 2012. vol. 9, No. 6. pp. 492-497.

Braz, et al. "Genotoxicity, cytotoxicity and gene expression in patients undergoing elective surgery under isoflurane anaesthesia" Mutagenesis, Jan. 2011, vol. 26, No. 3. pp. 415-420.

Brogly, et al. "Gabapentin Attenuates Late but Not Early Postoperative Pain After Thyroidectomy with Superficial Cervical Plexus Block" Anesthesia & Analgesia, Nov. 2008, vol. 107, No. 5. pp. 1720-1725.

Cander et al. "The Effectiveness of Analgesics in Traumatic Injuries of the Extremities" Advances in Therapy, Sep./Oct. 2005, vol. 22, No. 5. pp. 462-466.

Casti, et al. "Lidocaine versus ropivacaine for continuous interscalene brachial plexus block after open shoulder surgery" ACTA Anaesthesiologica Scandinavia, 2003, vol. 47. pp. 355-360.

Chakraborty, et al. "Effect of clonidine as adjuvant in bupivacaine-induced supraclavicular brachial plexus block: A randomized controlled trial" Indian Journal of Pharmacology, Apr. 2010, vol. 42, No. 2, pp. 74-77.

Cheon, et al. "A comparison between caudal block versus splash block for postoperative analgesia following inguinal herniorrhaphy in children" Korean Journal of Anesthesiol, Apr. 2011, vol. 60, No. 4. pp. 255-259.

Choi, et al. "Can intravenous patient-controlled analgesia be omitted in patients undergoing laparoscopic surgery for colorectal cancer?" Annals of Surgical Treatment and Research, 2015, vol. 88, No. 2. pp. 86-91.

Cubukcu, et al. "Effect of ondansetron in lower extremity bone surgery on morphine and tramadol consumption using patient controlled analgesia" Agril, 2007, vol. 19, No. 1. pp. 36-41. English summary only.

Daskiewicz, et al. "Postoperative analgesia in a morbidly obese patient with chronic renal failure" Anestezjol Intens Ter., Oct.-Dec. 2010, vol. 42, No. 4. pp. 197-200.

Dave, et al. "Anaesthetic implications of paediatric thoracoscopy" Journal of Minimal Access Surgery, Jan.-Mar. 2005. pp. 1-6.

Demiraran, et al. "A comparison of the postoperative analgesic efficacy of single-dose epidural tramadol versus morphine in children" British Journal of Anaesthesia, Aug. 2005, vol. 95, No. 4. pp. 510-513.

Den-berg, et al. "The effects of tramadol on postoperative nausea^, vomiting and headache after ENT surgery. A placebo-controlled comparison with equipotent doses of nalbuphine and pethidine" Acta Anaesthesiologica Scandinavica, 1999, vol. 43. pp. 28-33.

Deniz, et al. "Comparison of the postoperative analgesic efficacy of an ultrasound-guided fascia iliaca compartment block versus 3 in 1 block in hip prosthesis surgery" Agri, 2014, vol. 26, No. 4. pp. 151-157.

Dubey, et al. "Anesthetic considerations in a patient with visceral leishmaniasis" Canadian Journal of Anesthesia, 2001. pp. 529-531.

Ekmekc, et al. "The efficacy of adding dexketoprofen trometamol to tramadol with patient controlled analgesia technique in post-

(56) References Cited

OTHER PUBLICATIONS laparoscopic cholecystectomy pain treatment" Agri, 2012, vol. 24, No. 2. pp. 63-68. English summar only.

Elakany, et al. "Segmental thoracic spinal has advantages over general anesthesia for breast cancer surgery" Anesthesia: Essays and Researches. Sep.-Dec. 2013. pp. 390-395.

Enggaard, et al. "The Analgesic Effect of Tramadol After Intravenous Injection in Healthy Volunteers in Relation to CYP2D6" Anesthesia & Analgesia. 2006, vol. 102. pp. 146-150.

Ertas, et al. "The effectivenciss of subcutaneously implanted epidural ports for relief of severe pain in patients with advanced-stage gynecological cancer: a prospective study" Agri, 2014, vol. 26, No. 1. pp. 8-14. English summary only.

Esme, et al. "Comparison between intermittent intravenous analgesia and intermittent paravertebral subpleural analgesia for pain relief after thoracotomy" European Journal of Cardio-Thoracic Surgery, 2012. vol. 41. pp. 10-13.

Fanelli, et al. "Pilot double-blinded study to assess efficacy and tolerability of morphine sulphate oral solution (Oramorph®) given preoperatively as add-on therapy within a multimodal postoperative pain approach in patients undergoing laparoscopic cholecystectomy" Minerva Anestesiol, Jan. 2014, vol. 80, No. 1. pp. 66-75.

Floris, et al. "Efficacy of intravenous tramadol treatment for reducing pain during office diagnostic hysteroscopy" Tramadol and Office Hysteroscopy, Jan. 2007, vol. 87, No. 1. pp. 147-151.

Gambaro, et al. "Validation of a GC/MS method for the determination of tramadol in human plasma after intravenous bolus" Il Farmaco, 2003, vol. 58. pp. 947-950.

Gedik, et al. "Protective effect of heparin in the end organ ischemia/reperfusion injury of the lungs and heart" Journal of Cardiothoracic Surgery, 2012. pp. 1-7.

Gu, et al. "Effects of epidural anesthesia and postoperative epidural analgesia on immune function in esophageal carcinoma patients undergoing thoracic surgery" Molecular and Clinical Oncology,2015, vol. 3. pp. 190-196.

Guilherme, et al. "Epidural infusion of Clonidine or Clonidine Plus Ropivacaine for Postoperative Analgesia in Children Undergoing Major Abdominal Surgery" Journal of Clinical Anesthesia, 2003, vol. 15. pp. 510-514.

Guizilini, et al. "Pleural subxypnoid drain confers better pulmonary function and clinical outcomes in chronic obstructive pulmonary disease after off-pump coronary artery bypass grafting: a randomized controlled trial" Rev Bras Cir Cardiovasc Surg, 2014, vol. 29, No. 4. pp. 588-594.

Gulcin, et al. "The comparison of analgesic effects of various administration methods of diclofenac sodium transdermal oral and intramuscular in early postoperative period in laparoscopic cholecystectomy operations" Pakistan Journal of Medical Science, Feb. 28, 2014. pp. 1-5.

Gunes, et al. "Comparison of caudal vs intravenous tramadol administered either preoperatively or postoperatively for pain relief in boys" Pediatric Anesthesia, 2004, vol. 14. pp. 324-328.

Han Chan, et al. "Control of shivering under regional anesthesia in obstetric patients with tramadol" Cancer Journal of Anesthesia, 1999, Voume 46, No. 3. pp. 253-258.

Han, et al. "Transmesocolic Approach for Left Side Laparoscopic Pyeloplasty: Comparison with Laterocolic Approach in the Initial Learning Period" Yonsei Medical Journal, 2013, vol. 54, No. 1. pp. 197-203.

Iannuzzi, et al. "Desflurane and sevoflurane in elderly patients during general anesthesia: a double blind comparison" Minerva Anestesiol, 2005. vol. 71. pp. 147-155.

Imani, et al. "The maternal and neonatal effects of adding tramadol to 2% lidocaine in epidural anesthesia for cesarean section" Jul. 2011, vol. 1, No. 1, pp. 25-29.

James, et al. "Intravenous Tramadol Versus Epidural Morphine for Postthoractomy Pain Relief: A Placebo-Controlled Double-Blind Trial" Anesthesia & Analgesia, 1996, vol. 83. pp. 87-91.

Joshi, et al. "Comparative evaluation of intrathecal midazolam and low dose clonidine: Efficacy, safety and duration of analgesia. A randomized, double blind, prospective clinical trial" Indian Journal of Pharmocology, May-Jun. 2012. vol. 44, No. 3. pp. 357-361.

Kanazi, et al. "The Analgesic Efficacy of Subarachnoid Morphine in Comparison with Ultrasound-Guided Transversus Abdominis Plane Block After Cesarean Delivery: A Randomized Controlled Trial" Anesthesia & Analgesia, Aug. 2010, vol. 111, No. 2. pp. 475-481.

Karaasian, et al. "Comparison of Dexmedetomidine and Midazolam for Monitored Anesthesia Care Combined with Tramadol via Patient-Controlled Analgesia in Endoscopic Nasal Surgery: A Prospective, Randomized, Double-Blind, Clinical Study" Current Therapeutic Research, Mar./Apr. 2007, vol. 68, No. 2. pp. 69-81.

Karamanlioglu, et al. "Preoperative Oral Rofecoxib Reduces Postoperative Pain and Tramadol Consumption in Patients After Abdominal Hysterectomy" Anesthesia & Analgesa, 2004, vol. 98. pp. 1039-1043.

Karlekar, et al. "Assessment of feasibility and efficacy of Class IV laser therapy for postoperative pain relief in off-pump corollary artery bypass surgery patients: A pilot study" Annals of Cardiac Anaesthesia, Jul.-Sep. 2015, vol. 18. pp. 317-322.

Kaygusuz, et al. "Efficacy of Preventive Analgesia with Tramadol or Lornoxicam for Percutaneous Nephrolithotomy: A Prospective, Randomized, Double-Blind, Placebo-Controlled Study" Current Therapeutic Research, Jul./Aug. 2007, vol. 68, No. 4. pp. 205-216.

Knaggs, et al. "The Pupillary Effects of Intravenous Morphine, Codeine, and Tramadol in Volunteers" Anesthesia & Analgesia, 2004. vol. 99. pp. 108-112.

Kocabas, et al. "The use of tramadol and morphine for pain relief after abdominal hysterectomy." Clin Exp Obstet Gynecol, 2005, vol. 32, No. 1. pp. 45-48.

Koltka, et al. "Comparison of efficacy of intraarticular application of magnesium, levobupivacaine and lornoxicam with placebo in arthroscopic surgery" Knee Surg Sports Traumatol Arthrosc, 2011, vol. 19. pp. 1884-1889.

Kwok Fu, et al. "Comparison of tramadol and tramadol/droperidol mixture for patient controlled analgesia" Canadian Journal of Anaesthesia, 1997, vol. 44, No. 8. pp. 810-815.

Langlois, et al. "The addition of tramadol to lidocaine does not reduce tourniquet and postoperative pain during iv regional anesthesia" Canadian Journal of Anesthesia, 2002, vol. 49, No. 2. pp. 165-168.

Lauretti, et al. "Intrathecal ketorolac enhances intrathecal morphine analgesia following total knee arthroplasty" Journal of Anaesthesiology Clinical Pharmacology, Oct.-Dec. 2013, vol. 29, No. 4. pp. 503.

Lee et al. "Comparison of effects of intraoperative esmolol and ketamine infusion on acute postoperative pain after remifentanil-based anesthesia in patients undergoing laparoscopic cholecystectomy" Korean Journal Anesthesiol, Mar. 2014, vol. 66, No. 3. pp. 222-229.

Lim, et al. "Analgesic effect of preoperative versus intraoperative dexamethasone after laparoscopic cholecystectomy with multimodal analgesia" Korean Journal Anesthesiol, Oct. 2011, vol. 61, No. 4. pp. 315-319.

Luc Morelmans et al. "Use of Tramadol Drip in Controlling Renal Colic Pain" Journal of Endourology, Dec. 2006., vol. 20, No. 12 pp. 1010-1015.

Mahendru, et al. "A comparison of intrathecal dexmedetomidine, clonidine, and fentanyl as adjuvants to hyperbaric bupivacaine for lower limb surgery: A double blind controlled study" Journal of Anesthesiology Clinical Pharmacology, Oct.-Dec. 2013, vol. 29, No. 4. pp. 496.

Mansour, et al. "Nonopioid versus opioid based general anesthesia technique for bariatric surgery: A randomized doubleblind study" Saudi Journal of Anaesthesia, Oct.-Dec. 2013. pp. 387.

Matkap, et al. "Preincisional local infiltration of tramadol at the trocar site versus intravenous tramadol for pain control after laparoscopic cholecystectomy" Journal of Clinical Anesthesia, 2011, vol. 23. pp. 197-201.

Mehta, et al. "Post operative analgesia after incisional infiltration of bupivacaine v/s bupivacaine with buprenorphine" Journal of Anesthesiology Clinical Pharmacology, Apr.-Jun. 2011. pp. 211.

Mittal, et al. "Randomised double-blind comparative study of dexmedetomidine and tramadol for post-spinal anaesthesia shivering" Indian Journal of Anaesthesia, May-Jun. 2014. pp. 257.

(56) References Cited

OTHER PUBLICATIONS

Montes, et al. "Use of intravenous patient-controlled analgesia for the documentation of synergy between tramadol and metamizol" British Journal of Anaesthesia, 2000, vol. 85, No. 2. pp. 217-223.
Morel, et al. "Preoperative Peribulbar Block in Patients Undergoing Retinal Detachment Surgery Under General Anesthesia: A Randomized Double-Blind Study" Anesthesia & Analgesia, 2006. vol. 102. pp. 1082-1087.
Murphy, et al. "Comparison of the postoperative analgesic efficacy of intravenous patient-controlled analgesia with tramadol to intravenous patient controlled analgesia with opioids" J Opioid Manag, Mar.-Apr. 2010, vol. 6, No. 2 pp. 141-147 Abstract Only.
Naja, et al. "Effect of clonidine versus dexmedetomidine on pain control after laparoscopic gastric sleeve: A prospective, randomized, double-blinded study" Saudi Journal of Anaesthesia, Nov. 2014, vol. 8, Supplement 1. pp. S57-S62.
Ozcan, et al. "Comparison of Three Analgesics for Extracorporeal Shock Wave Lithotripsy" Scand J Urol Nephrol, 2002. pp. 281-285.
Ozgur, et al. "Effects of a thoracic paravertebral block on postoperative analgesia in patients undergoing modified radical mastectomy" Agri, 2014, vol. 26, No. 4. pp. 179-183. Summary in English only.
Pal, et al. "Diclofenac is more effective for post-operative analgesia in patients undergoing lower abdominal gynecological surgeries: A comparative study" Anesthesia: Essays and Researches, May-Aug. 2014. pp. 192-196.
Pang, et al. "Patient-Controlled Analgesia with Tramadol Versus Tramadol Plus Lysine Acetyl Salicylate" Anesthesia & Analgesia, 2009, vol. 91. pp. 1226-1229.
Pang, et al. "Tramadol 2.5 mg•kg-1 appears to be the optimal intraoperative loading dose before patient-controlled analgesia" Canadian Journal Anesthesia, 2003, vol. 50, No. 1. pp. 48-51.
Pang, et al. "Patient-Controlled Analgesia with Tramadol Versus Tramadol Plus Lysine Acetyl Salicylate" Anesthesia Analgesia, 2000, vol. 91. pp. 1226-1229.
Parikh, et al. "The analgesic efficacy of ultrasound-guided transversus abdominis plane block for retroperitoneoscopic donor nephrectomy: A randomized controlled study" Saudi Journal of Anaesthesia, Jan.-Mar. 2013. pp. 43.
Peng, et al. "Continuous Femoral Nerve Block versus Intravenous Patient Controlled Analgesia for Knee Mobility and Long-Term Pain in Patients Receiving Total Knee Replacement: A Randomized Controlled Trial" Evidence-Based Complementary and Alternative Medicine, 2014, Article ID 569107, pp. 1-12.
Puigodollers, et al. "Postoperative pain after haemorrhoidectomy: role of impaired evacuation" Colorectal Disease, 2010, vol. 13. pp. 926-929.
Salman, et al. "The efficacy of the semi-blind approach of transversus abdominis plane block on postoperative analgesia in patients undergoing inguinal hernia repair: a prospective randomized double-blind study" Local and Regional Anesthesia, 2013. pp. 1-8.
Saracoglu, et al. "Comparative study of intravenous opioid consumption in the postoperative period" Biomed Pap Med Fac Univ Palacky Olomouc Czech Repub, Mar. 2012, vol. 156, vol. 1. pp. 48-51.
Sen, et al. "Efficacy of Continuous Epidural Analgesia versus Total Intravenous Analgesia on Postoperative Pain Control in Endovascular Abdominal Aortic Aneurysm Repair: A Retrospective Case-Control Stud" Biomed Resarch International, 2014 pp. 1-5.
Shen, et al. "Comparison of the analgesic efficacy of preemptive and preventive tramadol after lumpectomy" Pharmacological Reports, 2008, vol. 60. pp. 415-421.
Shukla, et al. "A comparative study of the effect of clonidine and tramadol on post-spinal anaesthesia shivering" Indian Journal of Anesthesia, May-Jun. 2011, vol. 55, No. 3. pp. 242-246.
Siddiqui, et al. "Tramadol versus Nalbuphine in total intravenous anaesthesia for Dilatation and Evacuation" J Pak Med Assoc, Feb. 2007, vol. 57, No. 2. pp. 67-70.
Gramke, et al. "Sublingual Piroxicam for Postoperative Analgesia: Preoperative Versus Postoperative Administration: A Randomized, Double-Blind Study" Anesthesia Analgesia, 2006, vol. 102. pp. 755-758.
Sinha, et al. "Laparoscopic Surgery Using Spinal Anesthesia" JSLS, 2008, vol. 12. pp. 133-138.
Sizer, et al. "A comparison of the effects of intraoperative tramadol and ketamine usage for postoperative pain relief in patients undergoing tonsillectomy" Agri, 2013, vol. 25, No. 2. pp. 47-54 Summary in English only.
Stamer, et al. "Concentrations of Tramadol and O-desmethyltramadol Enantiomers in Different CYP2D6 Genotypes" Clinical Pharmacology & Therapeutics, Jul. 2007, vol. 82, No. 1. pp. 41-47.
Tarkkila, et al. "Comparison of Respiratory Effects of Tramadol and Oxycodone" Journal of Clinical Anesthesia, 1997, vol. 9. pp. 582-585.
Tauzin-Fin, et al. "Wound infiltration with magnesium sulphate and ropivacaine mixture reduces postoperative tramadol requirements after radical prostatectomy" The Acta Anaesthesiologica Scandinavica Foundation, 2009, vol. 53. pp. 464-469.
Torres, et al. "Efficacy and Safety of Dipyrone Versus Tramadol in the Management of Pain After Hysterectomy: A Randomized, Double-Blind, Multicenter Study" Regional Anesthesia and Pain Medicine, Mar.-Apr. 2001, vol. 26, No. 2. pp. 118-124.
Tsai, et al. "A Comparison of Tramadol, Amitriptyline, and Meperidine for Postepidural Anesthetic Shivering in Parturients" Anesth. Analg, 2001. vol. 93. pp. 1288-1292.
Tuncer, et al. "Dexketoprofen for postoperative pain relief" Agri, 2006, vol. 18, No. 3. pp. 30-35 Sumarry in English only.
Unlugenc, et al. "A comparative study on the analgesic effect of tramadol, tramadol plus magnesium, and tramadol plus ketamine for postoperative pain management after major abdominal surgery" Acta Anaesthesiologica Scandinavica, 2002, vol. 46. pp. 1025-1030.
Unlugenc, et al. "A Comparative Study of the Analgesic Effect of Patient-Controlled Morphine, Pethidine, and Tramadol for Postoperative Pain Management After Abdominal Hysterectomy" Anesthesia & Analgesia, Jan. 2008, vol. 106, No. 1. pp. 309-312.
Uysal, et al. "The efficacy of intravenous paracetamol versus tramadol for postoperative analgesia after adenotonsillectomy in children" Journal of Clinical Anesthesia, 2011, vol. 23. pp. 53-57.
Uysal, et al. "Epileptic Seizure Following IV Tramadol in a Patient with Mental Retardation and Cerebellar Ataxia" Pain Medicine, 2011, vol. 12. pp. 833-836.
Vergnion, et al. "Tramadol, an Alternative to Morphine for Treating Posttraumatic Pain in the Prehospital Situation" Anesth Analg, 2001, vol. 92. pp. 1543-1546.
Wang, et al. "The effect of tramadol on serum cytokine response in patients undergoing pulmonary lobectomy" Journal of Clinical Anesthesia, 2005, vol. 17. pp. 444-450.
Wang, et al. "Preoperative tramadol combined with postoperative small-dose tramadol infusion after total abdominal hysterectomy: a double-blind, randomized, controlled trial" Pharmacological Reports, 2009. vol. 61. pp. 1198-1205.
Wordliczek, et al. "Influence of Pre- or Intraoperational Use of Tramadol (Preemptive or Preventive Analgesia) on Tramadol Requirement in the Early Postoperative Period" Polish Journal of Pharmacology, 2002, vol. 54 pp. 693-697.
Yilmaz, et al. "Effects of a thoracic paravertebral block on postoperative analgesia in patients undergoing modified radical mastectomy" Agri, 2014, vol. 26, No. 4. pp. 179-183. English summary only.
McCarberg et al. "Tramadol extended-release in the management of chronic pain" Therapeutics and Clinical Risk Management, vol. 3, No. 3, pp. 401-410 (2007).
Wei-Wu Pang, et al. "Tramadol 2.5 mg kg$^{-1}$ appears to be the optimal intraoperative loading dose before patient-controlled analgesia" Regional Anesthesia and Pain. vol. 50, 2003, pp. 48-51.
Wei-Wu Pang, et al. "Patient-controlled Analgesia with Tramadol Versus Tramadol Plus Lysine Acetyl Salicylate" Anesthesia Analgesia, vol. 91, 2000. pp. 1226-1229.

(56) References Cited

OTHER PUBLICATIONS

Luc J.M Mortelmans, et al. "Use of Tramadol Drip in Controlling Renal Colic Pain" Journal of Endourology, vol. 20, No. 12, Dec. 2006. pp. 1010-1015.
Gulcin, et al. "The comparison of analgesic effects of various administration methods of diclofenac sodium transdermal oral and intramuscular in early postoperative period in laparoscopic cholecystectomy operations".
Badaoui, et al. "Observational study on outpatient sleeve gastrectomy" Annales Francaises d'Anesthesie et de Reanimation, vol. 33, 2014. pp. 497-502 (Abstract in English).
Alhashemi, et al. "Dexmedetomidine in combination with morphine PCA provides superior analgesia for shockwave lithotripsy" Canadian Journal of Anesthesia, vol. 51, 2004. pp. 342-347.
Ahuja, et al. "Comparison of analgesic efficacy of flupirtine maleate and ibuprofen in gynaecological ambulatory surgeries: A randomized controlled trial" Indian Journal of Anesthesia. vol. 59, Jul. 2015. pp. 411-415.
Grunenthal Ltd. "Summary of Product Characteristics" Mar. 23, 2015. pp. 1-10.
Arici, et al. "Remifentanil/midazolam versus tramadol/midazolam use for colonoscopy" Hepatogastroenterology. vol. 50, Dec. 2003. Abstract only.
Stiller, et al. "The addition of tramadol to morphine via patient-controlled analgesia does not lead to better postoperative pain relief after total knee arthroplasty" Acta Anaesthesiologica Scandinavia, 2007, vol. 51. pp. 322-330.
Tramadol, CIMS Data_India. Accessed Jul. 29, 2010.
Vickers MD, Paravicini D. "Comparison of tramadol with morphine for post-operative pain following abdominal surgery." Eur J Anesthesiol. 1995;12: 265-71.
Rud U, Fischer MV, Mewes R, Paravcini D., "Postoperative Analgesie mit Tramadol Kontinuierliche Infusion versus repetitive" (Postoperative analgesia with tramadol. Continuous infusion versus repetitive bolus administration), 1994.
Chrubasik J, Buzina M, Schulte-Monting J, Atanassoff P, Alon E. "Intravenous tramadol for post-operative pain—comparison of intermittent dose regimens with and without maintenance infusion." Eur J Anaesthesiol. 1992;9:23-28).
Webb et al., Anesthesia & Analgesia, 2002, vol. 95, pp. 1713-1718.
Tramal® Data Sheet, Aug. 2008, published online by medsafe.govt.nz, downloaded on Feb. 4, 2014 from https://web.archive.org/web/20111018060034/http://www.medsafe.govt.nz/profs/Datasheet/t/TramalcapSRtabinjoraldrops.pdf, 12 pages.
Huseyin Sen, et al. "Epileptic seizure during patient-controlled analgesia with tramadol" European Society of Anaesthesiology, 2009, pp. 447.
Prescribing Information Trambax™ (Tramal Hydrochloride Injection); 2007; pp. 1.
UKPAR Tramadol 50mg/ml Solution for Injection/Infusion, Technical Leaflet, Beacon Pharmaceuticals; 2006 ; pp. 19-23.
Tramahexal® Injection, Tramadol Hydrochlroide Injection, Consumer Medicine Information, Apr. 2008, pp. 1-3.
Tramal® Solution for injection, Aug. 2008, pp. 1.
W. Lintz, et al. "Bioavailability of tramadol after i.m. injection in comparison to i.v. infusion" International Journal of Clinical Pharmacology and Therapeutics, vol. 37, Apr. 1999, pp. 175-183.
Wei-Wu Pang, MD, et al. "Comparison of patient-controlled analgesia (PCA) with tramadol or morphine" Can J Anesth, vol. 46, 1999, pp. 1030-1035.
David H. Epstein, et al. "Abuse liability, behavioral pharmacology, and physical-dependence potential of opioids in humans and laboratory animals: lessons from tramadol" Biol Psychol. vol. 73, 1st Edition Jul. 2006, pp. 90-99.
Stefan Grond, et al. "Clinical Pharmacology of Tramadol" Clin Pharmacokinet vol. 43, 13th Edition, 2004, pp. 879-923.
C. Rhoda Lee, et al. "Tramadol A preliminary Review of its Pharmacodynamic and Pharmacokinetic Properties, and Therapeutic Potential in Acute and Chronic Pain States" Drugs vol. 46 ,2nd Edition, 1993, pp. 313-340.

Lesley J. Scott, et al. "Tramadol A Review of its Use in Perioperative Pain" Drugs vol. 60 1st Edition, Jul. 2000, pp. 139-176.
S. M. Abdel-Rahman, PharmaD, et al. "Concordance between Tramadol and Dextromethorphan Parent/Metabolite Ratios: The Influence of CYP2D6 and Non-CYP2D6 Pathways on Biotransformation" J Clin Pharmacol 2002, pp. 24-29.
Edgar H. Adams, ScD, et al. "A Comparison of the Abuse Liability of Tramadol, NSAIDs, and Hydrocodone in Patients with Chronic Pain" Journal of Pain and Symptom Management, vol. 31 No. 5 May 2006, pp. 465-476.
Jeffrey L. Apfelbaum, et al. "Postoperative Pain Experience: Results from a National Survey Suggest Postoperative Pain Continues to Be Undermanaged" Anest Analg, 2003, vol. 97, pp. 534-540.
Yalda H. Ardakani, et al. "Pharmacokinetics of Tramadol and its Three Main Metabolites in Healthy Male and Female Volunteers" Biopharm, Drug Dispos vol. 28, 2007, pp. 527-534.
Sebnem Atici, et al. "Opioid Neurotoxicity: Comparison of Morphine and Tramadol in an Experimental Rat Model" Intern J Neuroscience, vol. 114, 2004, pp. 1001-1011.
Sebnem Atici, et al. "Liver and kidney toxicity in chronic use of opioids: An experimental long term treatment model" J. Biosci, vol. 30, 2nd Edition, Mar. 2005, pp. 245-252.
H. Barth, et al. "Anaphylactoid reactions and histamine release do not occur after application of the opiod tramadol" Agents and Actions, vol. 20, 1987, pp. 310-313.
Mauro Bianchi, et al. "Effects of tramadol on experimental inflammation" Fundam. Clin. Pharmacol vol. 13, 1999, pp. 220-225.
Mauro Bianchi, et al. "The Levels of Tramadol and its M1 Metabolite in the Plasma, Cerebrospinal Fluid, and Midbrain Following Acute Tramadol Administration in Rats" Analgesia vol. 6, 2002, pp. 39-42.
Caldolor Describing Information, Jun. 2009.
M.A. Campanero, et al. "High performance Liquid Chromatographic Assay for Simultaneous Determination of Tramadol and Its Active Metabolite in Human Plasma. Application to Pharmacokinetic Studies" Chromatographia vol. 48, Oct. 1998, pp. 555-560.
Sanzio Candeletti, et al. "Effects of Prolonged Treatment With the Opiate Tramadol on Prodynorphin Gene Expression in Rat CNS" Journal of Molecular Neuroscience vol. 30, 2006, pp. 341-347.
MS Cepeda, et al. "Tramadol for osteoarthritis (Review)" The Cochrane Collaboration®, 2009, pp. 1-32.
R.J. Christopher, et al. "Pharmacokinetics of (+)-Tramadol and (−)—Tramadol Enantiomers in Wistar Rats Following Single or Multiple Oral Dosing of Racemic Tramadol" Pharmaceutical Research An Official Journal of the American Association of Pharmaceutical Scientists, vol. 12, No. 9, Sep. 1995 PPDM: 8031.
J. Chrubasik, et al. "Intravenous tramadol for post-operative pain-comparison of intermittent dose regimens with and without maintenance infusion" European Journal of Anesthesiology vol. 9, 1992, pp. 23-28.
Theodore J. Cicero PhD, et al. "Rates of abuse of tramadol remain unchanged with the introduction of new branded and generic products: results of an abuse monitoring system" Pharmacoepidemiology and Drug Safety vol. 14, 2005, pp. 851-859.
C. Luthy Collart, et al. "Partial inhibition of tramadol antinociceptive effect by naloxone in man" Proceedings of the British Pharmacological Society Clinical Pharmacology Section, Sep. 1992, pp. 72.
M. Cossmann, et al. "Tolerance and Safety of Tramadol Use Results of International Studies and Data From Drug Surveillance" Drugs, vol. 53, Suppl. 2, 1997, pp. 50-62.
William J. Dana, et al. "Tramadol: A Step-2 Analgesic for Chronic Pain" The Cancer Bulletin, vol. 47, No. 6, 1995, pp. 511-514.
Pierre Dayer, et al. "The Pharmacology of Tramadol" Drugs, vol. 47, Suppl. 1, 1994, pp. 3-7.
Pierre Dayer, et al. "The Pharmacology of Tramadol" Drugs, vol. 53, Suppl. 2, 1997, pp. 18-24.
Koen De Decker, et al. "Fatal intoxication due to tramadol alone, Case report and review of the literature" Forensic Science International vol. 175, 2008, pp. 79-82.
B. Driessen, et al. "Interaction of the central analgesic, tramadol, with the uptake and release of 5-hydroxytryptamine in the rat brain in vitro" Br. J. Pharmacol, vol. 105, 1992, pp. 147-151.

(56) References Cited

OTHER PUBLICATIONS

B. Driessen, et al. "Effects of the central analgesic tramadol on the uptake and release of noradrenaline and dopamine in vitro" Br. J. Pharmacol, vol. 108, 1993, pp. 806-811.

S. Ellmauer, et al. "Various Opioids in Cardiovascular Risk Patients, Comparative Study on Central and Peripheral Hemodynamic Side Effects" Anaesthesist, vol. 43, 1994, pp. 743-749.

David H. Epstein, et al. "Abuse liability, behavioral pharmacology, and physical-dependence potential of opioids in humans and laboratory animals: Lessons from tramadol" Biological Psychology, vol. 73, 2006, pp. 90-99.

S. Elracin, et al. "Metabolism of Tramadol in Man and Animals" Naunyn-Schmiedeberg's Arch Pharmacol, vol. 313, Suppl: R51, 1980, pp. 202.

Davide Franceschini, et al. "Effect of Acute and Chronic Tramadol on [3H]-Norepinephrine-Uptake in Rat Cortical Synaptosomes" Prog. Neuro-Psychopharmacol & Biol. Psychiat., vol. 23, 1999, pp. 485-496.

E. Frankus, et al. "Separation of Isomers, Structural Elucidation, and Pharmacological Characterization of 1-(m-Methoxyphenyl)-2-(dimethylaminomethyl)cyclohexan-1-ol" Arzneim.-Forsch./Drug Res. 28 (1), Issue 1a, 1978, pp. 1-29.

E. Friderichs, et al. "Pharmalogical Studies on Analgesia, and Development of Dependence on and Tolerance of Tramadol, a Potent Analgesic" Arzneim.-Forsch./Drug Res. 28 (1), Issue 1a, 1978, pp. 1-29.

E. Friderichs, et al. "Contribution of Both Enantiomers to Antinociception of the centrally acting analgesic tramadol", Naunyn-Schmiedeberg's Archives of Pharmacology, vol. 346, 1992, pp. 82.

Siew Hua Gan, et al. "Impact of CYP2D6 Genetic Polymorphism on Tramadol Pharmacokinetics and Pharmacodynamics" Mol Diag Ther, vol. 11, 2007, pp. 171-181.

Maria J. Garrido, et al. "Modeling of the In Vivo Antinociceptive Interaction between an Opioid Agonist, (+)-O-Desmethyltramadol, and a Monoamine Reuptake Inhibitor, (−)-O-Desmethyltramadol, in Rats" The Journal of Pharmacology and experimental therapeutics, vol. 295. pp. 352-359.

Maria J Garrido, et al. "Pharmacokinetic/Pharmacodynamic Modeling of the Antinociceptive Effects of (+)-Tramadol in the Rat: Role of Cytochrome P450 2D Activity" The Journal of Pharmacology and experimental therapeutics, vol. 305, 2003, pp. 710-718.

Christiane Gasse, et al. "Incidence of First-Time Idiopathic Seizures in Users of Tramadol" Pharmacotherapy, vol. 20, 2000, pp. 629-634.

C. Gillen, et al. "In vitro and in vivo studies on the u-opioid-agonism and analgesic effect of tramadol metabolites" Society for neuroscience, vol. 25, 1999, pp. 680.4.

Clemens Gillen, et al. "Affinity, potency and efficacy of tramadol and its metabolites at the cloned human u-opioid receptor" Naynyn-Schmiedeberg's Arch Pharmacol, 2000, pp. 116-121.

Pietro Giusti, et al. "Effect of acute and chronic tramadol on [3H]-5-HT uptake in rat cortical synaptosomes" British Journal of Pharmacology, 1997, pp. 302-306.

Edwin Goldenthal, et al. "A compilation of LD50 Values in Newborn and Adult Animals" Toxicology and applied pharmacology, vol. 18, 1971, pp. 185-207.

Stefan Grond, et al. "Analgesic efficacy and safety of tramadol enantiomers in comparison with the racemate: a randomized, double-blind study with gynaecological patients using intravenous patient-controlled analgesia" Pain, vol. 62, 1995, pp. 313-320.

Stefan Grond, et al. "Serum Concentrations of tramadol enantiomers during patient-controlled analgesia" J Clin Pharmacol, vol. 48, 1999, pp. 254-257.

Stefan Grond, et al. "Clinical Pharmacology of Tramadol" Clin Pharmacokinet, vol. 43, 2004, pp. 879-923.

Michael K. Herbert, et al. "The enantiomers of tramadol and its major metabolite inhibit peristalsis in the guinea pig small intestine via differential mechanisms" BMC Pharmacology, 2007, pp. 1-11.

Elliot V. Hersh, et al. "Adverse Drug Interactions Involving Common Prescription and Over-the-Counter Analgesic Agents" Clinical Therapeutics, vol. 29, 2007, pp. 2477-2497.

Robert-Jan M. Houmes, MD, et al. "Efficacy and Safety of Tramadol Versus Morphine for Moderate and Severe Postoperative Pain With Special Regard to Respiratory Depression" Anesth Analg, vol. 74, 1992, pp. 510-514.

Liu Hui-Chen, et al. "Pharmacokinetics of the Enantiomers of trans-Tramadol and Its Active Metabolite, trans-O-Demethyltramadol, in Healthy Male and Female Chinese Volunteers" Chirality, vol. 16, 2004, pp. 112-118.

Mouna Kanaan, et al. "Uptake/Efflux Transport of Tramadol Enantiomers and O-Desmethyl-Tramadol:Focus on P-Glycoprotein" Nordic Pharmacological Society, Basic & Clinical Pharmacology & Toxicology, vol. 105, pp. 199-206.

Valrie Kayser, et al. "Effects of the analgesic agent tramadol in normal and arthritic rats: comparison with the effects of different opioids, including tolerance and cross-tolerance to morphine" European Journal of Pharmacology, vol. 195, 1991, pp. 37-45.

Valerie Kayser, et al. "Evidence for a noradrenergic component in the antinociceptive effect of the analgesic agent tramadol in an animal model of clinical pain, the arthritic rat" European Journal of Pharmacology, vol. 224, 1992, pp. 83-88.

Julia Kirchheiner, MD, et al. "Effects of the CYP2D6 Gene Duplication on the Pharmacokinetics and Pharmacodynamics of Tramadol" Journal of Clinical Psychopharmacology, vol. 28, 2008, pp. 78-83.

Aysel Kucuk, et al. "Investigation of the pharmacokinetics and determination of tramadol in rabbit plasma by a high-performance liquid chromatography-diode array detector method using-liquid extraction" Journal of Chromatography, vol. 816, 2005, pp. 203-208.

Butch KuKanich, et al. "Pharmacokinetics of tramadol and its active metabolite O-Desmethyltramadol following intravenous and oral administration of tramadol and intravenous o-desmethyltramadol" ACVIM Abstracts, 2004, pp. 176.

Butch KuKanic, et al. "Pharmacokinetics of tramadol and the metabolite O-desmethyltramadol in dogs" J. vet. Pharmacol. Therap. vol. 27, 2004, pp. 239-246.

Lagler, et al. "Acute Toxicity" Arzneim.-Forsch./Drug Res. vol. 28, 1978, pp. 164-172.

Josephine Lai, et al. "Tramadol, M1 metabolite and enantiomer affinities for cloned human opioid receptors expressed in transfected HN9.10 neuroblastoma cells" European Journal of Pharmacology, vol. 316, pp. 369-372.

C. Rhoda Lee, et al. "Tramadol A Preliminary Review of its Pharmacodynamic and Pharmacokinetic Properties, and Therapeutic Potential in Acute and Chronic Pain States" Drugs, vol. 46, 1993, pp. 313-340.

Klaus A. Lehmann, et al. "Postoperative Patient-Controlled Analgesia with Tramadol:Analgesic Efficacy and Minimum Effective Concentrations" The Clinical Journal of Pain, 1990, pp. 212-220.

S. Liao, et al. "The Effect of Food on the Bioavailability of Tramadol" Official Journal of the American Association of Pharmaceutical Scientists, 1992, pp. 8207.

W. Lintz, et al. "Metabolism of Tramadol in Man and Animal" Arzneim.-Forsch./Drug Res. vol. 31, 1981, pp. 1-42.

W. Lintz, et al. "Bioavailability of Enteral Tramadol Formulations" Arzneim.-Forsch./Drug Res. vol. 36, 1986, pp. 1278-1283.

W. Lintz, et al. "Pharmacokinetics of Tramadol and Bioavailability of Enteral Tramadol Formulations" Arzneim.-Forsch./Drug Res. vol. 36, 1998, pp. 889-899.

W. Lintz, et al. "Bioavailability of Enternal Tramadol Formualtions" Arzneim.-Forsch./Drugs Res. vol. 36, 1986, pp. 1278-1283.

Yong-min Liu, et al. "Effect of tramadol on immune responses and nociceptice thresholds in a rat model of incisional pain" J Zhejiang Univ Sci B, 2008, pp. 895-902.

TR Lubenow MD, et al. "Analgesic, Hemodynamic and respiratory responses to intrathecal tramadol in dogs" Abstracts of Scientific Papers 1995 Annual Meeting American Society of Anesthesiologists, 1995, pp. A822.

Anshu Manocha, et al. "On the mechanism of anticonvulsant effect of tramadol in mice" Pharmacology: Biochemistry and Behavior 82, 2005, pp. 74-81.

(56) References Cited

OTHER PUBLICATIONS

Kathy A Marquardt, et al. "Tramadol Exposures Reported to State-wide Poison Control System" The annals of Pharmacotherapy, vol. 39, Jun. 2005, pp. 1039-1044.
T. Matthiesen, et al. "The experimental toxicology of tramadol:an overview" Toxicology Letters, vol. 95, 1998, pp. 63-71.
Antonia Mattia, et al. "Characterization of the Unusual Antinociceptive Profile of Tramadol in Mice" Drug Development Research, vol. 28, 1993, pp. 176-182.
Leena H. Mildh, et al. "Effects of Tramadol and Meperidine on Respiration, Plasma Catecholamine Concentrations, and Hemodynamics" Journal of Clinical Anesthesia, vol. 11, 1999, pp. 310-316.
T. Murano, et al. "Studies of Dependence on Tramadol in Rats" Arzneim.-Forsch./Drug Res., vol. 28, 1978, pp. 152-158.
D.B. Murphy, et al. "A comparison of the effects of tramadol and morphine on gastric emptying in man" Anaesthesia, vol. 52, 1997, pp. 1212-1229.
Etsuko Nagaoka, MD, et al. "Tramadol Has No Effect on Cortical Renal Blood Flow—Despite Increased Catecholamine Levels—in Anesthetized Rats: Implications for Analgesia in Renal Insufficiency" Anesth Analg, vol. 94, 2002, pp. 619-625.
Gabriela Nosalova, et al. "Relationship between the antitussic and analgesic activity of substances" Acta Physiologica Hungarica, vol. 77, 1991, pp. 173-178.
Alec B. O'Connor, MD, et al. "Treatment of Neuropathic Pain: An Overview of Recent Guidelines" Guidelines for Treatment of Neuropathic Pain, 2009, pp. S22-S32.
D.S. Ogunleye, et al. "Investigation of racial variations in the metabolism of tramadol" European Journal of Drug Metabolism and Pharmacokinetics, vol. 26, 2001, pp. 95-98.
G. Osterloh, et al. "General Pharmacological Studies on Tramadol, a Potent Analgesic" Arzneim.-Forsch./Drug Res., vol. 28, 1978, pp. 1-57.
Mehmet Ozalevli, MD, et al. "Comparison of morphine and tramadol by patient-controlled analgesia for postoperative analgesia after tonsillectomy in children" Pediatric Anesthesia, vol. 15, 2005, pp. 979-984.
W.D. Paar, et al. "Polymorphic CYP2D6 mediates O-demethylation of the opioid analgesic tramadol" Eur J Clin Pharmacol, vol. 53, 1997, pp. 235-239.
Ridhi Parasrampuria, et al. "Route-Dependent Stereoselective Pharmacokinetics of Tramadol and Its Active O-Demethylated Metabolite in Rats" Enantioselective Pharmacokinetics of Tramadol, 2007, pp. 190-196.
Lars Paulsen, MD, et al. "The hypoalgesic effect of tramadol in relation to CYP2D6" Clinical Pharmacology & Therapeutics, Dec. 1996, pp. 636-644.
Kenzie L. Preston, et al. "Abuse potential and pharmacological comparison of tramadol and morphine" Drugs and Alcohol Dependence, vol. 27, 1997, pp. 7-17.
Emilio Garcia Quetglas, et al. "Stereoselective Pharmacokinetic Analysis of Tramadol and its Main Phase I Metabolites in Healthy Subjects after Intravenous and Oral Administration of Racemic Tramadol" Biopharm. Drugs Dispos, vol. 28, 2007, pp. 19-33.
Robert B. Raffa, et al. "Opioid and Nonopioid Components Independently Contribute to the Mechanism of Action of Tramadol, an 'Atypical' Opioid Analgesic" The Journal of Pharmacology and Experimented Therapeutics, vol. 200, 1992, pp. 275-285.
Shu-Feng Zhou, et al. "Polymorphism of Human Cytochrome P450 2D6 and its Clinical Significance" Clin Pharmacokinet, vol. 48, 2009, pp. 689-723.
Robert B. Raffa, et al. "Complementary and Synergistic Antinociceptive Interaction between the Enantiomers of Tramadol" The Journal of Pharmacology and Experimental Therapeutics, vol. 267, 1993, pp. 331-340.
Robert B. Raffa, et al. "Basic pharmacology relevant to drug abuse assessment: tramadol as example" Journal of Clinical Pharmacy and Therapeutics, vol. 33, 2008, pp. 101-108.
Juliana Montani Raimundo, et al. "In vitro and in vivo vasodilator activity of racemic tramadol and its enantiomers in Wistar rats" European Journal of Pharmacology, vol. 530, 2006, pp. 117-123.
James P. Rathmell, M.D., et al. "Acute Post-Surgical Pain Management :A critical Appraisal of Current Practice" Regional Anesthesia and Pain Medicine, Jul./Aug. 2006, pp. 1-41.
M.T. Rosenberg. "The role of tramadol ER in the treatment of chronic pain" Int J Clin Pract, vol. 63, Oct. 2009, pp. 1531-1543.
U. Rud, et al. "Postoperative Analgesia with Tramadol" Anaesthesist, vol. 43, 1994, pp. 316-321.
Paola Sacerdote, et al. "Effects of tramadol on immune responses and nociceptive thresholds in mice" Pain, vol. 72, 1997, pp. 325-330.
Paola Sacerdote, et al. "The Effects of Tramadol and Morphine on Immune Responses and Pain After Surgery in Cancer Patients" Anesth Analg, vol. 90, 2000, pp. 1411-1414.
Lesley J. Scott, et al. "Tramadol A Review of its Use in Perioperative Pain" Drugs, vol. 60, Jul. 2000, pp. 139-176.
S. Shadnia, et al. "Tramadol intoxication:a review of 114 cases" Human & Experimental Toxicology, vol. 27, 2008, pp. 201-205.
Hedayatollah Shirzad, et al. "Comparison of morphine and tramadol effects on phagocytic activity of mice peritoneal phagocytes in vivo" International Immunopharmacology, vol. 9, 2009, pp. 968-970.
M. Silvasti, et al. "Comparison of intravenous patient-controlled analgesia with tramadol versus morphine after microvascular breast reconstruction" European Journal of Anaesthesiology,vol. 17, 2000, pp. 448-455.
Raymond S. Sinatra, MD, et al. "Pain Management After Major Orthopaedic Surgery: Current Strategies and New Concepts" Journal of the American Academy of Orthopaedic Surgery, vol. 10, Mar./Apr. 2002, pp. 118-129.
Francois J. Singelyn, MD, et al. "Effects of Intravenous Patient-Controlled Analgesia with Morphine, Continuous Epidural Analgesia, and Continuous Three-in-One Block on Postoperative Pain and Knee Rehabilitation After Unilateral Total Knee Arthoplasty" The International Anesthesia Research Society, 1998, pp. 88-92.
Ondrej Slanar, et al. "Pharmacokinetics of tramadol is affected by MDR1 polymorphism C3435T", Eur J Clin Pharmacol vol. 63, 2007, pp. 419-421.
Stephen Southworth, M.D., et al. "A multicenter, randomized, double-blind, placebo-controlled trial of intravenous ibuprofen 400 and 800 mg every 6 hours in the management of postoperative pain" Clinical Therapeutics, vol. 31, Nov. 9, 2009, pp. 1922-1935.
Joe E Sprague, et al. "In Vivo Microdialysis and Conditioned Place Preferences Studies in Rats are Consistent With Abuse Potential of Tramadol" Synapse, vol. 43, 2002, pp. 118-121.
UM Stamer, et al. "Concentrations of Tramadol and O-desmethyltramadol Enantiomers in Different CYP2D6 Genotypes" Clinical Pharmacology & Therapeutics, vol. 82, 2007, pp. 41-47.
M Staritz, et al. "Effect of modern analgesic drugs (Tramadol, pentazocine, and buprenorphine) on the bile duct sphincter in man" Gut, vol. 27, 1986, pp. 567-569.
Vangala Subrahmanyam, et al. "Identification of Cytochrome P-450 Isoforms Responsible for Cis-Tramadol Metabolism in Human Liver Microsomes" Drug Metabolism and Disposition, vol. 29, 2001, pp. 1146-1155.
Adrienne R. Takacs. "Ancillary Approaches to Toxicokinetic Evaluations" Toxicologic Pathology, vol. 23, 1995, pp. 179-186.
Micaela Tjaderborn, et al. "Fatal unintentional intoxications with tramadol during 1995-2005" Forensic Science International vol. 173, 2007, pp. 107-111.
Company Core Product Profile, Tramadol, 2008, pp. 1-11.
Ultram (tramadol hydrochloride) Tablets, Full Prescribing Information, 2009.
Marta Valle, et al. "Pharmacokinetic-Pharmacodynamic Modeling of the Antinociceptive Effects of Main Active Metabolites of Tramadol, (+)-O-Desmethyltramadol and (−)-O-Desmethyltramadol, in Rats" The Journal of Pharmacology and Experimental Therapeutics, vol. 293, 2000, pp. 646-653.

(56) References Cited

OTHER PUBLICATIONS

M.D. Vickers, et al. "Comparison of tramadol with morphine for post-operative pain following abdominal surgery" European Journal of Anaesthesiology, vol. 12, 1995, pp. 265-271.

W. Vogel, et al. "Effect of Tramadol on Respiration and Circulation" Arnzeim.-Forsch./Drug Res., vol. 28, 1978, pp. 183-186.

Katriina Vuolteenaho, et al. "Non-Steroidal Anti-Inflammatory Drugs, Cyclooxygenase-2 and the Bone Healing Process" Basic & Clinical Pharmacology & Toxicology, vol. 102, pp. 10-14.

Clive H. Wilder-Smith, et al. "The analgesic tramadol has minimal effect on gastrointestinal motor function" Br J Clin Pharmacol, vol. 43, 1997, pp. 71-75.

Clive H. Wilder-Smith, et al. "Effects of Morphine and Tramadol on Somatic and Visceral Sensory Function and Gastrointestinal Motility after Abdominal Surgery" Anesthesiology, vol. 91, 1999, pp. 639-647.

Clive H. Wilder-Smith, et al. "Effect of Tramadol and Morphine on Pair and Gastrointestinal Motor Function in Patients with Chronic Pancreatitis" Digestive Diseases and Sciences, vol. 44, Jun. 1999, pp. 1107-1116.

W.N. Wu, et al. "Metabolism of the analgesic drug, tramadol hydrochloride, in rat and dog" Xenobiotica, vol. 31, 2001, pp. 423-441.

W.N. Wu, et al. "In Vitro Metabolism of the Analgesic Agent, Tramadol-N-oxide, in Mouse, Rat, and Human" European Journal of Drug Metabolism and Pharmacokinetics, vol. 27, 2002, pp. 193-197.

W.N. Wu, et al. Metabolism of the analgesic drug ULTRAM® (tramadol hydrochloride) in humans: APO-MS and MS/MS characterization of metabolites Xenabiotica, vol. 32, 2002, pp. 411-425.

W.N. Wu, et al. "Metabolism of two analgesic agents, tramadol-n-oxide and tramadol, in specific pathogen-free and axenic mice" Xenobiotica, vol. 36, Jun. 2006, pp. 551-565.

Hiroyuki Yamamoto, et al. "A Study on Teratogenicity of Both CG-315 and Morphine in Mice and Rats" Oyo Yakuri (Pharmacometrics) vol. 6, 1972, pp. 1055-1069.

T. Yanagita, et al. "Drug Dependence Potential of 1-(m-Methoxyphenyl)-2-(dimethylaminomethyl)-cyclohexan-1-ol Hydrochlroide (Tramadol) Tested in Monkeys" Arnzeim.-Forsch./Drug Res. vol. 28, 1978, pp. 158-163.

Prescribing Information Trambax™ (Tramal Hydrochloride Injection), pp. 1.

UpKAR Tramadol 50mg/ml Solution for Injection/Infusion, Technical Leaflet, Beacon Pharmaceuticals pp. 19-23.

Tramal® Solution for Injection pp. 1.

\* cited by examiner

Figure 1. Geometric Mean Steady-State Tramadol Concentrations Using Compartmental Model Analysis

INTRAVENOUS ADMINISTRATION OF TRAMADOL

This application is a continuation of U.S. application Ser. No. 15/976,503 filed May 10, 2018, which is a continuation of U.S. application Ser. No. 15/612,665 filed Jun. 2, 2017 (now U.S. Pat. No. 9,968,551), which is a continuation of U.S. application Ser. No. 15/163,111 filed May 24, 2016 (now U.S. Pat. No. 9,693,949), which claims priority to U.S. Provisional Application No. 62/271,107 filed on Dec. 22, 2015, the disclosures of which are hereby incorporated by reference herein.

This application claims priority to U.S. Provisional Application No. 62/271,107, filed on Dec. 22, 2015; the disclosure of which is hereby incorporated by reference herein.

BACKGROUND OF THE INVENTION

Tramadol is a centrally acting synthetic analgesic with a dual mechanism of action attributed to the racemic form of the drug, comprised of μ-opioid activity (binding to μ-opioid receptors and monoamine (serotonin and noradrenalin) reuptake inhibition. Tramadol is an analog of the phenanthrene group of opium alkaloids, which includes morphine and codeine, and is structurally related to these opioids (Grond S and Slabotzi A. Clinical pharmacology of tramadol. Clin Pharmacokinet. 2004; 43:879-923). Like codeine, there is a substitution of the methyl group on the phenol ring that imparts a relatively weak affinity for opioid receptors. (+)-Tramadol is a more potent inhibitor of serotonin uptake, while (−)-tramadol is a more potent inhibitor of norepinephrine uptake. The opioid-like activity of tramadol derives from low affinity binding of the parent compound to μ-opioid receptors and higher affinity binding of its main metabolite. Tramadol affinity to μ opioid receptors is about 10 times weaker than codeine 60 times weaker than dextropropoxyphene and 6,000 times weaker than morphine. The active metabolite O-desmethyltramadol (M1) possesses a higher affinity to the μ opioid receptor than tramadol and displays analgesic activity (Leppert W, 2009).

Tramadol was originally developed by the German pharmaceutical company Grünenthal GmbH in the late 1970s and is marketed globally under the trade names TRAMAL® and others outside of the United States. The approved doses of tramadol are 50 mg or 100 mg administered as a slow injection every 4-6 hours (Tramadol Core Product Label, 2008). In the U.S., tramadol is approved by the Food and Drug Administration (FDA) and marketed as an oral capsule/tablet for moderate to moderately severe pain in adults. Tramadol was first approved in the US in April 1995 under the trade name, ULTRAM® (Ortho-McNeil-Janssen Pharmaceuticals, Inc). Tramadol is also an active agent in an extended release product, Ultram® ER, and a combination product with acetaminophen, ULTRACET®. In the US, tramadol is only available as immediate release tablets or extended release tablets. Other tramadol formulations approved in several countries include tablets, capsules, effervescent powders, and suppositories (Grond and Sablotzki, 2004; Rosenberg, 2009). The approved intravenous regimen in India is an initial injection of 50 mg infusion over 2-3 min, followed by 50 mg every 10-20 minutes if necessary up to 250 mg for the first hour. Maintenance doses are 50-100 mg every 4-6 hours with a maximum dose of 600 mg daily (Tramadol, CIMS Data_India).

Postoperative pain management with tramadol has effectively utilized a variety of delivery methods, including bolus injection (IV or IM), continuous infusions and patient controlled analgesia (PCA) pumps, and various combinations of these methods (Scott and Perry, 2000; Grond and Sablotzki, 2004). The potency ratio of IV tramadol to IV morphine is approximately 1:10, while the ratio for IV fentanyl is 1:979 (Grond and Sablotzki, 2004).

The "on-demand" analgesic efficacy of tramadol was compared to morphine in the 24-hour post-operative period for 523 patients undergoing abdominal surgery (Vickers M D, Paravicini D. Comparison of tramadol with morphine for post-operative pain following abdominal surgery. Eur J Anesthesiol. 1995; 12: 265-71). Patients who reported post-operative pain received an initial dose (either tramadol 100 mg or morphine 5 mg i.v.) and, if necessary, repeat i.v. or i.m. doses of tramadol 50 mg or morphine 5 mg on demand over the first 90 minutes. Further doses up to a total of 400 mg tramadol or 40 mg morphine could then be given after 90 minutes up to 24 hours after the first dose of study medication. The primary efficacy parameter was the responder rate (no or slight pain) within the first 90 minutes of treatment. Responder rates were 72.6% for tramadol and 81.2% for morphine, which were statistically equivalent and within the predefined range of ±10%. Mean cumulative doses were 188.2 mg for the first 90 minutes and 157.1 mg for the subsequent 22.5 hours in the tramadol group and 13.9 mg and 18.4 mg, respectively in the morphine group. The main adverse events were gastrointestinal in both groups, with mild nausea, dry mouth, vomiting, dyspepsia and hiccups reported most frequently.

The analgesic effect of continuous infusion of tramadol was compared to repeated bolus administration in 135 patients undergoing abdominal surgery (Rud U, Fischer M V, Mewes R, Paravcini D., "Postoperative Analgesie mit Tramadol Kontinuierliche Infusion versus repetitive" (Post-operative analgesia with tramadol. Continuous infusion versus repetitive bolus administration), Bolusgabe Anaesthesist. 1994; 43:316-321. (German)). Patients were randomized at the time of the first request for pain treatment. All patients received a loading dose of tramadol 100 mg i.v. Subsequent treatment was administered in a double-blind manner; patients in the infusion group were given a continuous infusion of tramadol 12 mg/h for 24 hours, whereas patients in the bolus group received placebo infusion. In both groups, additional bolus doses of tramadol 50 mg i.v. were given as required. Pain relief was monitored by means of a visual analog scale (VAS) up to 6 hours after surgery. The number of additional boluses and the amount of tramadol administered at 6 hours and 24 hours was also used to assess analgesic efficacy. More patients in the infusion group assessed their pain relief as excellent or good compared to the bolus group (76.5% vs 65.6%). Only a few patients complained of insufficient analgesia, with more patients in the bolus group reporting inadequate pain relief than in the infusion group (7.5% vs 4.4%). A higher percentage of patients in the bolus group required two or more boluses compared to the infusion group (59.7% vs 30.8%). After 6 hours, the average tramadol consumption was 223.5±53.7 mg in the infusion group and 176.6±63.1 mg in the bolus group (p≤0.05). After 24 hours, tramadol consumption was 449.5±66.0 mg and 201.6±83.9 mg (p≤0.001), respectively. Adverse events were reported by 25% of patients in both groups, with no significant differences and no patient terminated the trial for an adverse event. There were no significant effects on blood pressure or heart rate. The authors concluded that continuous infusion was more effective in the first 6 hours after surgery. However, excess consumption by the infusion group was statistically greater than the bolus group at both 6 hours and 24 hours post-surgery.

Intermittent bolus and continuous infusion of tramadol were evaluated in a postoperative study of 35 patients undergoing major abdominal gynecologic surgery (Chrubasik J, Buzina M, Schulte-Monting J, Atanassoff P, Alon E. Intravenous tramadol for post-operative pain-comparison of intermittent dose regimens with and without maintenance infusion. Eur J Anaesthesiol. 1992; 9:23-28). The study was randomized and double-blind and used tramadol infusion 15 mg/h or saline. Additional boluses of tramadol 100 mg were given as requested. The patients in the infusion group required 60% less tramadol on demand (p<0.01) and had better pain relief (p<0.05), as assessed by VAS, than the group that received the saline infusion. Total tramadol consumption, however, was about 30% higher in the infusion group (p<0.05) and was associated with and increased incidence of minor adverse events. Tramadol was ineffective as pain relief within 2 hours of the beginning of treatment in 6% of the infusion group and 20% of the bolus group. Thus, continuous infusion was preferred to "on-demand" bolus treatment.

A meta-analysis of nine randomized, controlled trials indicated that tramadol was as effective as other opioids, including morphine, for control of postoperative pain (Scott and Perry, 2000). Pain in these patients was described as moderate to severe, with initial postoperative pain reported as >60 on a 100-point visual analog scale or as moderate or severe on a 4- or 5-point verbal response scale. The first dose of analgesia was administered when patients reported moderate to severe pain in the postoperative setting. Studies that did not adequately record baseline pain severity or response to analgesia, were not randomized or controlled or contained less than 45 patients were excluded from the meta-analysis. Tramadol, administered in a dose titrated to pain response and via either IV (intravenous) or IM (intramuscular) intermittent injection, reduced pain intensity by 46.8% to 57.6% after 4 to 6 hours compared to 69.8% for morphine and 25.6% to 51.3% for pentazocine. Efficacy of tramadol was maintained for the duration of the studies, which were ≤72 hours, and was comparable to morphine or alfentanil. However, the onset of action of tramadol was slower than morphine, as assessed by measurements approximately 3 hours after the first dose. There were no significant differences in the percentage of patients treated with tramadol or morphine and who also required rescue medication. The patient global response and physician global response were similar for tramadol and for other opioids.

Tramadol injection (IV/IM/SC) is approved and used for the management of moderate to severe acute postoperative pain in several regions, including Europe, India and Australia/New Zealand (however, this dosage form is not available in the USA). Tramadol ampoules or vials for IV, IM and SC administration and preservative-free solutions for injection by the various spinal routes (epidural, intrathecal, caudal, etc.) are available forms in these regions. Tramadol formulations approved in several countries include, tablets, capsules, effervescent powders, and suppositories (Grond and Sablotzki, 2004; Rosenberg, 2009).

There is extensive data demonstrating that tramadol use is not associated with the classical opioid side effects seen with more potent opioids. There are numerous reports of the safety and efficacy of tramadol (Lee et al., 1993; Scott and Perry, 2000; Grond and Sablotzki, 2004). The most common adverse events of tramadol administration are nausea, dizziness, headache, somnolence, sweating, fatigue, constipation, dry mouth and vomiting. However, tramadol use, particularly with high doses, has been associated with seizures, and the risk of seizures is increased in the presence of drugs that reduce seizure threshold, head trauma or prior history of seizures.

Patients undergoing surgery, for example, total knee arthroplasty (TKA) and total hip arthroplasty (THA), typically demonstrate a need for short-term analgesia, which is critical for earlier mobilization and rehabilitation. In this setting, assuring adequate pain relief without providing extensive medical oversight required for some methods of treatment (such as neuraxial anesthesia) and prevention of effects such as opiate-induced respiratory depression and dependency would be highly beneficial (Sinatra et al., 2002).

The goal of post-surgical pain management is twofold: i) to provide a quick onset of analgesic or pain relief and ii) to reduce or modulate the quality and intensity of pain that a patient experiences in the post-surgical period. While current treatments for management of post-surgical acute pain are useful, there is a need for improved methods for treating post-surgical acute pain.

OBJECTS AND SUMMARY OF THE INVENTION

It is an object of the present invention to provide a method of treating pain in human patients.

It is a further object of the present invention to provide a method of treating pain in human patients who are unable to take oral medications, such as in a post-operative condition.

It is a further object of the present invention to provide a method of treating pain in human patients that takes advantage of the faster onset of intravenous administration of tramadol while providing additional benefits not available via current methodologies of tramadol intravenous administration.

It is another object of the present invention to provide a method of providing a safe and effective alternative injectable analgesic for use in the acute postoperative setting.

It is another object of the present invention to provide a method for treating pain in, e.g., the acute postoperative setting which is or may be opioid-sparing.

It is another object of the present invention to provide a method for treating pain with intravenous tramadol in human patients in a manner that may or does reduce side-effects (such as, e.g., nausea, vomiting or seizure).

It is a further object of the present invention to provide a method of treating pain with a drug and dosing regimen that provides a positive benefit-risk profile, and which addresses an unmet medical need for the management of acute post-operative pain.

In accordance with the above objects and others, the present invention is directed in part to a method of administering tramadol for treating pain via an intravenous dosing regimen comprising intravenously administering a first dose of tramadol to a human patient in an amount from about 45 mg to about 80 mg; intravenously administering a second dose of tramadol to the human patient in an amount from about 45 mg to about 80 mg at a time from about 2 to about 3 hours after the first dose; intravenously administering a third dose of tramadol to the human patient in an amount from about 45 mg to about 80 mg at a time from about 2 to about 3 hours after the second dose; and thereafter intravenously administering from about 45 mg to about 80 mg tramadol at dosage intervals from about 4 to about 6 hours, until the patient no longer requires treatment with tramadol, such that the intravenous dosing regimen provides a Cmax and AUC of tramadol which is similar to the Cmax and AUC of an oral dose of 100 mg tramadol HCl given every 6 hours at steady-state. In certain preferred embodiments, each dose of tramadol is about 50 mg, or about 48 mg, or about 62 mg, or about 75 mg. In certain preferred embodiments, the dosing regimen further comprises administering additional doses of tramadol intravenously such that a daily dose from about 315 mg to about 560 mg tramadol is intravenously administered over the first 24 hours of administration, and a daily dose from about 270 mg to about 480 mg tramadol is administered thereafter.

In certain preferred embodiments, each dose of tramadol is about 50 mg, the second dose is administered about 2 hours after the first dose, the third dose is administered about 2 hours after the second dose, and the tramadol is dosed on an every 4 hour basis thereafter. In other preferred embodiments, each dose of tramadol is about 50 mg and is administered every 4 hours after the second (or third dose) of intravenous tramadol.

In certain other preferred embodiments, each dose of tramadol is about 75 mg, the second dose is administered about 3 hours after the first dose, the third dose is administered about 3 hours after the second dose, and the tramadol is dosed on an every 6 hour basis thereafter.

In other preferred embodiments, each dose of tramadol is from about 45 mg to about 55 mg, the second dose is administered about 2 hours after the first dose, the third dose is administered about 2 hours after the second dose, and the tramadol is dosed on an every 4 hour basis thereafter.

In other preferred embodiments, each dose of tramadol is from about 60 mg to about 80 mg, the second dose is administered about from about 3 to about 4 hours after the first dose, the third dose is administered about 3 to about 4 hours after the second dose, and the tramadol is dosed on an every 6 hour basis thereafter.

The present invention is also directed in part to a method of administering tramadol for treating pain via an intravenous dosing regimen comprising intravenously administering a first dose of tramadol to a human patient in an amount of about 45 mg to about 55 mg; intravenously administering a second dose of tramadol to the human patient in an amount from about 45 mg to about 55 mg at about 2 hours after the first dose; intravenously administering a third dose of tramadol to the human patient in an amount from about 45 mg to about 55 mg at about 2 hours after the second dose; and thereafter intravenously administering from about 45 mg to about 55 mg tramadol at dosage intervals of about 4 hours, until the patient no longer requires treatment with tramadol. In certain preferred embodiments, the dose administered each time is about 50 mg. In certain preferred embodiments of this method, the blood plasma levels of the parent compound (e.g., Cmax and steady-state concentration) are almost reached at about 4 hours after the first intravenous dose of 50 mg tramadol. In certain preferred embodiments, the method comprises administering from about 315 mg to about 385 mg tramadol intravenously over an initial 24 hour period of treatment, and a daily dose from about 270 mg to about 330 mg daily thereafter.

The present invention is further directed to a method of administering tramadol for treating pain via an intravenous dosing regimen comprising intravenously administering a first dose of tramadol to a human patient in an amount of about 70 mg to about 80 mg; intravenously administering a second dose of tramadol to the human patient in an amount from about 70 mg to about 80 mg at about 3 hours after the first dose; intravenously administering a third dose of tramadol to the human patient in an amount from about 70 mg to about 80 mg at about 3 hours after the second dose; and thereafter intravenously administering from about 70 mg to about 80 mg tramadol at dosage intervals of about 6 hours, until the patient no longer requires treatment with tramadol. In certain preferred embodiments, the dose administered each time is about 75 mg. In certain preferred embodiments of this method, the blood plasma levels of the parent compound (e.g., Cmax) are reached at about 6 hours after the first intravenous dose of 75 mg tramadol. In further preferred embodiments, the method further comprises administering from about 350 mg to about 400 mg tramadol intravenously over an initial 24 hour period of treatment, and a daily dose from about 270 mg to about 330 mg daily thereafter.

In certain preferred embodiments, the intravenous dosing regimens of the invention provide a Cmax and AUC of tramadol which is similar to the Cmax and AUC of an oral dose of 100 mg tramadol HCl given every 6 hours, at steady-state.

In certain preferred embodiments, the intravenous dosing regimens of the invention provide a Cmax of tramadol at steady-state that is from about 80% to about 125% of the Cmax provided at steady-state by a 100 mg oral dose of tramadol HCl given every 6 hours.

In certain preferred embodiments, the intravenous dosing regimens of the present invention provide an AUC of tramadol at steady-state that is from about 80% to about 125% of the AUC provided at steady-state by a 100 mg oral dose of tramadol HCl given every 6 hours.

In certain preferred embodiments, the intravenous dosing regimens of the invention provide a Cmax of the M1 metabolite of tramadol at steady-state that is from about 20% to about 125% (in certain embodiments from about 60% to about 75%), or from about 80% to about 125% of the Cmax of the M1 metabolite of tramadol at steady-state when the tramadol is administered as oral 100 mg tramadol HCl every 6 hours.

In certain preferred embodiments, the intravenous dosing regimens of the invention provide an AUC of the M1 metabolite of tramadol at steady-state which is from about from about 20% to about 125% (in certain embodiments from about 60% to about 75%), or from about 80% to about 125% of the steady-state AUC of the M1 metabolite of tramadol when the tramadol is administered as oral 100 mg tramadol HCl every 6 hours.

In certain embodiments of the intravenous dosing regimens of the invention, the intravenous dosing regimen provides a Cmax of tramadol at steady-state from about 80% to about 125% of about 676 ng/mL.

In certain embodiments of the intravenous dosing regimens of the invention, the intravenous dosing regimen provides a Cmax and/or AUC of the M1 metabolite of tramadol at steady-state which is from about 20% to about 125%, from about 60% to about 100%, or from about 80% to about 125% of about 125 ng/mL.

In certain preferred embodiments of the intravenous dosing regimens of the invention, the intravenous dosing regimen provides an $AUC_{24-48}$ (h*ng/mL) of tramadol which is from about 80% to about 125% of about 11,020 hr*ng/mL, or about 11,020 hr*ng/mL±2852. In certain preferred embodiments of the intravenous dosing regimens of the invention, the intravenous dosing regimen provides an $AUC_{0-24}$ (h*ng/mL) of tramadol which is from about 80% to about 125% of about 9520 hr*ng/mL, or about 9520 hr*ng/mL±2106. In certain preferred embodiments of the intravenous dosing regimens of the invention, the intravenous dosing regimen provides an $AUC_{0-48}$ (h*ng/mL) of tramadol which is from about 80% to about 125% of about 20,540 hr*ng/mL, or about 20,540 hr*ng/mL±4906.

In certain preferred embodiments of the intravenous dosing regimens of the invention, the intravenous dosing regimen provides a $AUC_{24\text{-}48}$ (h*ng/mL) of the M1 metabolite of tramadol which is from about from about 20% to about 125%, or from about 80% to about 125% of about 2002 hr*ng/mL, or about 2002 hr*ng/mL±514.9. In certain preferred embodiments of the intravenous dosing regimens of the invention, the intravenous dosing regimen provides a $AUC_{0\text{-}24}$ (h*ng/mL) of the M1 metabolite of tramadol which is from about from about 20% to about 125%, or from about 80% to about 125% of about 1425 hr*ng/mL, or about 1425 hr*ng/mL±405.4. In certain preferred embodiments of the intravenous dosing regimens of the invention, the intravenous dosing regimen provides a $AUC_{0\text{-}48}$ (h*ng/mL) of the M1 metabolite of tramadol which is from about from about 20% to about 125%, or from about 80% to about 125% of about 3427 hr*ng/mL, or about 3427 hr*ng/mL±889.9.

In preferred embodiments of the intravenous dosing regimens of the invention, each dose of tramadol is administered intravenously over a time period from about 10 minutes to about 20 minutes. In certain preferred embodiments, each dose of the tramadol is administered over a time interval of 15 (±2) minutes.

In certain preferred embodiments of the intravenous dosing regimens of the invention, the method further comprises administering a first dose of tramadol to the patient intra-operatively at wound closure, or from first demand of analgesia post-operatively, and administering said further doses of intravenous tramadol for at least two days post-surgery.

In certain preferred embodiments of the intravenous dosing regimens of the invention, the method further comprises administering one or more doses of an intravenous opioid analgesic as rescue medicine to the patient to treat breakthrough pain.

In certain preferred embodiments of the intravenous dosing regimens of the invention, the method further comprises administering the first dose of tramadol on first demand of analgesia post-operatively, further comprising administering a therapeutically effective dose intravenous opioid analgesic to the patient at the end of the surgery.

In certain preferred embodiments of the intravenous dosing regimens of the invention, the method further comprises administering the first dose of tramadol to the patient intra-operatively at wound closure, further comprising administering a bolus of a therapeutically effective dose of intravenous opioid analgesic to the patient if the patient requests analgesia before the second dose of tramadol.

In certain preferred embodiments of the intravenous dosing regimens of the invention, the method further comprises administering a rescue opioid analgesic using Patient Controlled Analgesia (PCA).

In certain preferred embodiments of the intravenous dosing regimens of the invention, the treatment of pain in the patient is opioid-sparing over the first 48 hours post-surgery.

In certain preferred embodiments of the intravenous dosing regimens of the invention, the method further comprises diluting tramadol in a volume of normal saline to provide a unit dose from about 45 mg to about 80 mg tramadol in said volume of normal saline; administering the dose of tramadol intravenously over a time period from about 15 (±2) minutes.

In certain preferred embodiments of the intravenous dosing regimens of the invention, the dose prior to dilution is contained in one or more ampoules.

In certain preferred embodiments of the intravenous dosing regimens of the invention, the ampoules contain tramadol hydrochloride and a buffering agent in water for injection.

In certain embodiments of the intravenous dosing regimens of the invention, the human patient(s) is suffering from acute post-operative pain.

In certain preferred embodiments of the intravenous dosing regimens of the invention, the method provides a reduction in at least one side-effect associated with tramadol therapy (e.g., as compared to prior art intravenous dosing regimens), wherein the side-effect is nausea, vomiting, or seizure.

In certain preferred embodiments of the intravenous dosing regimens of the invention, the method further comprises administering a therapeutically effective dose of an intravenous opioid analgesic is administered to the patient (i) at the end of the surgery, (ii) if the patient requests analgesia before the second dose of tramadol, or (iii) both (i) and (ii).

In certain preferred embodiments, the present invention is directed in part to a method of treating pain, comprising administering to a human patient(s) a therapeutically effective dose of tramadol intravenously over a time period from about 9, 10, 11, 12, 13, 14, 15, 16, 17, 18, 19, 20 21, 22, 23, 24, 25, 26, 27, 28, 29 30, 31, 32, 33, 34, 35, 36, 37, 38, 39, 40, 41, 42, 43, 44 or 45 minutes.

Further aspects of the invention are directed to diluting the dose of tramadol in from about 50 ml to about 500 ml (and preferably from about 50 ml to about 100 ml) of a pharmaceutically acceptable fluid for injection such as normal saline, e.g., in a bag, and standardizing the administration of the injection of the dose of tramadol via the use of a pump.

In another preferred embodiment, the dose of tramadol is provided in the form of a sterile solution at a concentration of about 50 mg tramadol hydrochloride/1 ml prior to dilution.

In certain further preferred embodiments, the dose of tramadol prior to dilution is contained in one or more ampoules. In certain preferred embodiments, the ampoules contain the dose of tramadol (e.g., tramadol hydrochloride) together with a buffering agent (e.g., sodium acetate) in water for injection (e.g., about 1 ml to about 5 ml).

In certain further preferred embodiments, the method further comprises diluting the dose of tramadol into an IV bag for administration to the patient.

In certain preferred embodiments of the present invention, the method further comprises administering a first dose of tramadol to the patient intra-operatively at wound closure, or from first demand of analgesia postoperatively, and administering said further doses of intravenous tramadol for at least two days post-surgery.

In certain preferred embodiments of the present invention, the method further comprises the concomitant administration of one or more opioid analgesics, preferably via the injectable (e.g., intravenous) route as rescue medicine to the patient to treat breakthrough pain that the patient experiences, e.g., for the time period of at least about 48 hours post-surgery. Several options are available for postoperative pain management (Singelyn et al., 1998; Sinatra et al., 2002; both of which are hereby incorporated by reference). Options include intermittent "on-demand" analgesia, continuous epidural analgesia with opioids and/or local anesthetics is effective, or to provide a combination of nerve blocks with long-acting local anesthetics and/or opioids initiated intra-operatively and continued into the immediate postoperative period. For example, most Total knee Arthroplasty (TKA) or Total Hip Arthroplasty (THA) procedures are currently performed with regional (or neuraxial) or other nerve blocks and without general anesthesia. In certain preferred embodiments of the invention, the method further comprises administering a rescue opioid analgesic using Patient Controlled Analgesia (PCA). In certain preferred embodiments, the intravenous administration of opioid analgesic also or alternatively comprises opioid analgesic (e.g., morphine) intravenously to the patient at an effective dose (e.g., morphine in an amount of about 0.05 mg/kg) as a bolus at the end of surgery or upon first demand of analgesia postoperatively, to provide effective analgesia to the patient(s).

In certain preferred embodiments of the invention, the first dose of tramadol is administered on first demand of analgesia postoperatively. Thereafter, the method may further comprise administering a therapeutically (analgesically) effective dose intravenous opioid analgesic to the patient at the end of the surgery, to provide effective analgesia to the patient(s).

In certain preferred embodiments of the invention, the first dose of tramadol is administered to the patient intraoperatively at wound closure. In such embodiments, the method may further comprise administering a bolus of a therapeutically (analgesically) effective dose of intravenous opioid analgesic to the patient if the patient requests analgesia before the second dose of tramadol, to provide effective analgesia to the patient(s).

In preferred embodiments where the tramadol is administered for the treatment of post-operative pain, the treatment of pain in the patient is opioid-sparing over the first 48 hours post-surgery.

In other preferred embodiments, the human patient(s) suffering from pain is unable to ingest an oral dosage form (e.g., of tramadol or another opioid analgesic and/or an NSAID) because the patient is suffering from cancer pain.

In accordance with the above, the final drug product (containing the intravenous dose of tramadol) may be presented as, e.g., as unit-dose ampoules, unit-dose vials, multi-dose ampoules, multi-dose vials, and drug in pre-mixed bags.

In certain preferred embodiments, the M1 metabolite of tramadol (0-desmethyltramadol) contributes to analgesic effect provided by the present invention (dosing regimen), without being toxic (e.g., without significant side effects) to humans at the administered dose of intravenous tramadol.

The present invention is also directed in part to a method of administering tramadol for treating pain via an intravenous dosing regimen comprising intravenously administering at least one loading dose of tramadol to a human patient; thereafter intravenously administering at least one dose of tramadol to the human patient at a dosing interval from about 2 to about 3 hours after administration of the loading dose, and thereafter intravenously administering doses of tramadol at a dosing interval of about 4 to about 6 hours until the patient no longer requires treatment with tramadol, wherein each dose of tramadol is in an amount from about 45 mg to about 80 mg. In certain embodiments, the Cmax of each dose of the intravenous tramadol dosing regimen is from about 80% to about 125% of about 676 ng/mL and the $AUC_6$ of the intravenous tramadol is from about 80% to about 125% of 3230 hr*ng/mL. In certain embodiments, each trough plasma level provided during the tramadol dosing regimen is about the same or greater than the trough level provided by a 100 mg oral dose of tramadol HCl given every 6 hours, at steady-state. In further embodiments, the Cmax of the M1 metabolite of tramadol in the intravenous dosing regimen at steady-state is from about 20% to about 125% or from about 80% to about 125% of about 125 ng/mL.

The invention is further directed in part to a method of improving the safety and tolerability of tramadol for treating pain in human patients, comprising intravenously administering intravenously administering from about 45 mg to about 80 mg tramadol at dosage intervals from about 4 to about 6 hours, except for an additional loading dose administered from about 2 to about 3 hours after the first intravenous dose of tramadol, such that the intravenous dosing regimen provides a steady-state Cmax and AUC of tramadol at about 4 to about 6 hours after initiation of intravenous tramadol therapy, which is similar to the steady-state Cmax and AUC of oral doses of 100 mg tramadol HCl given every 6 hours. In certain embodiments, the method may provide a faster onset of pain relief than oral doses of 100 mg tramadol HCl given every 6 hours.

The invention is further directed in part to a method of improving the safety and tolerability of tramadol for treating pain in human patients, comprising intravenously administering a first dose of tramadol to a human patient in an amount from about 45 mg to about 80 mg; intravenously administering a second dose of tramadol to the human patient in an amount from about 45 mg to about 80 mg at a time from about 2 to about 3 hours after the first dose; intravenously administering a third dose of tramadol to the human patient in an amount from about 45 mg to about 80 mg at a time from about 2 to about 3 hours after the second dose; and thereafter intravenously administering from about 45 mg to about 80 mg tramadol at dosage intervals from about 4 to about 6 hours, until the patient no longer requires treatment with tramadol, such that the intravenous dosing regimen provides a steady-state Cmax and AUC of tramadol at about 4 to about 6 hours after initiation of intravenous tramadol therapy which is similar to the steady-state Cmax and AUC of oral doses of 100 mg tramadol HCl given every 6 hours.

The invention is further directed in part to a method of administering tramadol for treating pain via an intravenous dosing regimen comprising intravenously administering a first dose of tramadol to a human patient in an amount of about 50 mg; intravenously administering a second dose of tramadol to the human patient in an amount of about 50 mg at about 2 hours after the first dose; intravenously administering a third dose of tramadol to the human patient in an amount of about 50 mg at about 2 hours after the second dose; and thereafter intravenously administering additional doses of tramadol to the human patient in an amount of about 50 mg tramadol at dosage intervals of about 4 hours, until the patient no longer requires treatment with tramadol, wherein the tramadol is tramadol base or a pharmaceutically acceptable salt of tramadol. Preferably, the intravenous dosing regimen of this embodiment provides a Cmax and AUC of tramadol which is similar to the Cmax and AUC of an oral dose of 100 mg tramadol HCl given every 6 hours, at steady-state. Preferably, the intravenous dosing regimen provides a mean Cmax of tramadol at steady-state from about 80% to about 125% of about 736 ng/mL, or a mean Cmax of tramadol at steady-state of about 736 ng/mL±152. Preferably, the intravenous dosing regimen provides a mean steady-state concentration of the M1 metabolite of tramadol at steady-state which is from about 20% to about 125% or from about 60% to about 125% of the mean steady-state concentration of the M1 metabolite of tramadol provided by a dosing regimen of 100 mg tramadol HCl administered orally every 6 hours, at steady-state; or from about 80% to about 125% of about 128 ng/mL, or a mean steady-state concentration of the M1 metabolite of tramadol of about 88.9 ng/mL±22.3. Preferably, the mean tramadol Cmax for the first dose of tramadol is from 80% to about 125% of about 294 ng/ml or about 294 ng/mL±68.5. In this embodiment, the mean tramadol concentration for the intravenous dosing regimen provides similar steady-state peak and trough concentrations as compared to a dosing regimen of 100 mg tramadol HCl administered orally every 6 hours, at steady-state. Preferably, the mean tramadol concentration for the intravenous dosing regimen at 48 hours after the first administered dose of tramadol is about 448 ng/ml±131. Preferably, the P/T ratio of tramadol at 48 hours after the first administered dose of tramadol is about 1.6370±0.2655, and the P/T ratio of tramadol after the first administered dose of tramadol is about 1.4566±0.2812. Preferably, the mean Cmax$_{2-4}$ (ng/ml) is about 479±77.7. Preferably, the mean Cmax concentration after administration of the third administered dose of tramadol is similar to the mean Cmax at steady-state, which in turn is similar to the Cmax at steady-state for a dosing regimen of 100 mg tramadol HCl administered orally every 6 hours. In certain preferred embodiments, the tramadol concentration at steady-state for this 50 mg dosing regimen is about 557 ng/mL±131. In certain preferred embodiments, the tramadol M1 metabolite concentration at steady-state for this 50 mg dosing regimen is about 88.9 ng/mL±22.3. In certain preferred embodiments, the human patient(s) is suffering from acute post-operative pain. In further embodiments, the method may result in a reduction in at least one side-effect associated with tramadol therapy, wherein the side-effect is nausea, vomiting, or seizure. In certain preferred embodiments, a therapeutically effective dose of an intravenous opioid analgesic is administered to the patient (i) at the end of the surgery, (ii) if the patient requests analgesia before the second dose of tramadol, or (iii) both (i) and (ii). In certain preferred embodiments, each dose of tramadol is administered intravenously over a time period from about 10 minutes to about 20 minutes, or each dose of tramadol is administered over a time interval of 15 (±2) minutes. In certain preferred embodiments, the pharmacokinetic profile (e.g., plasma concentration curve of tramadol and/or the M1 metabolite of tramadol) achieved with this 50 mg dosing regimen provides surprisingly reduced fluctuation (e.g., peak to trough variance) as compared to a higher (e.g., 75 mg or 100 mg) intravenous dosing regimen. In certain preferred embodiments, the pharmacokinetic profile (e.g., Cmax and AUC) achieved by this 50 mg IV tramadol dosing regimen at a time where the patient might be switched to oral meds (e.g., after the 44-48 hour dosing interval) is similar to the pharmacokinetic profile (e.g., Cmax and AUC) provided at steady-state by a dosing regimen of 100 mg tramadol HCl administered orally every 6 hours. This allows the patient to be stepped down from the intravenous tramadol dosing regimen to an oral dosing regimen. In turn, this allows the patient to be discharged from hospital care with less concern about deleterious effects which might occur from a switch from intravenous to oral analgesic medicine (e.g., the switch to an oral version of the drug providing a much different Cmax and AUC).

In another embodiment of the invention, an IV tramadol dosing regimen is 75 mg administered at Hour 0, followed by 75 mg at Hour 3 and Hour 6, and 75 mg every 6 hours thereafter (e.g., until the patient no longer requires treatment). Thus, in this embodiment, the invention is directed to a method of administering tramadol for treating pain via an intravenous dosing regimen comprising intravenously administering a first dose of tramadol to a human patient in an amount of about 75 mg; intravenously administering a second dose of tramadol to the human patient in an amount of about 75 mg at about 3 hours after the first dose; intravenously administering a third dose of tramadol to the human patient in an amount of about 75 mg at about 6 hours after the second dose; and thereafter intravenously administering additional doses of tramadol to the human patient in an amount of about 75 mg tramadol at dosage intervals of about 6 hours, until the patient no longer requires treatment with tramadol, wherein the tramadol is tramadol base or a pharmaceutically acceptable salt of tramadol. In certain embodiments, this 75 mg intravenous dosing regimen provides a Cmax of tramadol at steady-state from about 80% to about 125% of about 827 ng/mL, or 827 ng/mL±234; or from about 80% to about 125% of about 932 ng/mL, or about 932 ng/mL±199. In certain embodiments, this 75 mg intravenous dosing regimen provides a mean steady-state concentration of the M1 metabolite of tramadol at steady-state which is from about 20% to about 125%, or from about 60% to about 125%; or from about 80% to about 125% of about 86.6 ng/mL, or about 86.6 ng/mL±23.8. In certain embodiments, this 75 mg dosing regimen provides a mean tramadol Cmax for the first dose of tramadol from 80% to about 125% of about 484 ng/ml, or 484 ng/mL±155. In certain preferred embodiments for this 75 mg dosing regimen, the mean tramadol concentration for the intravenous dosing regimen provides similar steady-state peak and trough concentrations as compared to a dosing regimen of 100 mg tramadol HCl administered orally every 6 hours, at steady-state. In certain preferred embodiments for this 75 mg dosing regimen, the mean tramadol concentration for the intravenous dosing regimen at 48 hours after the first administered dose of tramadol is from about 80% to about 125% of about 354 ng/mL, or about 354 ng/mL±85.9. In certain preferred embodiments for this 75 mg dosing regimen, the P/T ratio of tramadol after the first administered dose of tramadol is about 2.0658±0.6131. In certain preferred embodiments for this 75 mg dosing regimen, the P/T ratio of tramadol after the dose administered at 45 hours after the first administered dose of tramadol is about 2.3692±0.5090. In certain preferred embodiments for this 75 mg dosing regimen, the mean Cmax$_{3-6}$ is from about 80% to about 125% of 756 ng/mL, or about 756 ng/mL±141. In certain embodiments for this 75 mg dosing regimen, the human patient(s) is suffering from acute post-operative pain. In certain preferred embodiments for this 75 mg dosing regimen, a reduction in at least one side-effect associated with tramadol therapy may be achieved, wherein the side-effect is nausea, vomiting, or seizure. In certain preferred embodiments for this 75 mg dosing regimen, a therapeutically effective dose of an intravenous opioid analgesic is administered to the patient (i) at the end of the surgery, (ii) if the patient requests analgesia before the second dose of tramadol, or (iii) both (i) and (ii). In certain preferred embodiments for this 75 mg dosing regimen, each dose of tramadol is administered intravenously over a time period from about 10 minutes to about 20 minutes, or over a time interval of 15 (±2) minutes. In certain preferred embodiments, the pharmacokinetic profile (e.g., Cmax and AUC) achieved by this 75 mg IV tramadol dosing regimen at a time where the patient might be switched to oral meds (e.g., after the 42-48 hour dosing interval) is similar to the pharmacokinetic profile (e.g., Cmax and AUC) provided at steady-state by a dosing regimen of 100 mg tramadol HCl administered orally every 6 hours. This allows the patient to be stepped down from the intravenous tramadol dosing regimen to an oral dosing regimen. In turn, this allows the patient to be discharged from hospital care with less concern about deleterious effects which might occur from a switch from intravenous to oral analgesic medicine (e.g., the switch to an oral version of the drug providing a much different Cmax and AUC).

The methods of the present invention are described in further detail in the following sections. However, it should be understood that for purposes of the present invention, the following terms have the following meanings:

The term "acute pain" as used herein means pain that has a sudden onset and commonly declines over a short time (days, hours, minutes) and follows injury to the body and which generally disappears when the bodily injury heals.

The term "effective analgesia" is defined for purposes of the present invention as a satisfactory reduction in or elimination of pain, along with the process of a tolerable level of side effects, as determined by the human patient.

The term "effective pain management" means for purposes of the present invention as the objective evaluation of a human patient's response (pain expressed versus side effects) to analgesic treatment by a physician as well as subjective evaluation of therapeutic treatment by the patient undergoing such treatment. The skilled artisan will understand that effective analgesia will vary according to many factors, including individual patient variations.

The term "breakthrough pain" means pain which the patient experiences despite the fact that the patient is being administered generally effective amounts of, e.g., an opioid analgesic such as buprenorphine.

The term "rescue" refers to a dose of an analgesic which is administered to a patient experiencing breakthrough pain.

An "effective amount" is an amount sufficient to effect beneficial or desired clinical results including alleviation or reduction in pain. In some embodiments, the "effective amount" may reduce the pain of ongoing pain and/or breakthrough pain (including ambulatory pain and touch-evoked pain).

The term "parenterally" as used herein includes subcutaneous injections, intravenous, intramuscular, intrasternal injection or infusion techniques.

The term "patient" as used herein refers to a warm blooded animal such as a mammal which is the subject of trauma, e.g., surgical trauma. It is understood that at least humans, dogs, cats, and mice are within the scope of the meaning of the term.

As used herein, the term "treat" or "treatment", or a derivative thereof, contemplates partial or complete inhibition of acute pain, when a composition of the present invention is administered following the onset of acute pain.

DETAILED DESCRIPTION

Figure 1:
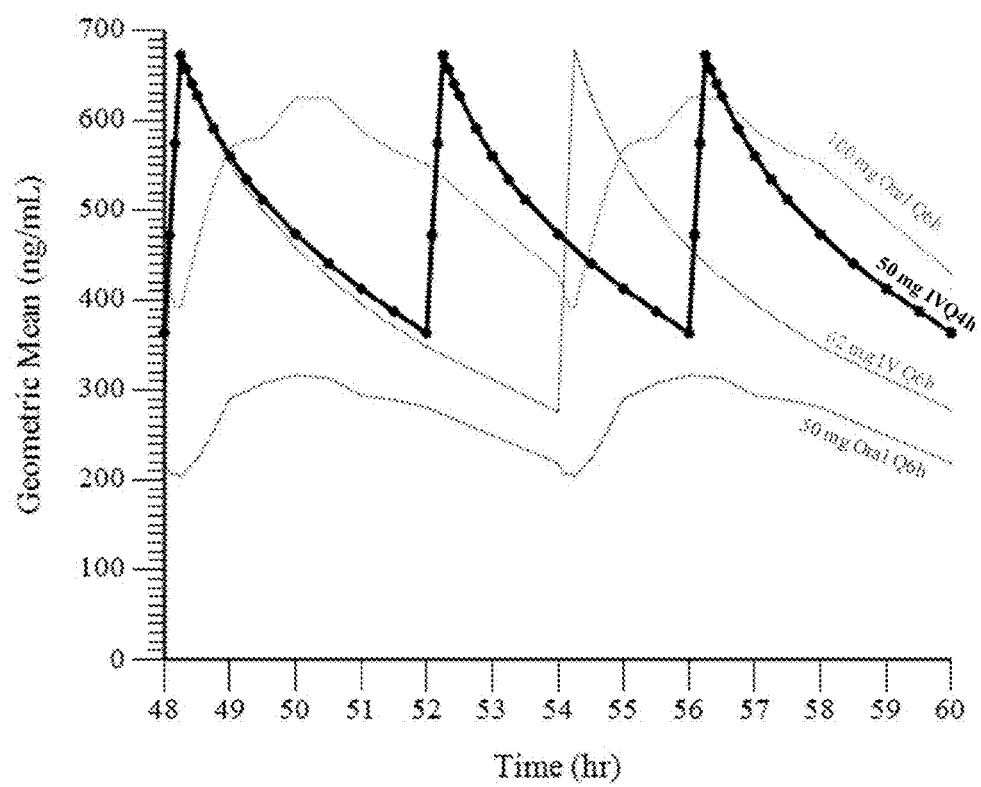
FIG. 1 is a graphical representation of the modeled geometric mean of tramadol concentrations at steady-state when administered Q6 h and Q4 h for Example 1.

The chemical name for tramadol is (±)cis-2-[(dimethylamino)methyl]-1-(3-methoxyphenyl) cyclohexanol hydrochloride [or (1R,2R)-rel-2-[(dimethyl-amino)methyl]-1-(3-methoxyphenyl) cyclohexanol hydrochloride, (1RS, 2RS)-2-[(dimethylamino)methyl]-1-(3-methoxyphenyl) cyclohexanol hydrochloride, (±)-(RR, SS)-2-[(dimethylamino)methyl]-1-(3-methoxyphenyl) cyclohexanol hydrochloride]. Unless otherwise specified, the term tramadol refers to the racemic mixture of the (±)cis isomers.

Tramadol is a centrally-acting synthetic analgesic of the aminocyclohexanol group with opioid-like effects. Tramadol is extensively metabolized following administration resulting in a number of enantiomeric metabolites which display different opioid-receptor binding properties, and monoaminergic reuptake inhibition (Grond and Sablotzki, 2004). Both enantiomers of tramadol and (+)-M1 are responsible for the analgesic effect. The primary metabolite [(+)-M1 or (+)-O-desmethyltramadol] of tramadol confers significant μ-opioid activity; (+)-tramadol confers weak μ-opioid activity and significant serotonin reuptake inhibition; and (−)-tramadol is responsible for the inhibition of noradrenaline re-uptake (Gillen et al., 2000; Raffa, 2008). Nonclinical studies have shown that antinociception induced by tramadol is only partially antagonized by the opiate antagonist, naloxone, indicating that non-opioid mechanisms are also involved in its pharmacodynamic action (Collart et al., 1992).

Tramadol has efficacy in management of acute postoperative pain equivalent to morphine and other opioids administered intravenously, although the onset of action for tramadol is slower. The parenteral route has the advantage of immediate bioavailability and faster onset of action than oral, and is available to postoperative patients who cannot take oral medications. Current standard-of-care injectable analgesics (opioids and NSAIDs) have significant adverse effects, including opiate-induced respiratory depression, excessive sedation, hypotension, dependency, increased bleeding risk, renal toxicity and gastrointestinal irritation, which can potentially slow the postoperative rehabilitation process and compound the risk inherent in any surgical procedure.

Tramadol is currently commercially available in various countries/territories in the following forms: 50 mg/ml or 100 mg/2 ml, solution for injection; 50 mg, capsules, hard; 50 mg, prolonged-release tablets; 100 mg, prolonged-release tablets; 150 mg, prolonged-release tablets; 200 mg, prolonged-release tablets; 50 mg, tablets; 100 mg/ml, oral drops, solution; and 100 mg, suppositories. In the U.S., tramadol is approved by the Food and Drug Administration (FDA) and marketed as an oral capsule/tablet for moderate to moderately severe pain in adults, e.g., under the tradename Ultram® (tramadol hydrochloride tablets).

Parenteral tramadol has been used extensively in Europe and other areas of the world for the amelioration of postoperative pain in both adults and children. The efficacy of tramadol has been thoroughly reviewed (Lee C R, McTavish D, Sorkin E M. Tramadol. A preliminary review of its pharmacodynamic and pharmacokinetic properties, and therapeutic potential in acute and chronic pain states. Drugs. 1993; 46:313-340; Scott L J, Perry C M. Tramadol. A review of its use in perioperative pain. Drugs. 2000; 60:139-176; Grond S and Slabotzi A. Clinical pharmacology of tramadol. Clin Pharmacokinet. 2004; 43:879-923). Parenteral tramadol in such territories consists of tramadol 50 mg or 100 mg administered as a slow bolus injection (over 2-3 minutes) every 4-6 hours.

Surgical procedures often result in some form of acute pain. Surgical pain may include nociceptive, neuropathic or psychological components. Nociceptive pain is a pain experienced as a result of nociception, which is detection of a stimulus by a pain receptor (nociceptor) and transmission of the information to the brain along nerves. Nociceptive pain is caused by tissue damage and inflammation in response to trauma. The resulting pain is usually not well localized and is opioid responsive.

Several options are available for postoperative pain management (Singelyn et al., 1998; Sinatra et al., 2002). Options include intermittent "on-demand" analgesia, continuous epidural analgesia with opioids and/or local anesthetics is effective, or to provide a combination of nerve blocks with long-acting local anesthetics and/or opioids initiated intraoperatively and continued into the immediate postoperative period. In the United States (US) and in India, this latter strategy is frequently employed, and most TKA and THA procedures are currently performed with regional (or neuraxial) or other nerve blocks and without general anesthesia. Each of these options for postoperative pain management can be used concomitantly with the intravenous tramadol treatments described herein as rescue medicine to treat breakthrough pain.

The present invention is directed in part to tramadol in a pharmaceutically acceptable sterile solution formulation containing an effective dose of tramadol or a pharmaceutically acceptable salt thereof, and a method of administration of the same for the treatment of pain, e.g., postoperatively. Tramadol injection in accordance with the present invention will fulfill an important need by providing a safe and effective alternative injectable analgesic for use in the acute postoperative setting.

Preferably, the dose of tramadol administered in accordance with the present invention is, e.g., from about 45 mg to about 80 mg, and in certain preferred embodiments from about 45 to about 55 mg, or from about 70 to about 80 mg, or from about 55 to about 65 mg. In certain preferred embodiments, each tramadol dose administered is in the amount of, e.g., 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 mg, e.g., provided as tramadol hydrochloride. The tramadol may be provided, e.g., as 50 mg tramadol hydrochloride/1 ml. The injectable tramadol dose is generally intended for in-hospital use, although it can be used in other settings. In certain preferred embodiments, the tramadol is administered intravenously over a time period from about 10 minutes to about 3 hours. In certain preferred embodiments, the therapeutically effective dose of tramadol intravenously over a time period from about 10 minutes to about 20 minutes, and most preferably in certain embodiments about 15 (±2) minutes. Thus, in preferred embodiments, the therapeutically effective dose of tramadol intravenously over a time period from about 9, 10, 11, 12, 13, 14, 15, 16, 17, 18, 19, or 20 minutes.

Further aspects of the invention are directed to diluting the dose of tramadol in from about 50 ml to about 100 ml of a pharmaceutically acceptable fluid for injection (such as normal saline), and standardizing the administration of the injection of the dose of tramadol via the use of a pump. In preferred embodiments, the pump is an infusion pump that is commercially available, such as pumps available from Braun and Hospira.

As previously mentioned, the dose of tramadol administered in accordance with the present invention may be diluted in a suitable pharmaceutically acceptable carrier for injection. Examples of such include sterile water for injection, normal saline, etc. Intravenous fluids are well known to those of ordinary skill in the art, and may include other ingredients beyond the dose of tramadol and the carrier/solvent for the tramadol, e.g., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include: alcohol, e.g., 5% alcohol (e.g., in dextrose and water ("D/W") or D/W in normal saline solution ("NSS"), including in 5% dextrose and water ("D5/W"), or D5/W in NSS); synthetic amino acid such as Aminosyn, FreAmine, Travasol, e.g., 3.5 or 7; 8.5; 3.5, 5.5 or 8.5% respectively; ammonium chloride e.g., 2.14%; dextran 40, in NSS e.g., 10% or in D5/W e.g., 10%; dextran 70, in NSS e.g., 6% or in D5/W e.g., 6%; dextrose (glucose, D5/W) e.g., 2.5-50%; dextrose and sodium chloride e.g., 5-20% dextrose and 0.22-0.9% NaCl; lactated Ringer's (Hartmann's) e.g., NaCl 0.6%, KCl 0.03%, $CaCl_2$) 0.02%; lactate 0.3%; mannitol e.g., 5%, optionally in combination with dextrose e.g., 10% or NaCl e.g., 15 or 20%; multiple electrolyte solutions with varying combinations of electrolytes, dextrose, fructose, invert sugar Ringer's e.g., NaCl 0.86%, KCl 0.03%, $CaCl_2$) 0.033%; sodium bicarbonate e.g., 5%; sodium chloride e.g., 0.45, 0.9, 3, or 5%; sodium lactate e.g., ⅙ M; and sterile water for injection The pH of such IV fluids may vary, and will typically be from about 3.5 to about 8 as known in the art.

The dose of tramadol or pharmaceutically acceptable salts thereof can be administered alone or in combination with other medical treatments, or other therapeutic agents, such as NSAIDs. When so-used, other therapeutic agents can be administered before, concurrently (whether in separate dosage forms or in a combined dosage form), or after administration of an active agent of the present invention.

Consistent with the known clinical effects of opioids, nonclinical safety pharmacology studies have shown that tramadol at high doses affects the central nervous system (CNS), producing sedation, impaired mobility, vomiting (dogs), decreased activity, and convulsions (Matthiesen et al., 1998). Also consistent with clinical effects, changes in blood pressure have been observed in cardiovascular studies in rats at high doses (Raimundo et al., 2006). Tramadol use, particularly with high doses, has been associated with seizures, and the risk of seizures is increased in the presence of drugs that reduce seizure threshold, head trauma or prior history of seizures.

The toxicity of tramadol has been summarized by Matthiesen, et al. (1998). The single-dose toxicity of tramadol was similar in all species tested, independent of the route of administration. Notable acute findings included restlessness, unsteady gait, reduced spontaneous activity, exophthalmus, mydriasis, salivation, vomiting (dog), tremor, convulsions, slight cyanosis and dyspnea. The principle findings in repeat-dose toxicity studies in rats and dogs were behavioral/clinical signs and convulsions at doses of ≥25 mg/kg/day. The kidney and liver were identified as potential target organs in rats, with mild effects (minimal tubular vacuolization and perivenular hydropic degeneration, respectively) following repeat intraperitoneal dosing at high doses of tramadol.

There was no evidence of genotoxic potential for tramadol in standard in vitro and in vivo studies (Matthiesen et al., 1998). Carcinogenicity bioassays in mice and rats showed no evidence of carcinogenic potential. An extensive reproductive and teratology program revealed no safety concerns with respect to fertility or teratogenic effects after oral administration (Matthiesen et al., 1998; Yamamoto et al., 1972). Toxicity to offspring only occurred at doses associated with maternal toxicity.

Following oral administration, tramadol is rapidly and almost completely absorbed. The pharmacokinetics of tramadol were evaluated in healthy male volunteers (n=10) in a crossover design using 100 mg PO or IV doses (Lintz et al., 1986). Peak serum concentrations (tmax) were reached approximately 2 hours after oral dosing and the peak serum concentration ($C_{max}$) for PO tramadol was 280±49 ng/mL. The terminal half-life was 5.1 hours for PO and 5.2 hours for IV administration. The area under the serum tramadol concentration-time curve (AUC) was 2488±774 ng·h/mL for PO and 3709±977 ng·h/mL for IV administration. Total clearance was 467±124 mL/min for PO and 710±174 mL/min for IV administration. The absolute bioavailability of the oral dose was 68±13%, based on comparison of the AUC values, while the estimated absorption of the oral dose was 86-88%. The difference between absorption and bioavailability was attributed to first pass metabolism, which was estimated to be ~20%. However, the absolute bioavailability approaches 90-100% with continuous dosing, probably due to saturation of first pass metabolism (Liao et al., 1992). Other studies have corroborated these findings (Grond and Sablotzki, 2004).

The pharmacokinetic profile of tramadol following i.v. and p.o. administration in humans (n=10, male) is summarized in Table A below (Lintz W, Barth H, Osterloh O, Schmidt-Bothelt E. Bioavailability of enteral tramadol formulations. 1st communication: capsules. Arzneim Forsch Drug Res. 1986; 36:1278-1283). The absolute oral bioavailability of tramadol was 68% (±13) in humans.

TABLE A

Pharmacokinetics of Tramadol (100 mg) Following Intravenous and Oral Administration to Humans

| Tramadol (100 mg) | $C_{max}$ (ng/mL) | $t_{1/2}$ (h) | $AUC_{0-24\,h}$ (ng · h/mL) | $V_d$ (L) | CL/F (mL/min) |
|---|---|---|---|---|---|
| i.v. | — | 5.2 ± 0.8 | 3709 ± 977 | 203 ± 40 | 467 ± 124 |
| p.o | 280 ± 49 | 5.1 ± 0.8 | 2488 ± 774 | 306 ± 52 | 710 ± 174 |

Abbreviations:
$C_{max}$, maximal concentration;
$t_{1/2}$, half-life;
AUC, area under the plasma concentration-time curve;
CL, clearance;
F, bioavailability;
$V_d$, volume of distribution The pharmacokinetic profile of tramadol and the (+)-M1 and (−)-M1 metabolites was also evaluated in humans (N=12, male) following p.o. administration of a single 1.5 mg/kg dose of tramadol (Matthiesen, et al., 1993). The data are summarized in Table B below:

TABLE B

Pharmacokinetics of Tramadol and the (+) and (−) Enantiomers of the M1 Metabolite

| Tramadol (1.5 mg/kg, [100 mg]) | $C_{max}$ (ng/mL) | $T_{max}$ (h) | $t_{1/2}$ (h) | AUC (ng · h/mL) | CL/F (mL/min/kg) |
|---|---|---|---|---|---|
| Tramadol | 274 ± 75 | 1.6 ± 0.5 | 5.9 ± 0.7 | 2177 ± 722 | 742 ± 234 |
| (+)-M1 | 147 ± 39 | 1.6 ± 0.5 | 6.0 ± 1.0 | 1258 ± 410 | 642 ± 204 |
| (−)-M1 | 125 ± 32 | 1.5 ± 0.5 | 5.2 ± 0.8 | 908 ± 298 | 883 ± 264 |

Abbreviations:
$C_{max}$, maximal concentration;
$T_{max}$, time to maximal concentration;
AUC, area under the plasma concentration-time curve;
CL, clearance;
F, bioavailability;
$t_{1/2}$, half-life;
$V_d$, volume of distribution Tramadol undergoes hepatic metabolism and both the parent drug and the active metabolite are excreted by the kidneys. The active metabolite, M1 (0 desmethyltramadol), is produced by the action of CYP2D6 isozyme of the cytochrome P450 enzyme system. It has a half-life of approximately 6.7 hours after oral administration (single dose of 100 mg), compared to a half-life of 5.6 hours for tramadol administered intravenously. Hepatic impairment results in decreased metabolism of both the parent compound and the active metabolite. Tramadol is rapidly distributed after IV administration with a distribution half-life in the initial phase of 0.31±0.17 hours, followed by a slower distribution phase with a half-life of 1.7±0.4 hours (Lintz et al., 1986). The volumes of distribution following PO and IV administration were 306 L and 203 L, respectively, indicating that tramadol has a high tissue affinity. The protein binding of tramadol is approximately 20%; however, saturation of binding sites does not occur in the therapeutic dose range (Ultram® Prescribing Information, 2009).

Elimination half-life increases approximately 2-fold in subjects with renal or hepatic impairment. Patients who metabolize drugs poorly via CYP2D6 (Caucasian population prevalence ~8%) may obtain reduced benefit from tramadol due to reduced formation of M1 (Ultram® Prescribing Information, Ortho-McNeil-Janssen Pharmaceuticals, Inc, 2009).

Studies of IV tramadol in the postoperative setting have shown an acceptable safety profile. Loading doses up to 150 mg IV were not associated with any serious adverse effects (Silvasti et al., 2000). Also, no serious adverse effects were observed in clinical trials of tramadol with mean (±SD) cumulative doses of 449±66 mg (Rud et al., 1994), 677±473 mg (range 128-1750 mg) (Silvasti et al., 2000), and 868.3±412.2 mg (Pang et al., 1999) over 24, 36 and 48 h respectively.

The most common adverse events, nausea, dizziness, headache, somnolence, sweating, fatigue, constipation, dry mouth and vomiting, which are usually mild to moderate in severity and only occasionally lead to premature discontinuation of tramadol.

The Ultram® and Tramal® labels contain several warnings and precautions regarding use of tramadol. The risk of most of these potential adverse events can be minimized by decreasing the dose or excluding use of tramadol in subjects with risk factors associated with these known, rare adverse events. Tramadol metabolism is reduced in the setting of advanced cirrhosis and renal clearance of both tramadol and its metabolites is reduced in individuals with creatinine<30 mL/min. Thus, the dose of tramadol should be reduced by half or the interval doubled in these populations. Dosage adjustment is also recommended in individuals >75 years of age as they have reduced drug clearance. Tramadol is metabolized by CYP2D6 and CYP3A4; thus, drugs that are inhibitors or inducers of these enzymes can alter tramadol metabolism, resulting in decreased efficacy and/or increased risk of seizures or other adverse effects. Tramadol is associated with a low risk for respiratory depression, which is increased in the presence of other opioids, anesthetic agents and other CNS depressants, including alcohol. Respiratory depression due to the opioid activity of tramadol can be reversed with naloxone. Naloxone should be used cautiously as it can potentiate seizures when administered with tramadol. The full range of allergic/hypersensitivity reactions have been reported in association with tramadol administration, including serious and rarely fatal anaphylactoid reactions.

Potentially life-threatening serotonin syndrome may occur with tramadol products with concomitant use of serotonergic drugs such as SSRIs, tricyclic antidepressants, monoamine oxidase inhibitors and triptans.

Tramadol use, particularly with high doses, has been associated with seizures, and the risk of seizures is increased in the presence of drugs that reduce seizure threshold, head trauma or prior history of seizures.

Human studies evaluating the abuse potential of tramadol, administered via IV or PO routes, have also been conducted (Epstein et al., 2006). During the initial dose-ranging studies, seizure was observed following a tramadol dose of 700 mg IV administered over 1 minute and 300 mg IV delivered over 2.5 minutes. No seizures were observed with a tramadol dose of 200 mg IV administered over 5 minutes. The authors hypothesized that toxicity is likely to limit abuse of high doses of IV tramadol. In a subsequent study involving 10 experienced opioid abusers, tramadol (100 and 200 mg IV), morphine (10 and 20 mg IV) and placebo were administered over 5 minutes. The endpoints in the study were subjective; the extent to which subjects "liked" the effects of the drugs, as well as their ability to produce effects common to morphine and benzadrine (assessed by the Addiction Research Center Inventory-Morphine Benzadrine Group [ARCI-MBG] scale). Tramadol and morphine significantly increased ratings of "feel drug effect" compared to placebo. However, neither dose of tramadol increased ratings on the "liking" or ARCI-MBG scale or on any other subjective measure of opiate-like effects. In contrast, morphine 10 and 20 mg doses significantly increased ratings of "liking" and the morphine 20 mg dose increased ratings on the ARCI-MBG scale. Thus, tramadol administered via the parenteral route (IV or IM) is unlikely to be associated with the subjective morphine-like and positive mood effects typical of abuse and addiction.

In accordance with the present invention, it is desirable to provide an intravenous dosing regimen of tramadol which at steady-state provides a plasma concentration with respect to Cmax and AUC that is similar or equivalent to the steady-state Cmax and AUC provided by a 100 mg oral tramadol dose given every 6 hours would be desirable and would be safer and have less likelihood of significant side effects than, e.g., the administration of 100 mg of tramadol intravenously administered every 6 hours (i.e., same dose and dosing interval as the oral reference standard, Ultram®. It is further believed that it would desirable for such an intravenous dosing regimen(s) to provide a steady-state trough plasma level of tramadol (e.g., Cmin) which is at least as high as the steady-state trough level provided by a 100 mg oral tramadol dose given every 6 hours. It is further desirable in accordance with the present invention to provide a dosing regimen which reaches but does not substantially exceed the maximum (Cmax) and minimum (Cmin) plasma levels of tramadol obtained at steady-state by a 100 mg oral tramadol dose given every 6 hours as soon as possible within the dosing regimen, e.g., prior to the end of the initial 24 hours of intravenous tramadol, or sooner. As will be explained further herein, for purposes of the present invention the steady-state Cmax of the 100 mg oral dose of tramadol administered every 6 hours is about 736 ng/mL. For purposes of the present invention, a similar or equivalent Cmax provided by an intravenous tramadol dosing regimen would provide a Cmax within the range from about 80% to about 125% of the steady-state Cmax of the 100 mg oral tramadol administered every 6 hours (e.g., 736 ng/mL; or e.g., from about 588.8 ng/mL to about 920 ng/mL). It is especially preferred that the steady-state Cmax of the dosing regimen(s) of the present invention do not exceed the concentration provided by 100 mg oral tramadol administered every 6 hours, at steady-state (e.g., about 701 ng/mL) by more than 15% or more than about 10%.

It is further preferred that the intravenous dosing regimen of tramadol of the present invention at steady-state provides a plasma concentration with respect to Cmax and AUC of the M1 metabolite of tramadol that is similar or equivalent to the steady-state Cmax and AUC of the M1 metabolite provided by a 100 mg oral tramadol dose given every 6 hours, as it is known that the M1 metabolite significantly contributes to the analgesic efficacy of the tramadol formulation. It is further believed that it would desirable for such an intravenous dosing regimen(s) to provide a steady-state trough plasma level of the M1 metabolite of tramadol (e.g., Cmin) which would be therapeutically effective, or which is similar (e.g., from about 20% to about 125%, or from about 60% to about 125%, or from about 80% to about 125%) of the steady-state trough level of the M1 metabolite provided by a 100 mg immediate release oral tramadol dose given every 6 hours. It is further desirable in accordance with the present invention to provide a dosing regimen which reaches but does not substantially exceed the maximum (Cmax) and minimum (Cmin) plasma levels of the M1 metabolite of tramadol obtained at steady-state by a 100 mg oral tramadol dose given every 6 hours as soon as possible within the dosing regimen, e.g., prior to the end of the initial 24 hours of intravenous tramadol, or sooner. As will be explained further herein, for purposes of the present invention the steady-state Cmax of the M1 metabolite for 100 mg oral dose of tramadol administered every 6 hours is about 146 ng/mL±37.4. For purposes of the present invention, a similar or equivalent Cmax of the M1 metabolite provided by an intravenous tramadol dosing regimen would be, e.g., within the range from about 20% to about 125%, or from about 60% to about 125%, or from about 80% to about 125% of the steady-state Cmax of the 100 mg oral tramadol administered every 6 hours (about 146 ng/mL). It is especially preferred that the steady-state M1 metabolite Cmax of the dosing regimen(s) of the present invention does not exceed the 146 ng/mL concentration by more than 10%, or (in certain embodiments) does not exceed the 146 ng/mL level at all during the dosing regimen.

In further preferred embodiments of the present invention, the Cmax and Cmin levels obtained during the initial 24 hour dosing interval are greater than or similar to the Cmax and Cmin levels obtained during the initial 24 hour dosing interval for a 100 mg immediate release oral tramadol dose given every 6 hours, but not significantly greater than the steady-state Cmax level for a 100 mg immediate release oral tramadol dose given every 6 hours.

In accordance with the present invention, the intravenous tramadol dosing regimens of the present invention and as described herein will be similar to, match or exceed the analgesic efficacy of a 100 mg immediate release oral tramadol dose given every 6 hours, but may reduce side effects and/or may improve tolerance as compared to that oral formulation.

The above goals and others are achieved by the present invention, wherein the dose of tramadol is reduced relative to the approved oral dose (100 mg) in the U.S., with the addition of at least one loading dose administered in a shortened dosing interval as compared to the reference standard (Ultram® 100 mg oral tablets). By decreasing the dose of tramadol but increasing the number of administrations during the initial 24 hour period of tramadol administration, the present invention achieves the goal of a lowered dose providing similar Cmax, AUC and efficacy as compared to the orally administered 100 mg tramadol Q6 h.

In a preferred embodiment, the dosing regimen comprises 50 mg IV tramadol at hour 0, followed by 50 mg at hour 2, 50 mg at hour 4, and 50 mg every 4 hours thereafter (e.g., until the patient no longer requires treatment with tramadol). In this embodiment, the maximum plasma concentration (Cmax) of the tramadol rapidly approaches the maximum concentration found at steady-state with respect to a dosing regimen of 100 mg tramadol HCl administered orally every 6 hours. The Cmax obtained after the third dose of 50 mg IV tramadol ($Cmax_{4-6}$) is approximately the same as the Cmax at steady-state for a dosing regimen of 100 mg tramadol HCl administered orally every 6 hours. However, in contrast, the oral tramadol dosing regimen takes considerably longer ($Cmax_{44-48}$) to reach that maximum tramadol plasma concentration. As demonstrated in Example 5 herein, the Cmax of the 50 mg IV tramadol dosing regimen is about 736 ng/mL±152 and is approached during the third dose (see, e.g., Example 5, Table 11 and FIGS. 11-12), whereas the Cmax of tramadol for the oral 100 mg dosing regimen is about 701 ng/ml±178 and occurs at 42-48 hours after the first oral dose is administered (see, e.g., Example 5, Table 11 and FIGS. 9 and 12). Moreover, in this embodiment the trough levels (plasma concentrations of tramadol) also much more rapidly reach a level similar to the trough levels at steady-state for the oral 100 mg every 6 hours dosing regimen. It is believed that the fact that (for the 50 mg IV dosing regimen) peak and trough plasma levels similar to steady-state levels found for the oral 100 mg q6 h dosing regimen are reached at a such an earlier time may translate into improved efficacy (pain relief) for the patients.

It is further believed that the intravenous dosing regimen of the invention, e.g., as a slow push of a therapeutically effective dose of tramadol contained in a bag over a time period from about 10 to about 20 minutes, preferably about 15 minutes, will provide added safety with respect to the above-mentioned potential adverse events and others, and will provide lower incidence of side effects associated with tramadol administration. It is further believed that the intravenous dosing regimen of the invention where a therapeutically effective dose of tramadol is administered to a human patient(s) over a time period from about 24 hours to 48 hours in much slower infusion will also provide these benefits.

The intravenous tramadol formulation in accordance with the invention typically includes tramadol in the form of its hydrochloride salt. However, one of ordinary skill in the art will appreciate that other forms of tramadol may be used, including but not limited to all pharmaceutically acceptable salts of tramadol. Such pharmaceutically acceptable salts may include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, aspargiante, glutamate and the like.

It is contemplated that with respect to the inventive methods for the intravenous administration of tramadol as described herein, other analgesics, preferably opioid analgesics, may be used to treat postoperative pain in the patient(s), as well. It is particularly contemplated that one or more opioid analgesics will be administered post-surgically to the patient as rescue medicine in order to treat breakthrough pain that the patient may experience.

The term "opioid analgesic" refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Opioid analgesics which are useful in the present invention include all opioid agonists or mixed agonist-antagonists, partial agonists, including but not limited to alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, mixtures of any of the foregoing, salts of any of the foregoing, and the like.

In certain preferred embodiments, opioid analgesics include morphine, oxycodone, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof. In certain preferred embodiments, the opioid agonist is morphine. Equianalgesic doses of these opioids are generally known to those persons having ordinary skill in the art.

In certain embodiments, the patient's need for additional analgesic treatment beyond the intravenous tramadol may be ascertained via the use of a surrogate measure of pain. Pain rating scales are used in daily clinical practice to measure pain intensity. The commonly used measurement scales include the Visual Analog Scale (VAS), the Graphic Rating Scale (GRS), the Simple Descriptor Scale (SDS), the Numerical Rating Scale (NRS), and the Faces Rating Scale (FRS). All of these scales have been documented as being valid measures of pain intensity. The three scales most commonly used in the U.S. are the numerical, word and faces scales. One preferred pain rating scale is the visual analog scale (VAS), a 10 cm. vertical or horizontal line with word anchors at the extremes, such as "no pain" on one end and "pain as bad as it could be" at the other. The patient is asked to make a mark along the line to represent pain intensity.

Alternatively, the graphic rating scale (GRS) is a variation of the visual scale which adds words or numbers between the extremes. Wording added might include "no pain", "mild", "severe". The descriptor scale (SDS) is a list of adjectives describing different levels of pain intensity. For example pain intensity may be described as "no pain", "mild", "moderate" or "severe". The numerical pain rating scale (NPRS) refers to a numerical rating of 0 to 10 or 0 to 5 or to a visual scale with both words and numbers. The patient is asked to rate the pain with 0 being no pain and 10 being the worst possible pain. The faces scale was developed for use with children. This scale exists in several variations but relies on a series of facial expressions to convey pain intensity. Grouping patients' rating of pain intensity as measured with a numerical scale ranging from 0 to 10 into categories of mild, moderate, and severe pain is useful for informing treatment decisions, and interpreting study outcomes. In 1995, Serlin and colleagues (Pain, 1995, 277-84) developed a technique to establish the cut points for mild, moderate, and severe pain by grading pain intensity and functional inference. Since then, a number of studies have been conducted to correlate the numerical scales, for example the NPRS, with cutpoints related to levels of pain intensity. Common severity cutpoints are (1 to 4) for mild pain, (5 to 6) for moderate pain, and (7 to 10) for severe pain.

Surrogate measures of opioid efficacy (analgesia) include sedation, respiratory rate and/or pupil size (via pupillometry), and visual analogue scale ("VAS") for "drug effect". The Sum of Pain Intensity Differences (SPID) through 48 hours post first dose (SP1D48) at rest may be used as a primary measure of efficacy.

The intravenous tramadol dosing regimens of the invention may be used in the in the hospital or day hospital setting and therefore administered by medical staff. The tramadol hydrochloride injection for intravenous use and its dosing regimen can fill an important need in addition to tramadol (e.g., ULTRAM®) tablets and tramadol (e.g., ULTRAM® ER) extended-release tablets by providing this safe and effective injectable analgesic with a novel mechanism of action (µ-opioid agonist and monoaminergic reuptake inhibition) for use in the acute post-operative setting. These dosing regimens may be used, e.g., for all types of surgery, including orthopedic surgery (e.g., total knee replacement, bunionectomy) or soft tissue surgery (e.g., elective abdominoplasty).

DETAILED DESCRIPTION OF PREFERRED EMBODIMENTS

This invention is further illustrated by the following examples that should not be construed as limiting. Those of skill in the art of pharmaceutical formulation will readily appreciate that certain modifications to the examples may be readily effected. Any methods, materials, or excipients which are not particularly described will be generally known and available those skilled in the drug design and assay and pharmacokinetic analysis.

Example 1

The purpose of this analysis was to calculate the systemic exposure of tramadol and its active metabolite M1, when given as an intravenous (IV) infusion that would provide an AUC and Cmax that are comparable to immediate release oral tramadol HCl 100 mg administered every 6 hours (e.g., Ultram® 100 mg IR q6 h).

Tramadol is extensively metabolized by CYP2D6 and CYP3A4. One metabolite, M1, is 6 times more potent than the parent compound in producing analgesia and 200 times more potent in µ opioid binding in animal model. For PK modeling purposes, tramadol level (Cmax) was considered to be the most important parameter, as it is most directly related to seizure risks. Due to first pass metabolic saturation, steady-state plasma concentration exceeds that of a single dose administration. Steady-state is reached in about 42-48 hours. For PK modeling purposes, the dose proportionality study previously reported in the assignee's U.S. Pat. No. 8,895,622 was used as basis for the modeling.

Using the compartment model for tramadol and M1, a 62 mg dose was estimated to result in a $C_{max}$ close to what was observed for a 100 mg oral dose (geometric mean oral $C_{max}$=676 ng/mL). It was concluded that the infusion rate did not affect the calculated $AUC_6$ for either analyte, and that the $C_{max}$ for both analytes were fairly insensitive to viable infusion durations of 10 to 20 minutes (the modeled Cmax was 680 ng/mL for a 10 minute infusion time, 678 ng/mL for a 15 minute infusion time, and 670 ng/mL for a 20 minute infusion time). Since an infusion duration in the 10 to 20 minute range did not influence the $C_{max}$ of either tramadol or the M1 metabolite, a linear model and a power model were investigated vs. the effect of dose alone.

The critical threshold values for $C_{max}$ and $AUC_6$ (the AUC or "area under the curve" predicted after 6 doses) resulting from 50 mg and 100 mg (60 mg and 120 mg dose by extrapolation) oral doses of tramadol are presented in Table 1. The predicted oral dose to achieve threshold PK parameters is shown in Table 2. Table 3 lists the various predicted IV doses required to reach the various threshold values for a given PK parameter. For example, a 30 mg IV dose would result in a similar $C_{max}$ value as a 50 mg oral dose. An 81 mg IV dose would result in similar M1 AUC value as that observed for one 100 mg oral dose. In all cases, the tramadol $C_{max}$ threshold is reached using the lowest IV dose, therefore it was considered that the lowest dose is the defining dose.

TABLE 1

PK Parameters for 50 mg and 100 mg Oral Tramadol
Threshold PK Parameters

| Oral Dose (mg) | Tramadol | | M1 | |
|---|---|---|---|---|
| | $C_{max}$ (ng/mL) | $AUC_6$ (hr * ng/mL) | $C_{max}$ (ng/mL) | $AUC_6$ (hr * ng/mL) |
| 50 | 340 | 1641 | 96 | 491 |
| 60 | 408 | 1969 | 115 | 589 |
| 100 | 676 | 3230 | 125 | 668 |
| 120 | 811 | 3876 | 150 | 802 |

TABLE 2

Linear Model: Calculated Dose Required to Reach PK Parameters for
50 mg and 100 mg Oral Tramadol
Predicted Dose to Achieve Threshold PK Parameter

| Oral Dose (mg) | Tramadol | | M1 | |
|---|---|---|---|---|
| | $C_{max}$ (mg Dose) | $AUC_6$ (mg Dose) | $C_{max}$ (mg Dose) | $AUC_6$ (mg Dose) |
| 50 | 30 | 39 | 61 | 59 |
| 60 | 36 | 47 | 73 | 71 |
| 100 | 59 | 77 | 80 | 81 |
| 120 | 71 | 92 | 96 | 97 |

TABLE 3

Linear Model: PK Parameters at Predicted Threshold Dose Required to
Reach Equivalent $C_{max}$ for 50 mg and 100 mg Oral Tramadol
Predicted PK Parameters

| | Dose (mg) | Tramadol | | M1 | |
|---|---|---|---|---|---|
| Oral Dose (mg) | IV | $C_{max}$ (ng/mL) | $AUC_6$ (hr * ng/mL) | $C_{max}$ (ng/mL) | $AUC_6$ (hr * ng/mL) |
| 50 | 30 | 342 | 1263 | 47 | 248 |
| 60 | 36 | 410 | 1515 | 57 | 298 |
| 100 | 59 | 673 | 2483 | 93 | 488 |
| 120 | 71 | 810 | 2988 | 111 | 587 |

The confidence intervals for Cmax resulting from IV administration was narrower than that seen after oral administration. The 90% confidence interval for a 65-mg IV dose lies within that of the Cmax resulting from administration of the 100 mg oral dose.

The results for Example 1 led to the conclusion that IV 60 mg q6 h provides a Cmax comparable to the referenced product (oral IR 100 mg tramadol HCl) but with a much lower AUC and M1 levels. Since the M1 metabolite is known to provide a significant contribution to analgesia, and a lower AUC is predicted to reduce efficacy, further research regarding a useful IV formulation that would provide a Cmax comparable to the referenced product but having a greater likelihood of providing the desired efficacy was desired.

Example 2

In this Example, the administration of tramadol and its active metabolite M1 were evaluated using model simulated parameters, when administered as a 15-minute intravenous (IV) infusion of tramadol every 4 hours using a compartmental model previously developed to describe the pharmacokinetics of the parent drug tramadol and its M1 metabolite as administered Q6 h, with the goal of the intravenous dosing regimen to provide a Cmax and AUC of tramadol which is similar to the Cmax and AUC of an oral dose of 100 mg tramadol HCl given every 6 hours. In this Example, a 48 mg IV infusion administered every 4 hours and a 62 mg IV infusion administered every 4 hours were modeled.

The geometric mean at steady-state for Cmax and AUC6 of tramadol and M1 resulting from the simulated IV infusion given Q4 h at a dose of 48 mg was similar to that observed at Q6 h for the 100 mg oral dose. The percent of PK value at steady-state of tramadol for the simulated IV infusion administered Q4 h at 48 mg was slightly lower for Cmax and similar for AUC6 to that of the 100 mg oral dose (Table 4 and Table 5).

TABLE 4

Geometric Mean: Steady-State Tramadol $C_{max}$ and $AUC_6$ for Observed
Oral Dose and Simulated IV Infusion

| Administration | Tramadol | | M1 | |
|---|---|---|---|---|
| Administration | $C_{max}$ C(ng/mL) | $AUC_6$* (hr * ng/mL) | $C_{max}$ C(ng/mL) | $AUC_6$ (hr * ng/mL) |
| 100 mg Oral Dose Q6h | 676 | 3230 | 125 | 668 |
| 48 mg IV Infusion Q4h | 672 | 2904 | 102 | 594 |
| 62 mg IV Infusion Q6h | 678 | 2509 | 91 | 514 |

*Steady-state $AUC_6$ for Q4h calculated from $C_{avg}$ * 6 hr

TABLE 5

Percent of Steady-State PK Value with Respect to the 100 mg Oral Dose

| | Tramadol | | M1 | |
|---|---|---|---|---|
| | $C_{max}$ | $AUC_6$ | $C_{max}$ | $AUC_6$ |
| Administration | Percent of PK Value with Respect to the 100 mg Oral Dose | | | |
| 48 mg IV Infusion Q4h | 99% | 90% | 82% | 89% |
| 62 mg IV Infusion Q6h | 100% | 78% | 73% | 77% |

The results of the modeling as depicted in Tables 1 and 2 show that increasing the frequency of dosing from every 6 hours to every 4 hours necessitated a lowering of the dose, as a 62 mg dose Q4 h would result in a mean steady-state Cmax value of 868 ng/mL (not shown) which is well-above the Cmax of the 100 mg oral dose of 676 ng/mL. After carrying out various simulations, a 48-mg 15 minute infusion every 4 hours was found to result in a similar Cmax value to that of the 100 mg oral dose. In addition, the 48 mg Q4 h dosing regimen allowed the tramadol AUC6 to more closely resemble that of the 100 mg oral Q6 h. The results show that tramadol given as a 48 mg every 4 hours offers a significant advantage over the 62 mg every 6 hours in that the tramadol AUC6 increased to 90% of the 100 mg oral value. The more frequent administration regime has the added benefit of higher trough levels of tramadol, avoiding the possibility of sub-therapeutic concentrations.

The geometric mean of tramadol concentrations at steady-state when administered Q6 h and Q4 h are presented in FIG. 1.

Example 3

In Example 3, three different dosing regimens were modeled based on the results in Examples 1 and 2. In Examples 3a-3c, a 50 mg intravenous tramadol dose was modeled via administration every 4 hours.

In Example 3a ("100 mg Loading Dose"), a 100 mg intravenous tramadol loading dose was first administered, and then a 50 mg intravenous tramadol dose is administered 4 hours later. Thereafter, the intravenous tramadol is administered as a 50 mg dose every 4 hours (100 mg dose, followed by 50 mg q4 h).

In Example 3b ("50 mg Loading at 2 hr"), a 50 mg tramadol dose is initially administered (at 0 hours). Therefore, in this dosing regimen, a 50 mg intravenous tramadol dose is administered 2 hours after the initial 50 mg dose (as a second dose). Another 50 mg intravenous dose is administered 2 hours after the second dose. Thereafter, 50 mg intravenous tramadol is administered every 4 hours. (50 mg at T0, 50 mg at T2, followed by 50 mg at T4, T8 . . . ).

In Example 3c ("1st Dosing Interval 2 hr"), a 50 mg tramadol dose is initially administered (at 0 hours). Therefore, in this dosing regimen, a 50 mg intravenous tramadol dose is administered 2 hours after the initial 50 mg dose (as a second dose). Another 50 mg intravenous dose is administered 4 hours after the second dose. Thereafter, 50 mg intravenous tramadol is administered every 4 hours. (50 mg at T0, 50 mg at T2, followed by 50 mg at T6, T10 . . . ).

In Table 6, the geometric mean Cmax (ng/mL) values of Examples 3a-3c are modeled, using the various loading doses explained above, and compared against a 50 mg dose given every 4 hours with no loading dose:

TABLE 6

| | 0 hr to 2 hr | 2 hr to 4 hr | 4 hr to 6 hr | 6 hr to 8 hr | 8 hr to 10 hr | 10 hr to 12 hr |
|---|---|---|---|---|---|---|
| No Loading Dose | 311 | | 433 | | 507 | |
| Steady-State 50 mg Q4 h | 700 | | 700 | | 700 | |
| 100 mg Loading Dose | 621 | | 555 | | 580 | |
| 50 mg Loading at 2 hr | 311 | 484 | | 605 | | 599 |
| 1rst Dosing Interval 2 hr | 311 | 484 | | 526 | | 567 |

Figure 2:
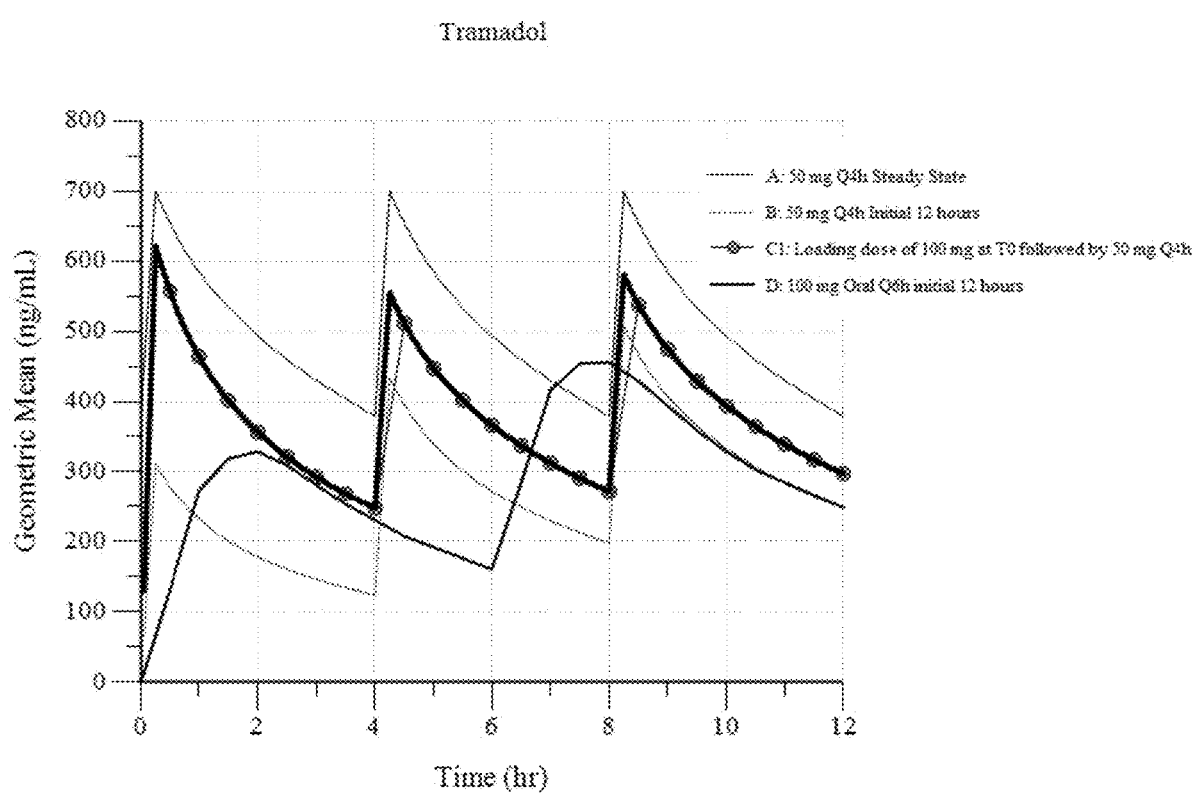
FIG. 2 is a graphical representation of the modeled plasma curve of Example 3a (100 mg loading dose) plotted against the plasma curve provided by a 100 mg oral tramadol dose given every 6 hours.

FIG. 2 is a graphical representation of the modeled plasma curve of Example 3a (100 mg loading dose) plotted against the plasma curve provided by a 100 mg oral tramadol dose given every 6 hours. The peak concentration of Example 3a during the first dosing interval approaches the peak concentration for a 100 mg oral tramadol dose given every 6 hours, at steady-state, but does not exceed that level. Also, the trough levels provided after the first and second doses are higher than the trough concentrations provided at the end of the first dosing interval for a 100 mg oral tramadol dose given every 6 hours.

Figure 3:
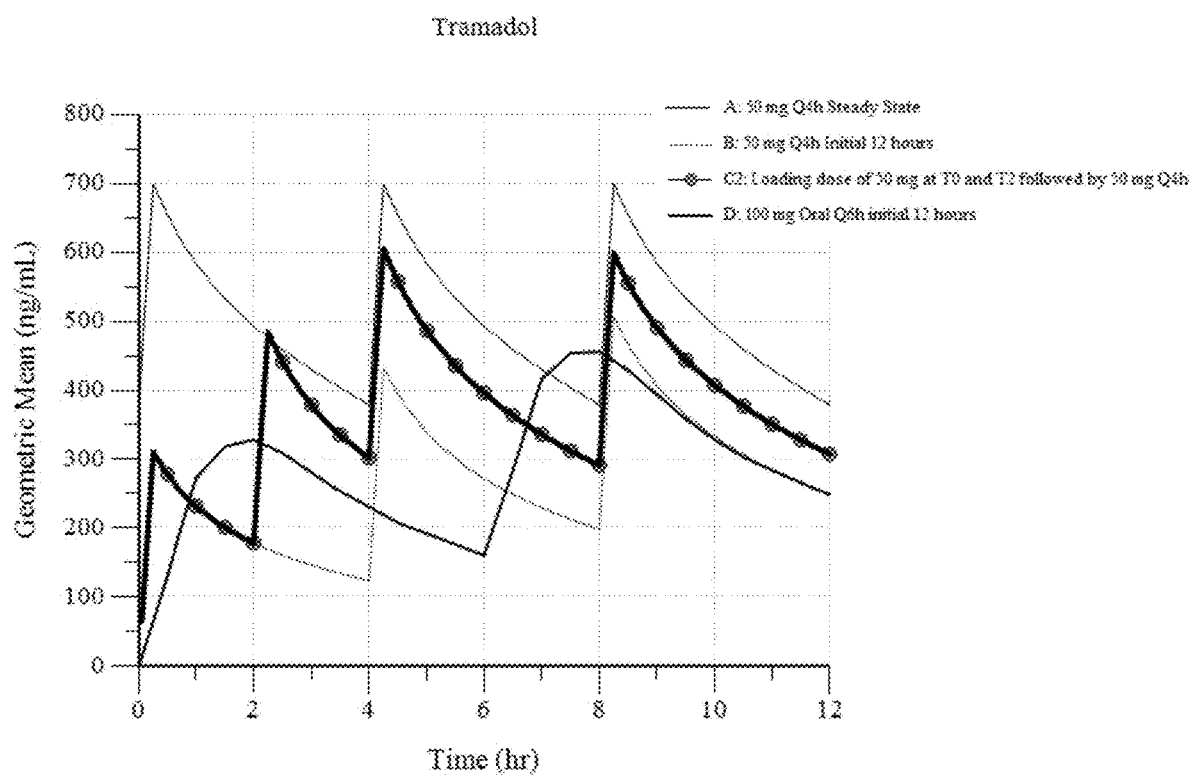
FIG. 3 is a graphical representation of the modeled plasma curve of Example 3b (50 mg loading at 2 hr) plotted against the plasma curve provided by a 100 mg oral tramadol dose given every 6 hours.

FIG. 3 is a graphical representation of the modeled plasma curve of Example 3b (50 mg loading at 2 hr) plotted against the plasma curve provided by a 100 mg oral tramadol dose given every 6 hours. It can be seen in FIG. 3 that the first peak plasma concentration of Example 3b depicted in the graph is similar to the first peak plasma concentration provided by a 100 mg oral tramadol dose given every 6 hours. On the other hand, the trough concentrations provided by Example 3b are higher than the trough concentrations provided at the end of the first dosing interval for a 100 mg oral tramadol dose given every 6 hours. This data indicates to one of skill in the art that the dosing regimen of Example 3b is a useful manner to administer IV tramadol to match the plasma concentration curve of oral tramadol, while improving tolerance and reducing side effects.

With respect to the modeled plasma curve of Example 3c (1st Dosing Interval 2 hr) as compared against the plasma curve provided by a 100 mg oral tramadol dose given every 6 hours, the first peak plasma concentration of Example 3c is similar to the first peak plasma concentration provided by a 100 mg oral tramadol dose given every 6 hours. On the other hand, the trough concentrations provided by Example 3c are higher than the trough concentrations provided at the end of the first dosing interval for a 100 mg oral tramadol dose given every 6 hours. This data indicates to one of skill in the art that the dosing regimen of Example 3b is a useful manner to administer IV tramadol to match the plasma concentration curve of oral tramadol, while improving tolerance and reducing side effects. However, the trough concentrations of Example 3b are significantly higher than the trough concentrations of Example 3c, while the peak concentrations of Example 3b are lower than the steady-state peak plasma concentration provided by a 100 mg oral tramadol dose given every 6 hours, but yet greater than the peak concentrations of Example 3c over the same time interval. This data would lead one of skill in the art to prefer Example 3b over Example 3c.

Example 4

In Example 4, a simulation was conducted in order to compare a 75 mg IV tramadol dosing regimen using a 15 minute infusion every 6 hours (Q6 h) with an additional dose at three hours, and the comparison of steady-state pharmacokinetic profiles of tramadol and M1 obtained with that dosing regimen to 100 mg oral tramadol Q6 h.

Table 7 provides the modeled geometric mean Cmax and AUC values for both tramadol and its M1 metabolite and compares the same to the pharmacokinetic values of 100 mg oral tramadol Q6 h.

TABLE 7

| | | Analyte | | | |
|---|---|---|---|---|---|
| | | Tramadol | | M1 | |
| Dose | Time Interval | $C_{max}$ (ng/mL) | AUC (hr * ng/mL) | $C_{max}$ (ng/mL) | AUC (hr * ng/mL) |
| 75 mg IV | 0-3 hr | 485 | 948 | 34 | 65 |
| | 3-6 hr | 710 | 1498 | 69 | 171 |
| | 6-12 hr | 855 | 3059 | 99 | 551 |
| | 12-18 hr | 813 | 2981 | 106 | 600 |
| | Steady-State | 821 | 3035 | 110 | 622 |
| 100 mg Oral* | Steady-State | 676 | 3230 | 125 | 668 |

Figure 4:
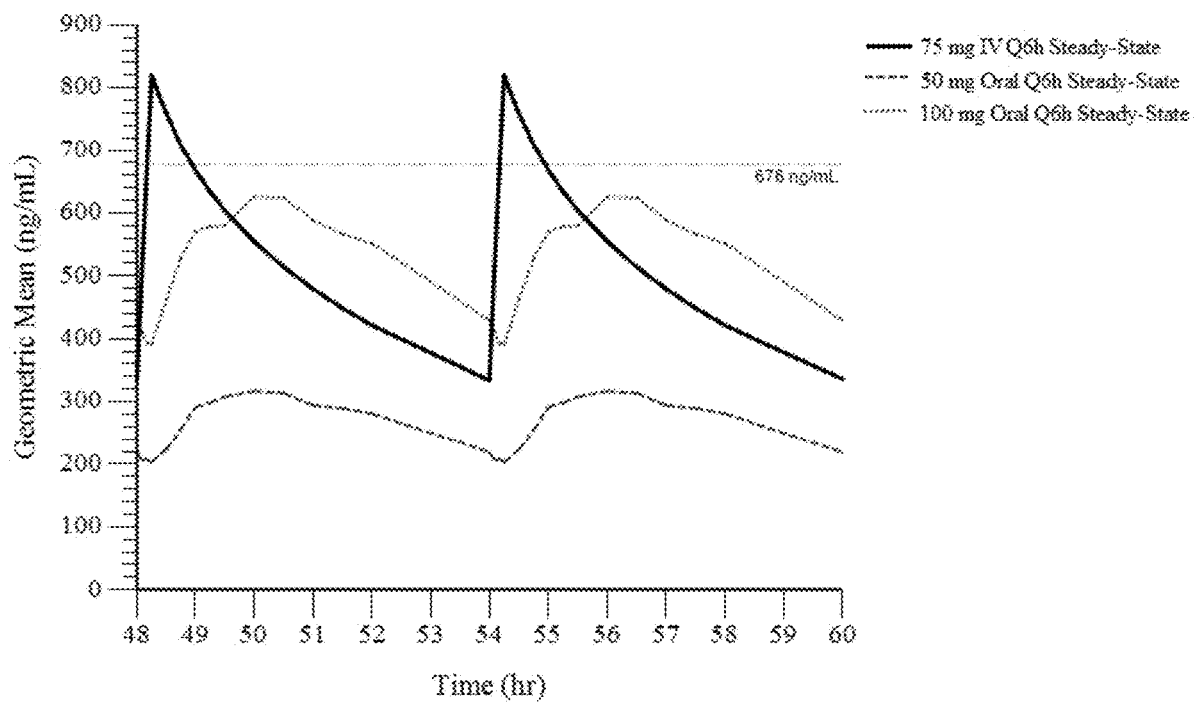
FIG. 4 is a graphical representation of the simulated tramadol plasma levels of Example 4 plotted against the plasma concentration curves for a 100 mg and a 50 mg oral tramadol dose administered every 6 hours, at steady-state.

FIG. 4 is a graphical representation of the simulated tramadol plasma levels of Example 4 plotted against the plasma concentration curves for a 100 mg and a 50 mg oral tramadol dose administered every 6 hours, at steady-state. In FIG. 4, the reference plasma concentration of 676 ng/ml is the tramadol geometric mean steady-state Cmax value resulting from 100 mg oral tramadol administered every 6 hours.

Figure 5:
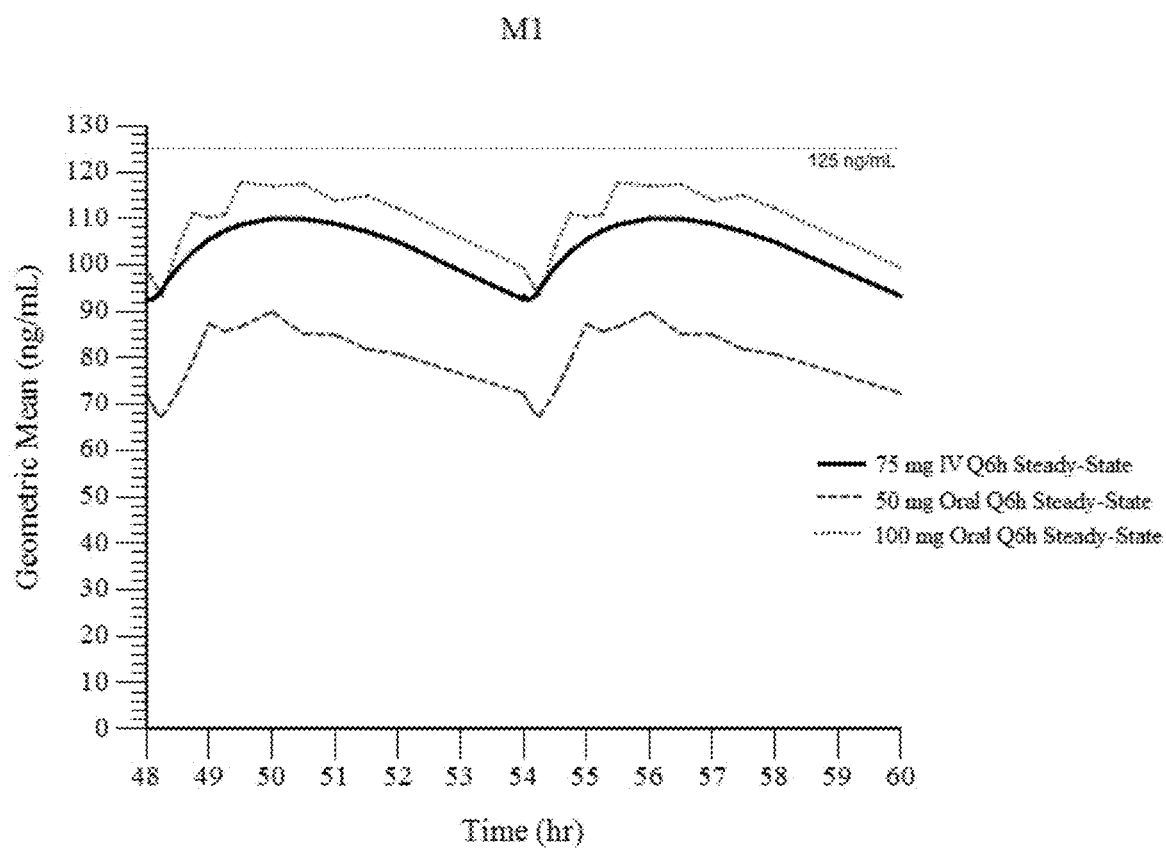
FIG. 5 is a graphical representation of the simulated M1 metabolite plasma levels of Example 4 plotted against the M1 metabolite plasma concentration curves for a 100 mg and a 50 mg oral tramadol dose administered every 6 hours, at steady-state.

FIG. 5 is a graphical representation of the simulated M1 metabolite plasma levels of Example 4 plotted against the M1 metabolite plasma concentration curves for a 100 mg and a 50 mg oral tramadol dose administered every 6 hours, at steady-state. In FIG. 5, the reference plasma concentration of 676 ng/ml is the tramadol geometric mean steady-state Cmax value resulting from 100 mg oral tramadol administered every 6 hours.

Figure 6:
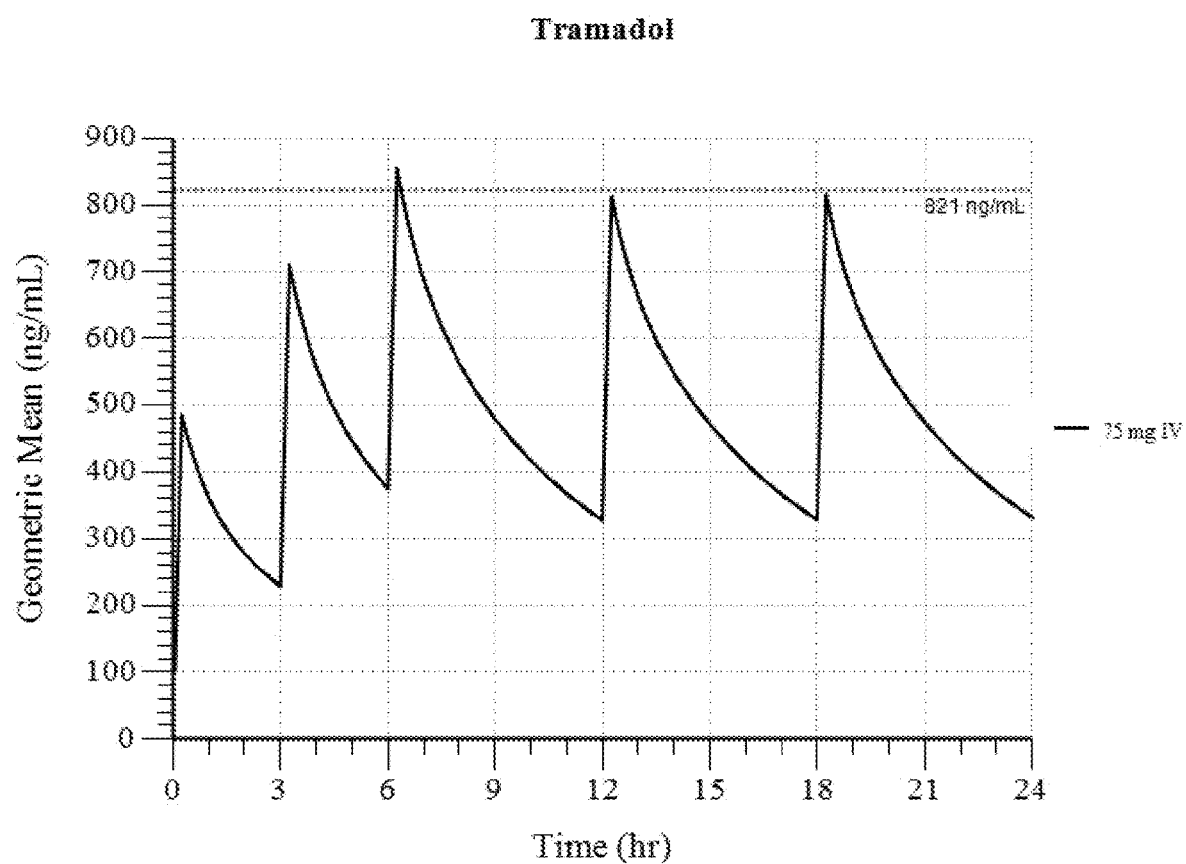
FIG. 6 is a graphical representation of the simulated plasma concentration of Example 4 over the initial 24 hours.

FIG. 6 is a graphical representation of the simulated plasma concentration of Example 4 over the initial 24 hours. In FIG. 6, the reference plasma concentration of 676 ng/ml is the tramadol geometric mean steady-state Cmax value resulting from 100 mg oral tramadol administered every 6 hours. It can be seen that by the third dose of the modeled Example 4 (75 mg doses), the Cmax is reached which is equivalent to the steady-state Cmax of the 100 mg oral tramadol administered every 6 hours.

Figure 7:
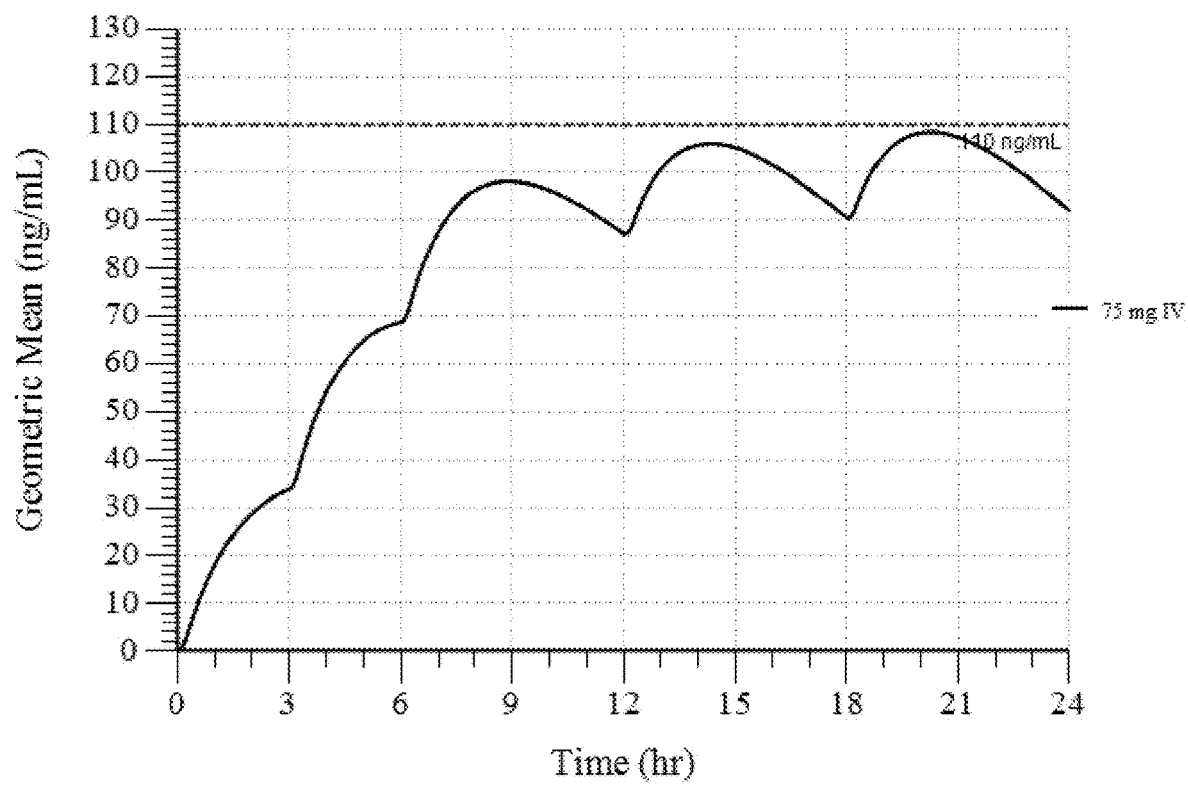
FIG. 7 is a graphical representation of the simulated M1 metabolite plasma concentration of Example 4 over the initial 24 hours.

FIG. 7 is a graphical representation of the simulated M1 metabolite plasma concentration of Example 4 over the initial 24 hours. In FIG. 7, the reference M1 plasma concentration of 125 ng/mL is the M1 geometric mean steady-state Cmax value resulting from 100-mg oral dose administered every 6 hours. It can be seen that by the fifth dose of the modeled Example 4 (75 mg doses), the Cmax is reached which is equivalent to the steady-state M1 metabolite Cmax of the 100 mg oral tramadol administered every 6 hours.

Figure 8:
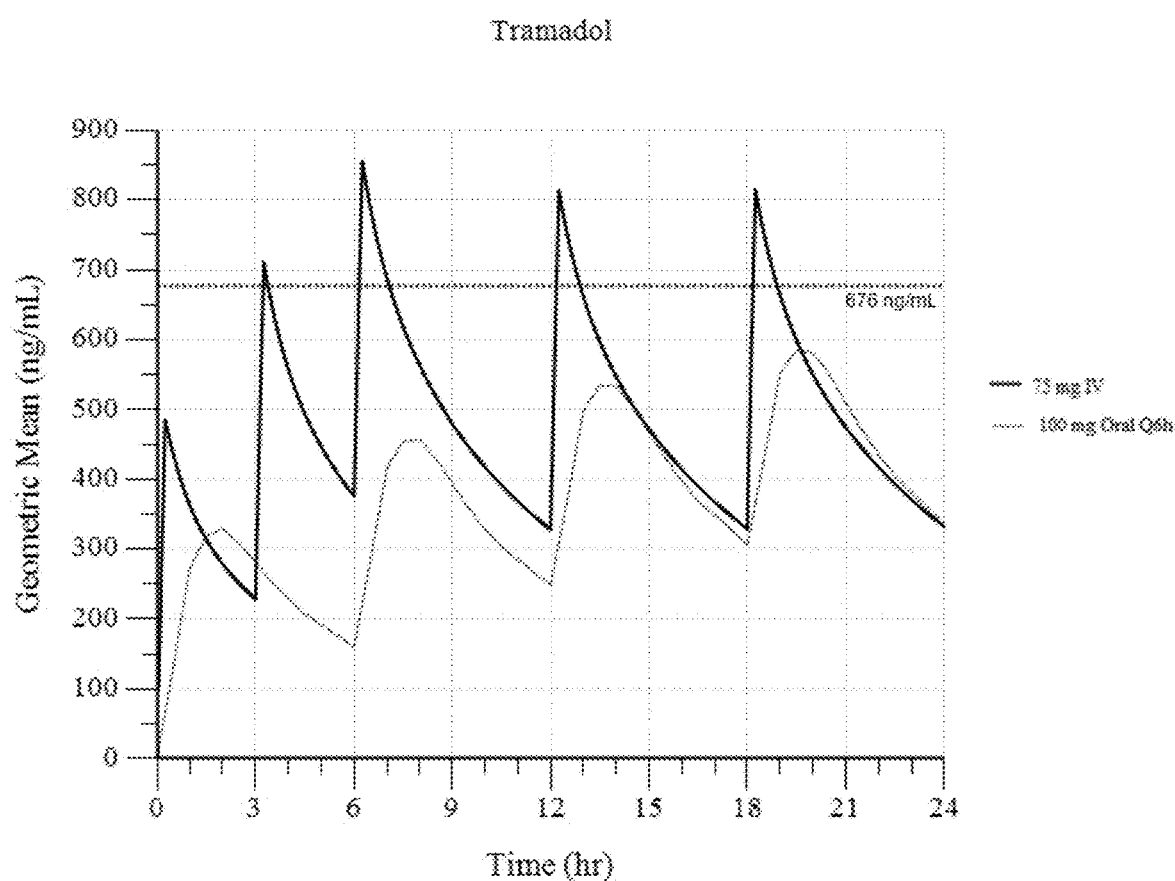
FIG. 8 is a graphical representation of the simulated tramadol plasma concentration of Example 4 over the initial 24 hours, plotted against the tramadol plasma concentration of the 100 mg oral tramadol administered every 6 hours, and the reference plasma concentration of 676 ng/ml.

FIG. 8 is a graphical representation of the simulated tramadol plasma concentration of Example 4 over the initial 24 hours, plotted against the tramadol plasma concentration of the 100 mg oral tramadol administered every 6 hours, and the reference plasma concentration of 676 ng/ml (which is the tramadol geometric mean steady-state Cmax value resulting from 100 mg oral tramadol administered every 6 hours). The initial 24 hour oral data was digitally extracted from Yalda H. Ardakani and Mohammad-Reza Rouini, "Pharmacokinetics of Tramadol and its Three Main Metabolites in Healthy Male and Female Volunteers" Biopharm. Drug Dispos. 28: 526-533 (2007). Both IV and oral multiple doses were simulated using semiparametric superposition method.

Table 8 provides the percent of pharmacokinetic value of Example 4 with respect to 100 mg Oral Steady-State for Cmax and AUC for both tramadol and its M1 metabolite.

TABLE 8

| | | Analyte | | | |
|---|---|---|---|---|---|
| | | Tramadol | | M1 | |
| Dose | Time Interval | $C_{max}$ (ng/mL) | AUC (hr * ng/mL) | $C_{max}$ (ng/mL) | AUC (hr * ng/mL) |
| 75 mg IV | 0-3 hr | 72% | 29% | 27% | 10% |
| | 3-6 hr | 105% | 46% | 55% | 26% |
| | 6-12 hr | 126% | 95% | 79% | 82% |
| | 12-18 hr | 120% | 92% | 85% | 90% |
| | Steady-State | 121% | 94% | 88% | 93% |

For comparative purposes, Table 9 provides the geometric mean Cmax and AUC values for both tramadol and its M1 metabolite.

TABLE 9

| | | Analyte | | | |
|---|---|---|---|---|---|
| | | Tramadol | | M1 | |
| Dose | Time Interval | $C_{max}$ (ng/mL) | AUC (hr * ng/mL) | $C_{max}$ (ng/mL) | AUC (hr * ng/mL) |
| 75 mg IV | 0-3 hr | 485 | 948 | 34 | 65 |
| | 3-6 hr | 710 | 1498 | 69 | 171 |
| | 6-12 hr | 855 | 3059 | 99 | 551 |
| | 12-18 hr | 813 | 2981 | 106 | 600 |
| | Steady-State | 821 | 3035 | 110 | 622 |
| 100 mg Oral* | Steady-State | 676 | 3230 | 125 | 668 |

The results of Example 4 may be summarized as follows. Tramadol AUC6, M1 AUC6 and M1 Cmax are below the steady-state values observed for the 100-mg oral dose. At steady-state, tramadol AUC6, M1 AUC6 and M1 Cmax are similar but below the steady-state values observed for the 100 mg oral dose. At steady-state, the tramadol Cmax value (821 ng/mL) is above the 100 mg oral dosing regimen (676 ng/mL). Tramadol Cmax attains its highest value at the 6 hour dosing interval of 855 ng/mL. Compared to the 100 mg oral dosing, the IV dosing regimen (75 mg Q6 h with an additional dose at 3 hours) allows for a greater systemic exposure of Tramadol earlier on.

Example 5

In Example 5, a PK study in healthy volunteers was conducted to evaluate the relative exposure of two intravenous (IV) dose regimens of tramadol compared to the approved 100 mg Q6 h oral dose regimen of tramadol. The two tramadol IV dosing regimens were based on various pharmacokinetic (PK) simulations done prior to the study, and it was determined that the following were appropriate for evaluation: (1) 75 mg IV REGIMEN: IV tramadol 75 mg administered at Hour 0, followed by 75 mg at Hour 3 and Hour 6, and 75 mg every 6 hours thereafter through Hour 42; (2) 50 mg IV REGIMEN: IV tramadol 50 mg administered at Hour 0, followed by 50 mg at Hour 2, 50 mg at hour 4, and 50 mg every 4 hours thereafter through Hour 44. These two IV dosing regimens were studied in a multiple-dose, randomized, PK 3-way crossover study in 18 healthy volunteers, each of whom also received 100 mg oral tramadol given every 6 hours during one of the periods through Hour 42.

Examination of the parent (tramadol) as well as the primary metabolite (M1 (0-desmethyltramadol) was performed over the 48-hour treatment period. A focus of the analysis was on assessment of Cmax values (to ensure the Cmax for the IV formulation was similar to that of the oral formulation) as well as on early concentrations during the first doses (to ensure adequate medication would be provided during the initial 6 to 12 hours of treatment as the drugs reached steady-state concentrations). Overall exposure to tramadol was estimated from average trough plasma concentrations.

A fitted curve was obtained because the second oral peak was not measured in the study. For the modeling portion of the analysis, a validated Phoenix® WinNonlin® program version 6.4 (Certara) was used for PK analysis, simulation, graphics, tables and statistical calculations. Tramadol plasma concentration-time data observed over the initial 24 hours was fit to a linear 1-compartment model with first-order absorption and a lag time. For purposes of nonlinear regression, the data were weighted as 1/observed. Predicted concentration-time data were calculated based on the individual fitted PK parameters. The oral Cmax and AUC values over the initial 12 and 24 hours after administration was calculated using noncompartmental analysis of the predicted concentration using a fitted model.

Figure 9:
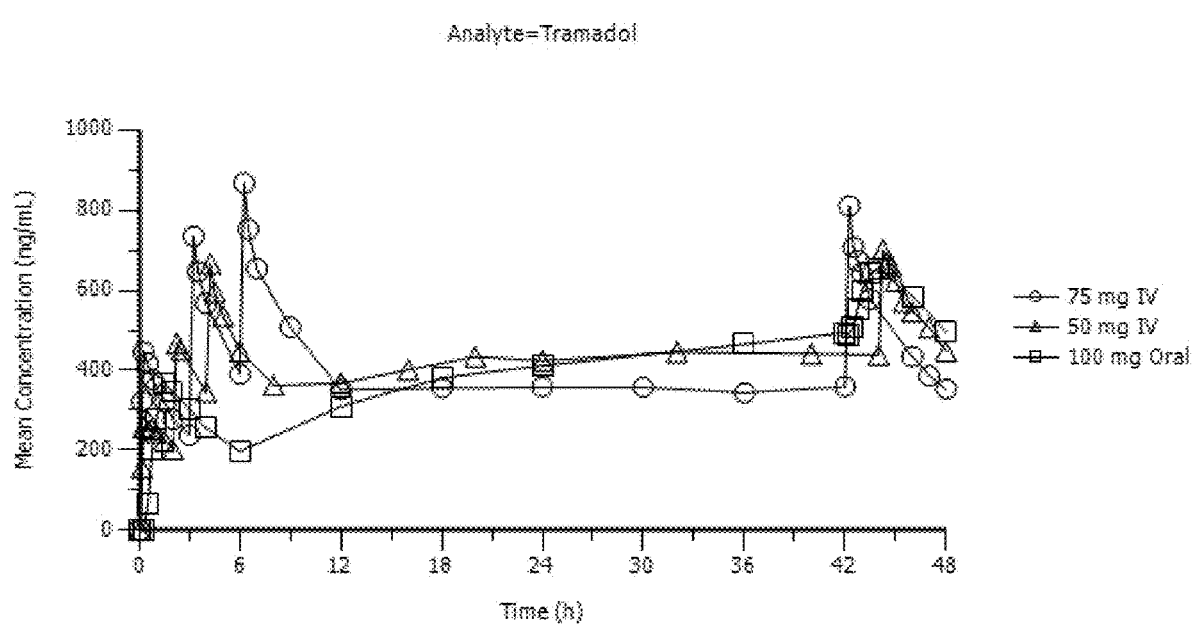
FIG. 9 provides the mean plasma tramadol time-concentration profiles for the 100 mg oral, 50 mg IV, and 75 mg IV regimens of the study conducted in Example 5.

FIG. 9 provides the mean plasma tramadol time-concentration profiles for the 100 mg oral, 50 mg IV, and 75 mg IV regimens. Mean plasma tramadol concentrations just after administration (for example at 3, 6, and 42 h) were higher after 75 mg IV q6 h compared to the administration of 50 mg IV q4 h and 100 mg PO q6 h. As evidenced from the trough/pre-dose samples between 24 and 42 h, the mean tranomadol concentrations were very similar for 50 mg IV q4 h and 100 mg PO q6 h but somewhat lower for 75 mg IV q6 h.

The mean tramadol concentrations for 50 mg IV q4 h and 100 mg PO q6 h were almost superimposable at the end of the pharmacokinetic sampling period, between approximately 44 and 48 h, suggesting that the two regimens provided similar steady-state concentrations (including trough and Cmax concentrations).

Figure 10:
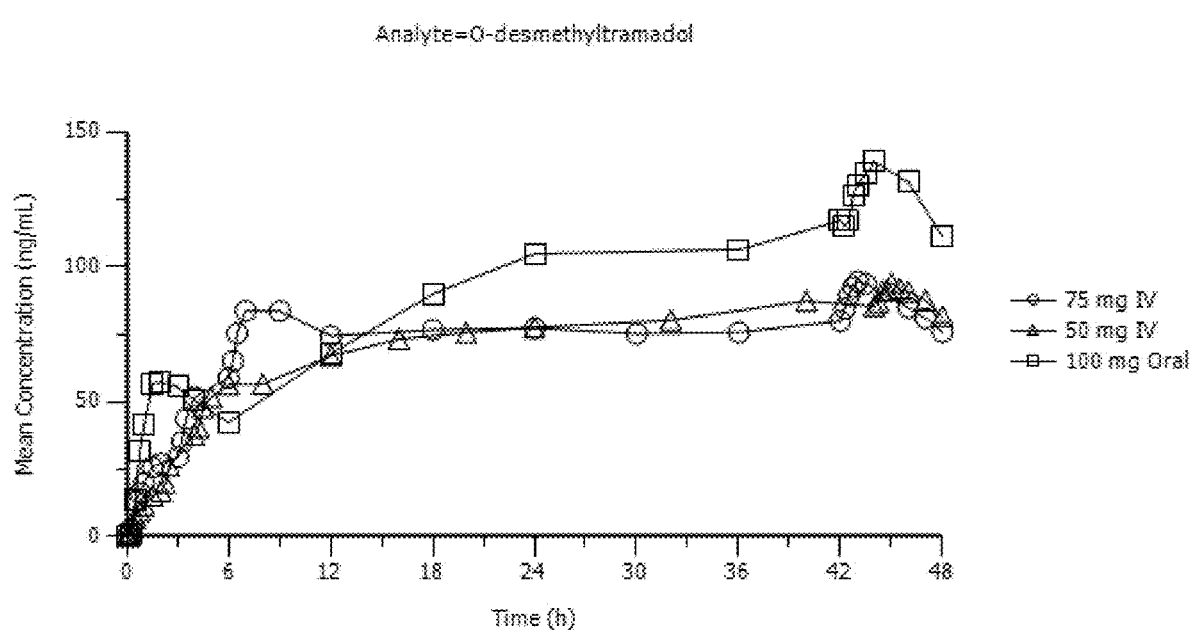
FIG. 10 provides the mean plasma O-desmethyltramadol time-concentration profiles for the 100 mg oral, 50 mg IV, and 75 mg IV regimens of the study conducted in Example 5.

FIG. 10 provides the mean plasma O-desmethyltramadol time-concentration profiles for the 100 mg oral, 50 mg IV, and 75 mg IV regimen. The mean plasma O-desmethyltramadol concentrations were higher for 75 mg IV q6 h following the 3rd dose at 6 h, but there was appreciable overlap of the trough concentrations for 75 mg IV q6 h and 50 mg IV q4 h between 24 and 42 h. The pre-dose concentrations as well as the concentrations after the last dose at 42 h were higher for 100 mg PO q6 h compared to both IV arms, presumably due to first pass metabolism which results in a higher fraction of the active metabolite in systemic circulation after oral administration.

Select pharmacokinetic parameters (overall Cmax, Cmax at steady-state, trough at steady-state, AUC over the last dosing interval for each regimen, ie, $AUC_{tau\ n}$) for tramadol are summarized in Table 10 below.

TABLE 10

Additional Plasma Pharmacokinetic Parameters of Tramadol

| Parameter | 75 mg IV | | | | 50 mg IV | | | | 100 mg Oral | | | |
| --- | --- | --- | --- | --- | --- | --- | --- | --- | --- | --- | --- | --- |
| | n | Mean | SD | CV % | n | Mean | SD | CV % | n | Mean | SD | CV % |
| $C_{max}$ (ng/mL) | 14 | 932 | 199 | 21.30 | 14 | 736 | 152 | 20.60 | 17 | 701 | 178 | 25.44 |
| $C_{max(42-48)}$ (ng/mL) | 14 | 827 | 234 | 28.24 | — | — | — | — | 17 | 701 | 178 | 25.44 |
| $C_{max(44-48)}$ (ng/mL) | — | — | — | — | 14 | 711 | 152 | 21.40 | — | — | — | — |
| $T_{48}$ (ng/mL) | 14 | 354 | 85.9 | 24.31 | 14 | 448 | 131 | 29.36 | 17 | 497 | 144 | 29.09 |
| Css (ng/mL) | 14 | 506 | 101 | 20.03 | 14 | 557 | 131 | 23.60 | 17 | 579 | 150 | 25.96 |

Exposure to O-desmethyltramadol was higher after 100 mg PO q6 h compared to either IV treatment, 50 mg IV q4 h or 75 mg IV q6 h. This was expected, considering the first pass metabolism after oral administration. Although exposure parameters were slightly higher for 75 mg IV q6 h compared to 50 mg IV q4 h through early time points, exposure to 0-desmethyltramadol was comparable for the two IV regimens when the entire pharmacokinetic sampling period was considered. For example, the mean Css for O-desmethyltramadol was 86.6 ng/mL for 75 mg IV q6 h and 88.9 ng/mL for 50 mg IV q4 h; the mean Css for 100 mg PO q6 h was higher, at 128 ng/mL. This is understandable taking into account the similarity in the total IV doses administered in the study (650 mg for the 50 mg IV q4 h arm, 675 mg for the 75 mg IV q6 h arm) and the slightly higher oral dose (800 mg for the 100 mg PO q6 h arm).

Figure 11:
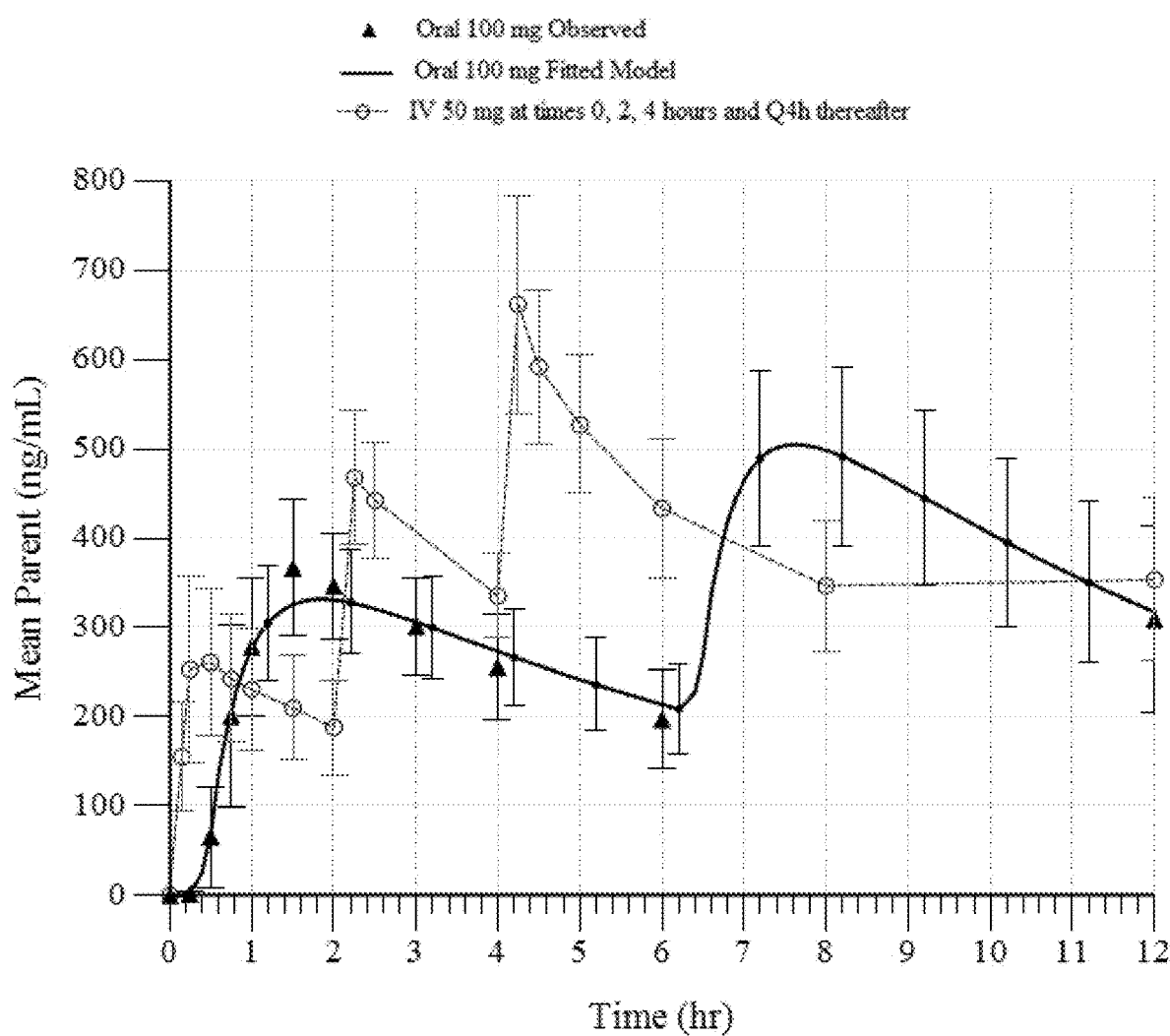
FIG. 11 provides the observed mean (STD) tramadol plasma concentration versus time curve for IV 50 mg and oral 100 mg as well as the fitted curve for the oral 100 mg for the initial 12 hours after administration for the study conducted in Example 5.
Figure 12:
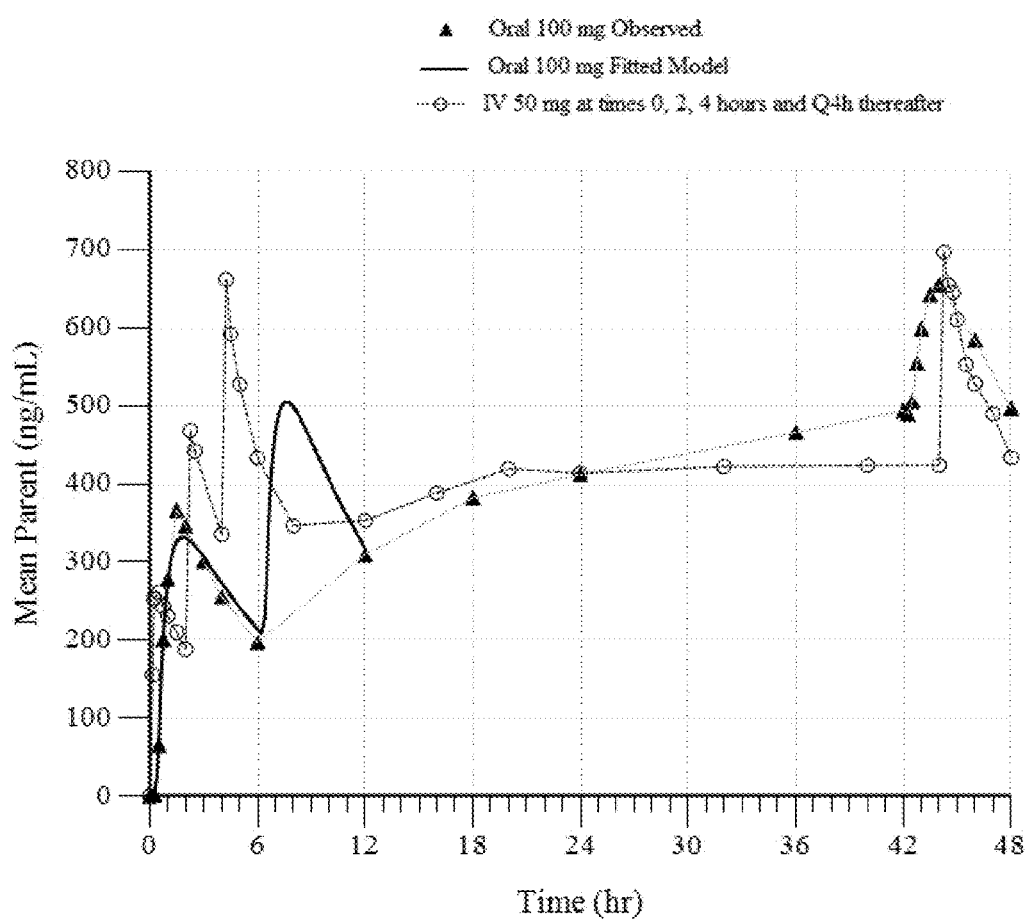
FIG. 12 is a graph illustrating that for Example 5, the 50 mg IV regimen is very close to steady-state after the 3rd dose, due to the loading dose strategy (comparable Cmax after the hour 4 dose to Cmax after the Hour 44 dose), and that the oral Cmax is achieved later but reaches a similar level to the 50 mg IV regimen.

The observed mean (STD) tramadol plasma concentration versus time curve for IV 50 mg and oral 100 mg as well as the fitted curve for the oral 100 mg for the initial 12 hours after administration is presented in FIG. 11. The fitted curve was obtained because the second oral peak was not measured in the study. The model fit was very good (as can be visually assessed in the figure), with the curve demonstrating the concentrations of the IV 50 mg regimen are generally higher after the Hour 2 dose. FIG. 12 illustrates that the 50 mg IV regimen is very close to steady-state after the 3rd dose, due to the loading dose strategy (comparable Cmax after the hour 4 dose to Cmax after the Hour 44 dose), and that the oral Cmax is achieved later but reaches a similar level to the 50 mg IV regimen.

Plasma pharmacokinetic parameters for tramadol in Example 5 are set forth in Table 11 below:

TABLE 11

| Parameter | 75 mg IV | | | | 50 mg IV | | | | 100 mg Oral | | | |
|---|---|---|---|---|---|---|---|---|---|---|---|---|
| | n | Mean | SD | CV % | n | Mean | SD | CV % | n | Mean | SD | CV % |
| $T_{max}$ (h) | 14 | 15.93 | 17.36 | 108.96 | 14 | 30.02 | 19.89 | 66.27 | 17 | 44.03 | 1.01 | 2.29 |
| $C_{max}$ (ng/mL) | 14 | 932 | 199 | 21.30 | 14 | 736 | 152 | 20.60 | 17 | 701 | 178 | 25.44 |
| $C_{1\,h}$ (ng/mL) | 14 | 361 | 63.8 | 17.65 | 14 | 243 | 45.2 | 18.56 | 17 | 278 | 77.0 | 27.72 |
| $C_2$ (ng/mL) | — | — | — | — | 14 | 203 | 31.6 | 15.59 | — | — | — | — |
| $C_3$ (ng/mL) | 14 | 237 | 41.6 | 17.53 | — | — | — | — | — | — | — | — |
| $C_6$ (ng/mL) | — | — | — | — | — | — | — | — | 17 | 197 | 55.0 | 27.93 |
| $T_{max(0-2)}$ (h) | — | — | — | — | 14 | 0.54 | 0.22 | 40.34 | — | — | — | — |
| $C_{max(0-2)}$ (ng/mL) | — | — | — | — | 14 | 294 | 68.5 | 23.27 | — | — | — | — |
| $T_{max(0-3)}$ (h) | 14 | 0.50 | 0.28 | 55.47 | — | — | — | — | — | — | — | — |
| $C_{max(0-3)}$ (ng/mL) | 14 | 484 | 155 | 31.93 | — | — | — | — | — | — | — | — |
| $T_{max(0-6)}$ (h) | — | — | — | — | — | — | — | — | 17 | 1.54 | 0.33 | 21.60 |
| $C_{max(0-6)}$ (ng/mL) | — | — | — | — | — | — | — | — | 17 | 377 | 68.9 | 18.31 |
| $T_{max(2-4)}$ (h) | — | — | — | — | 14 | 2.36 | 0.13 | 5.40 | — | — | — | — |
| $C_{max(2-4)}$ (ng/mL) | — | — | — | — | 14 | 479 | 77.7 | 16.23 | — | — | — | — |
| $T_{max(3-6)}$ (h) | 14 | 3.31 | 0.11 | 3.19 | — | — | — | — | — | — | — | — |
| $C_{max(3-6)}$ (ng/mL) | 14 | 756 | 141 | 18.65 | — | — | — | — | — | — | — | — |
| $T_{max(42-48)}$ (h) | 14 | 42.38 | 0.19 | 0.45 | — | — | — | — | 17 | 44.03 | 1.01 | 2.29 |
| $C_{max(42-48)}$ (ng/mL) | 14 | 827 | 234 | 28.24 | — | — | — | — | 17 | 701 | 178 | 25.44 |
| $T_{max(44-48)}$ (h) | — | — | — | — | 14 | 44.30 | 0.11 | 0.24 | — | — | — | — |
| $C_{max(44-48)}$ (ng/mL) | — | — | — | — | 14 | 711 | 152 | 21.40 | — | — | — | — |
| $C_{48}$ (ng/mL) | 14 | 354 | 85.9 | 24.31 | 14 | 448 | 131 | 29.36 | 17 | 497 | 144 | 29.09 |
| $AUC_{tau\,1}$ (h*ng/mL) | 14 | 1251 | 165.4 | 13.22 | 15 | 624.2 | 85.06 | 13.64 | 17 | 1494 | 282.3 | 18.90 |
| $AUC_{0-24}$ (h*ng/mL) | 14 | 9932 | 1958 | 19.72 | 14 | 9520 | 2106 | 22.12 | 17 | 7491 | 1936 | 25.85 |
| $AUC_{24-48}$ (h*ng/mL) | 14 | 9402 | 2511 | 26.71 | 14 | 11020 | 2852 | 25.88 | 17 | 11650 | 3387 | 29.07 |
| $AUC_{0-48}$ (h*ng/mL) | 14 | 19330 | 4427 | 22.90 | 14 | 20540 | 4906 | 23.89 | 17 | 19140 | 5172 | 27.02 |
| $AUC_{tau\,n}$ (h*ng/mL) | 14 | 3036 | 608.3 | 20.04 | 14 | 2228 | 525.6 | 23.60 | 17 | 3475 | 902.2 | 25.97 |
| $RAC(C_{max})$ | 14 | 1.7828 | 0.4975 | 27.91 | 14 | 2.4663 | 0.4953 | 20.08 | 17 | 1.8588 | 0.2858 | 15.37 |
| $RAC_{(trough)}$ | 14 | 1.5026 | 0.3613 | 24.05 | 14 | 2.1937 | 0.4768 | 21.74 | 17 | 2.5580 | 0.4577 | 17.89 |
| $RAC(AUC_{tau})$ | 14 | 2.4314 | 0.4060 | 16.70 | 14 | 3.5359 | 0.4662 | 13.18 | 17 | 2.3211 | 0.3437 | 14.81 |
| Css (ng/mL) | 14 | 506 | 101 | 20.03 | 14 | 557 | 131 | 23.60 | 17 | 579 | 150 | 25.96 |
| P/T Ratio First | 14 | 2.0658 | 0.6131 | 29.68 | 14 | 1.4566 | 0.2812 | 19.31 | 17 | 1.9824 | 0.3664 | 18.48 |
| P/T Ratio Last | 14 | 2.3692 | 0.5090 | 21.48 | 14 | 1.6370 | 0.2655 | 16.22 | 17 | 1.4400 | 0.2286 | 15.87 |

Plasma pharmacokinetic parameters of the O-desmethyl-tramadol metabolite in the study of Example 5 are set forth in Table 12:

TABLE 12

| Parameter | 75 mg IV | | | | 50 mg IV | | | | 100 mg Oral | | | |
|---|---|---|---|---|---|---|---|---|---|---|---|---|
| | n | Mean | SD | CV % | n | Mean | SD | CV % | n | Mean | SD | CV % |
| $T_{max}$ (h) | 14 | 32.99 | 16.50 | 50.01 | 14 | 44.95 | 1.59 | 3.53 | 17 | 43.97 | 1.12 | 2.54 |
| $C_{max}$ (ng/mL) | 14 | 99.2 | 25.6 | 25.85 | 14 | 96.6 | 24.5 | 25.35 | 17 | 146 | 37.4 | 25.62 |
| $C_{1\,h}$ (ng/mL) | 14 | 19.9 | 6.65 | 33.32 | 14 | 11.8 | 4.57 | 38.82 | 17 | 41.4 | 19.7 | 47.47 |
| $C_2$ (ng/mL) | — | — | — | — | 14 | 16.9 | 6.47 | 38.32 | — | — | — | — |
| $C_3$ (ng/mL) | 14 | 29.5 | 10.0 | 33.87 | — | — | — | — | — | — | — | — |
| $C_6$ (ng/mL) | — | — | — | — | — | — | — | — | 17 | 42.3 | 13.6 | 32.19 |
| $T_{max(0-2)}$ (h) | — | — | — | — | 14 | 1.85 | 0.19 | 10.34 | — | — | — | — |
| $C_{max(0-2)}$ (ng/mL) | — | — | — | — | 14 | 17.1 | 6.46 | 37.91 | — | — | — | — |
| $T_{max(0-3)}$ (h) | 14 | 2.71 | 0.49 | 18.03 | — | — | — | — | — | — | — | — |
| $C_{max(0-3)}$ (ng/mL) | 14 | 29.7 | 10.2 | 34.28 | — | — | — | — | — | — | — | — |
| $T_{max(0-6)}$ (h) | — | — | — | — | — | — | — | — | 17 | 2.04 | 0.87 | 42.42 |
| $C_{max(0-6)}$ (ng/mL) | — | — | — | — | — | — | — | — | 17 | 60.3 | 22.7 | 37.60 |
| $T_{max(2-4)}$ (h) | — | — | — | — | 14 | 3.95 | 0.00 | 0.00 | — | — | — | — |
| $C_{max(2-4)}$ (ng/mL) | — | — | — | — | 14 | 37.8 | 15.5 | 40.86 | — | — | — | — |
| $T_{max(3-6)}$ (h) | 14 | 5.81 | 0.52 | 8.98 | — | — | — | — | — | — | — | — |
| $C_{max(3-6)}$ (ng/mL) | 14 | 59.4 | 18.6 | 31.34 | — | — | — | — | — | — | — | — |
| $T_{max(42-48)}$ (h) | 14 | 43.10 | 0.36 | 0.84 | — | — | — | — | 17 | 43.97 | 1.12 | 2.54 |
| $C_{max(42-48)}$ (ng/mL) | 14 | 96.7 | 25.1 | 25.99 | — | — | — | — | 17 | 146 | 37.4 | 25.62 |
| $T_{max(44-48)}$ (h) | — | — | — | — | 14 | 45.31 | 0.68 | 1.50 | — | — | — | — |
| $C_{max(44-48)}$ (ng/mL) | — | — | — | — | 14 | 96.2 | 24.5 | 25.46 | — | — | — | — |
| $C_{48}$ (ng/mL) | 14 | 75.9 | 22.4 | 29.48 | 14 | 81.7 | 20.2 | 24.68 | 17 | 111 | 31.5 | 28.33 |
| $AUC_{tau\,1}$ (h*ng/mL) | 14 | 108.3 | 35.79 | 33.06 | 15 | 39.93 | 15.89 | 39.77 | 17 | 272.1 | 97.32 | 35.77 |
| $AUC_{0-24}$ (h*ng/mL) | 14 | 1608 | 428.2 | 26.63 | 14 | 1425 | 405.4 | 28.44 | 17 | 1655 | 476.6 | 28.79 |
| $AUC_{24-48}$ (h*ng/mL) | 14 | 1896 | 524.5 | 27.66 | 14 | 2002 | 514.9 | 25.72 | 17 | 2693 | 750.0 | 27.85 |
| $AUC_{0-48}$ (h*ng/mL) | 14 | 3504 | 931.2 | 26.58 | 14 | 3427 | 889.9 | 25.97 | 17 | 4349 | 1139 | 26.20 |
| $AUC_{tau\,n}$ (h*ng/mL) | 15 | 519.8 | 142.7 | 27.45 | 14 | 355.6 | 89.39 | 25.14 | 17 | 768.4 | 209.4 | 27.26 |
| $RAC(C_{max})$ | 14 | 3.4575 | 0.8063 | 23.32 | 14 | 6.0794 | 1.4574 | 23.97 | 17 | 2.7316 | 1.2718 | 46.56 |
| $RAC_{(trough)}$ | 14 | 2.7237 | 0.7000 | 25.70 | 14 | 5.2872 | 1.4637 | 27.68 | 17 | 2.7839 | 1.0135 | 36.41 |
| $RAC(AUC_{tau})$ | 14 | 5.0884 | 1.2051 | 23.68 | 14 | 9.7100 | 2.6019 | 26.80 | 17 | 3.1287 | 1.5078 | 48.19 |
| Css (ng/mL) | 14 | 86.6 | 23.8 | 27.44 | 14 | 88.9 | 22.3 | 25.14 | 17 | 128 | 34.9 | 27.25 |

TABLE 12-continued

| | 75 mg IV | | | | 50 mg IV | | | | 100 mg Oral | | |
|---|---|---|---|---|---|---|---|---|---|---|---|
| Parameter | n | Mean | SD | CV % | n | Mean | SD | CV % | n | Mean | SD | CV % |
| P/T Ratio First | 14 | 1.0049 | 0.0185 | 1.84 | 14 | 1.0122 | 0.0327 | 3.23 | 17 | 1.3982 | 0.1890 | 13.52 |
| P/T Ratio Last | 14 | 1.2878 | 0.1073 | 8.33 | 14 | 1.1782 | 0.0772 | 6.55 | 17 | 1.3302 | 0.1635 | 12.29 |
| M/P Ratio $C_{1\,h}$ | 14 | 0.0571 | 0.0232 | 40.64 | 14 | 0.0503 | 0.0224 | 44.54 | 17 | 0.1579 | 0.0798 | 50.54 |
| M/P Ratio $T_{48}$ | 14 | 0.2266 | 0.0796 | 35.14 | 14 | 0.2002 | 0.0794 | 39.67 | 17 | 0.2423 | 0.0929 | 38.33 |

The term "STD" as used herein means standard deviation. The term "$C_2$" means plasma concentration of tramadol at time 2 or hour 2 (in other words, the tramadol plasma concentration at 2 hours after the first administered tramadol dose). The term "$C_3$" means plasma concentration of tramadol at time 3 or hour 3 (in other words, the tramadol plasma concentration at 3 hours after the first administered tramadol dose). The term "C6" as used herein means plasma concentration of tramadol at time 6 or hour 6 (in other words, the tramadol plasma concentration at 6 hours after the first administered tramadol dose). The term "$C_{48}$" as used herein means plasma concentration of tramadol at time 48 or hour 48 (in other words, the tramadol plasma concentration at 48 hours after the first administered tramadol dose). The term "$C_{ss}$" means steady-state concentration. The term "$C_{max}$" means maximum concentration. The term "AUC" means area under the curve. The term "$AUC_{tau}$" means area under the plasma concentration-time curve over the dosing interval. As opposed to $AUC_{(0-inf)}$ which is extrapolated out to infinity, $AUC_{tau\,n}$ is the AUC in the last dosing interval (for example, with respect to the 50 mg dosing regimen, that would be at 44-48 hours from first dose). The term "RAC" means ratio of accumulation from first dose to steady-state. (Thus, if a patient had a $C_{max}$ of 500 ng/ml in the first interval, and 1000 ng/mL at steady-state, the RAC is 1000/500=2.0). The term "P/T" means peak to trough. The term "M/P" means metabolite to parent (tramadol) ratio.

The mean tramadol $C_{max}$ for the first dose ranged from 294 ng/mL after 50 mg IV ($C_{max(0-2)}$) to 484 ng/mL after 75 mg IV ($C_{max(0-3)}$); the $C_{max}$ after the first 100 mg PO ($C_{max(0-6)}$) was 377 ng/mL. Over the entire pharmacokinetic sampling period, the $C_{max}$ for 75 mg IV q6 h was somewhat higher, 932 ng/mL, compared to the other treatments. The $C_{max}$ after 50 mg IV q4 h and 100 mg PO q6 h were similar, at 736 ng/mL and 701 ng/mL, respectively. Of particular note, the $C_{max}$ at steady-state for 50 mg IV was 711 ng/ml, while for the oral dose it was 701 ng/mL.

The higher peak concentrations for 75 mg IV q6 h was reflected in the fluctuation between the peak and trough concentration; the P/T Ratios for the first and last doses of 75 mg IV q6 h were larger (2.0658 to 2.3692) than those observed for 50 mg IV q4 h (1.4566 to 1.6370) and 100 mg PO q6 h (1.4400 to 1.9824). This result was expected, considering longer 6-hour dosing interval for the 75 mg IV treatment, compared to the 50 mg IV treatment, and more time for drug elimination prior to subsequent dosing.

During the last 24-hour sampling period ($AUC_{24-48}$), the exposure to tramadol after 100 mg PO q6 h (11650 h*ng/mL) was comparable to that after 50 mg IV q4 h (11020 h*ng/mL); the $AUC_{24-48}$ for 75 mg IV q6 h was somewhat lower (9932 h*ng/mL). Two additional AUCs were calculated at the time of pharmacokinetic analysis, $AUC_{tau\,1}$ (the AUC during the first dosing interval) and $AUC_{tau\,n}$ (the AUC during the last dosing interval). $AUC_{tau\,1}$ and $AUC_{tau\,n}$ were used to provide another measure of the accumulation during multiple dosing. $AUC_{tau\,n}$ was used to characterize the exposure at steady-state during a consistent regimen. Although $AUC_{tau\,n}$ cannot be compared directly across all treatments, due to the different dosing intervals of 4 or 6 h, these AUCs can be used to estimate systemic exposure over a given multiple of these intervals, such as 12 h. The predicted exposure over 12 h at steady state was comparable for 50 mg IV q4 h (3×2228=6684 h*ng/mL) and 100 mg PO q6 h (2×3475=6950 h*ng/mL), but somewhat lower for 75 mg IV q6 h (2×3036=6072 h*ng/mL). These values correlate well with the average concentration at steady-state (Css), at 557 ng/mL and 579 ng/mL for 50 mg IV q4 h and 100 mg PO q6 h, respectively, and 506 ng/mL for 75 mg IV q6 h.

The accumulation factors for tramadol ranged from 1.5026 to 2.4314 for 75 mg IV q6 h, from 2.1937 to 3.5359 for 50 mg IV q4 h, and from 1.8588 to 2.5580 for 100 mg PO q6 h. Overall, these values are in good agreement with the theoretical accumulation factors of 1.82 for a 6-h dosing interval and 2.42 for a 4-h dosing interval, calculated as $1/[1-\exp(\ln 2*tau/T_{1/2})]$ and using $T_{1/2}$ of approximately 5.2 h. The shorter dosing interval results in a higher degree of accumulation at steady-state, relative to the concentrations observed after the first dose, but less fluctuation in the concentrations during the dosing interval.

The 75 mg IV/100 mg PO ratios ranged from 74.67 to 137.94%, indicating higher exposure to tramadol after 75 mg IV q6 h compared to 100 mg PO q6 h in general, most apparent through 24 hours. Based on the 80.00-125.00% acceptance criteria for the 90% confidence intervals, $AUC_{0-48}$ was not significantly different between these treatments. The 50 mg IV/100 mg PO ratios ranged from 89.82 to 127.81%, and only $AUC_{0-24}$ had 90% confidence intervals outside the 80.00-125.00% range; $C_{max}$, $AUC_{24-48}$, $AUC_{0-48}$, and $T_{48}$ were not significantly different between these treatments. The 75 mg IV/50 mg IV ratios ranged from 83.13 to 129.16%; although the AUCs were not significantly different across these treatments, the $C_{max}$ and $T_{48}$ concentrations were, reflecting the more pronounced fluctuation in tramadol concentrations for the 75 mg IV q6 h arm.

Exposure to O-desmethyltramadol was higher after 100 mg PO q6 h compared to either IV treatment, 50 mg IV q4 h or 75 mg IV q6 h. This was expected, considering the first pass metabolism after oral administration. Although exposure parameters were slightly higher for 75 mg IV q6 h compared to 50 mg IV q4 h through early time points, exposure to O-desmethyltramadol was comparable for the two IV regimens when the entire pharmacokinetic sampling period was considered. For example, the mean Css for O-desmethyltramadol was 86.6 ng/mL for 75 mg IV q6 h and 88.9 ng/mL for 50 mg IV q4 h; the mean Css for 100 mg PO q6 h was higher, at 128 ng/mL. This is understandable taking into account the similarity in the total IV doses administered in the study (650 mg for the 50 mg IV q4 h arm, 675 mg for the 75 mg IV q6 h arm) and the slightly higher oral dose (800 mg for the 100 mg PO q6 h arm).

The following conclusions are drawn from Example 5: (1) the 50 mg IV regimen, as compared to the 75 mg IV regimen, resulted in less peak to trough fluctuation with lower Cmax. This regimen also provided a pharmacokinetic profile very similar to the 100 mg oral dose regimen; and (2) exposure to O-desmethyltramadol was higher after 100 mg PO q6 h compared to either IV treatment, 50 mg IV or 75 mg IV regimens, based on AUC and Cmax values; (3) overall Cmax was comparable between the 50 mg IV and 100 mg PO regimens; exposure at steady-state to tramadol, based on Cmax and AUC, was also comparable between 50 mg IV q4 h and 100 mg PO q6 h; (4) administration of a lower IV dose more frequently, as in the 50 mg IV q4 h regimen compared to the 75 mg IV q6 regimen, resulted in less fluctuation during the dosing interval and a pharmacokinetic profile very similar to the 100 mg oral dose; (5) compared to the 50 mg IV q4 h and 100 mg PO q6 h regimens, greater peak to trough variance in tramadol concentrations was observed for the 75 mg IV q6 h regimen. The data from Example 5 demonstrate that the 50 mg IV dosing regimen (with tramadol 50 mg at Hour 0, followed by 50 mg at Hour 2, 50 mg at hour 4, and 50 mg every 4 hours thereafter through Hour 44) provides a preferred result.

CONCLUSION

All patents and publications identified in the above paragraphs are hereby incorporated by reference in their entireties. It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims. All of the patents and publications cited herein are hereby incorporated by reference.

What is claimed is:

1. A method of administering tramadol for treating acute pain in a human patient(s) via an intravenous dosing regimen, comprising
   intravenously administering a first dose of tramadol to a human patient(s) experiencing acute pain in an amount of about 60 mg;
   and thereafter intravenously administering additional doses of tramadol to the human patient(s) in an amount of about 60 mg tramadol at dosage intervals of about 6 hours, except that a second dose is intravenously administered as a loading dose at a shortened interval as compared to the dosage interval of about 6 hours, such that a total of 5 doses of 60 mg tramadol are intravenously administered on the first day of treatment and the intravenous tramadol is administered on subsequent days of treatment on a basis of a total of 4 doses of 60 mg tramadol per day until the intravenous tramadol administration is terminated, and wherein the tramadol is tramadol base or a pharmaceutically acceptable salt of tramadol, such that the intravenous dosing regimen provides a steady-state Cmax of tramadol which is similar to the steady-state Cmax of 100 mg tramadol HCl given every 6 hours.

2. The method of claim 1, further comprising administering the first dose of intravenous tramadol on first demand of analgesia postoperatively.

3. The method of claim 1, further comprising administering the first dose of intravenous tramadol to the patient intraoperatively at wound closure.

4. The method of claim 1, continuing to administer additional doses of tramadol to the human patient in an amount of about 60 mg tramadol at dosage intervals of about 6 hours for at least about 44 hours after the first administered dose of tramadol.

5. The method of claim 1, further comprising administering the second dose such that the Cmax and Cmin levels obtained during the initial 24 hour dosing interval are similar to the Cmax and Cmin levels obtained during the initial 24 hour dosing interval for a 100 mg immediate release oral tramadol dose given every 6 hours, but not significantly greater than the steady-state Cmax level for a 100 mg immediate release oral tramadol dose given every 6 hours.

6. The method of claim 1, wherein the second dose is administered at from about 2 to about 3 hours after the first dose.

7. A method of administering tramadol for treating acute postoperative pain in a human patient(s) via an intravenous dosing regimen, comprising
   intravenously administering a first dose of tramadol to a human patient(s) experiencing acute pain in an amount of about 60 mg;
   and thereafter intravenously administering additional doses of tramadol to the human patient(s) in an amount of about 60 mg tramadol at dosage intervals of about 6 hours, except that a second dose is intravenously administered as a loading dose at a shortened interval as compared to the dosage interval of about 6 hours, such that a total of 5 doses of 60 mg tramadol are intravenously administered on the first day of treatment and the intravenous tramadol is administered on subsequent days of treatment on a basis of a total of 4 doses of 60 mg tramadol per day until the intravenous tramadol administration is terminated, and wherein the tramadol is tramadol base or a pharmaceutically acceptable salt of tramadol, the dosing regimen providing a plasma level of tramadol which is similar to but does not substantially exceed the maximum (Cmax) plasma levels of tramadol obtained at steady-state by a 100 mg oral tramadol dose given every 6 hours prior to the end of the initial 24 hours of intravenous tramadol administration.

8. The method of claim 7, further comprising administering the first dose of intravenous tramadol on first demand of analgesia postoperatively.

9. The method of claim 7, further comprising administering the first dose of intravenous tramadol to the patient intraoperatively at wound closure.

10. The method of claim 7, further comprising continuing to administer additional doses of tramadol to the human patient in an amount of about 60 mg tramadol at dosage intervals of about 6 hours for at least about 44 hours after the first administered dose of tramadol.

11. The method of claim 7, further comprising continuing to administer additional doses of tramadol to the human patient in an amount of about 60 mg tramadol at dosage intervals of about 6 hours for at least about 44 hours after the first administered dose of tramadol, such that the intravenous dosing regimen provides a Cmax of tramadol at steady-state of about 736 ng/mL±152.

12. A method of administering tramadol for treating acute postoperative pain in a human patient(s) via an intravenous dosing regimen, comprising intravenously administering a first dose of tramadol to a human patient(s) experiencing acute pain in an amount of about 60 mg;

and thereafter intravenously administering additional doses of tramadol to the human patient(s) in an amount of about 60 mg tramadol at dosage intervals of about 6 hours, except that a second dose is intravenously administered as a loading dose at a shortened interval as compared to the dosage interval of about 6 hours, such that a total of 5 doses of 60 mg tramadol are intravenously administered on the first day of treatment and the intravenous tramadol is administered on subsequent days of treatment on a basis of a total of 4 doses of 60 mg tramadol per day until the intravenous tramadol administration is terminated, and wherein the tramadol is tramadol base or a pharmaceutically acceptable salt of tramadol, such that the Cmax of the intravenous dosing regimen does not substantially exceed the concentration provided by 100 mg oral tramadol administered every 6 hours at steady-state by more than 15%.

13. The method of claim 12, further comprising administering the second dose such that the Cmax and Cmin levels obtained during the initial 24 hour dosing interval are similar to the Cmax and Cmin levels obtained during the initial 24 hour dosing interval for a 100 mg immediate release oral tramadol dose given every 6 hours, but not significantly greater than the steady-state Cmax level for a 100 mg immediate release oral tramadol dose given every 6 hours.

14. The method of claim 12, wherein the second dose is administered at from about 2 to about 3 hours after the first dose.

15. The method of claim 12, wherein the intravenous dosing regimen provides a Cmax of tramadol at steady-state of about 736 ng/mL±152.

* * * * *